US011639522B2

(12) United States Patent
Schaus et al.

(10) Patent No.: US 11,639,522 B2
(45) Date of Patent: May 2, 2023

(54) MICROSCOPE-FREE IMAGING

(71) Applicant: President and Fellows of Harvard College, Cambridge, MA (US)

(72) Inventors: Thomas E. Schaus, Arlington, MA (US); Xi Chen, West Newton, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 226 days.

(21) Appl. No.: 15/542,953

(22) PCT Filed: Jan. 29, 2016

(86) PCT No.: PCT/US2016/015503
§ 371 (c)(1),
(2) Date: Dec. 4, 2017

(87) PCT Pub. No.: WO2016/123419
PCT Pub. Date: Aug. 4, 2016

(65) Prior Publication Data
US 2018/0010174 A1    Jan. 11, 2018

Related U.S. Application Data

(60) Provisional application No. 62/110,050, filed on Jan. 30, 2015.

(51) Int. Cl.
*C12Q 1/6841* (2018.01)
*C12Q 1/6804* (2018.01)
*G01N 33/53* (2006.01)

(52) U.S. Cl.
CPC ......... *C12Q 1/6841* (2013.01); *C12Q 1/6804* (2013.01); *G01N 33/5308* (2013.01); *G01N 2458/10* (2013.01)

(58) Field of Classification Search
CPC ............... C12Q 1/6841; C12Q 1/6804; C12Q 2521/501; C12Q 2525/161; C12Q 2525/185; C12Q 2525/301; C12Q 2531/113; C12Q 2535/122; C12Q 2563/107; C12Q 2565/601; G01N 33/5308; G01N 2458/10
See application file for complete search history.

(56) References Cited

U.S. PATENT DOCUMENTS

| | | | |
|---|---|---|---|
| 5,030,566 A | 7/1991 | Son et al. | |
| 5,543,507 A | 8/1996 | Cook et al. | |
| 5,635,352 A | 6/1997 | Urdea et al. | |
| 5,866,336 A | 2/1999 | Nazarenko et al. | |
| 6,143,495 A | 11/2000 | Lizardi et al. | |
| 7,033,758 B2 | 4/2006 | Kenny et al. | |
| 8,623,302 B2 * | 1/2014 | Chuntonov | B22F 5/10 252/181.7 |
| 8,623,602 B2 * | 1/2014 | Kubista | C12Q 1/686 435/6.12 |
| 8,772,011 B2 * | 7/2014 | De Maria | A23K 20/189 435/221 |
| 8,962,241 B2 | 2/2015 | Yin et al. | |
| 9,273,349 B2 * | 3/2016 | Nguyen | C12Q 1/6816 |
| 9,879,313 B2 * | 1/2018 | Chee | C12Q 1/6841 |
| 10,876,971 B2 | 12/2020 | Lin et al. | |
| 11,098,355 B2 * | 8/2021 | Heron | C12Q 1/6869 |
| 2002/0064772 A1 | 5/2002 | Gildea et al. | |
| 2002/0065609 A1 * | 5/2002 | Ashby | C12Q 1/6809 702/20 |
| 2003/0207292 A1 | 11/2003 | Notomi et al. | |
| 2005/0045063 A1 | 3/2005 | Niggemann et al. | |
| 2006/0063196 A1 | 3/2006 | Akeson et al. | |
| 2006/0188902 A1 | 8/2006 | Narayanan et al. | |
| 2006/0286570 A1 * | 12/2006 | Rowlen | C12Q 1/6816 435/6.12 |
| 2007/0031829 A1 * | 2/2007 | Yasuno | C12Q 1/6886 435/6.12 |
| 2007/0042419 A1 * | 2/2007 | Barany | C12Q 1/6813 435/6.12 |
| 2008/0021205 A1 | 1/2008 | Blau et al. | |
| 2011/0129834 A1 | 6/2011 | Chen et al. | |
| 2011/0300640 A1 | 12/2011 | Josten et al. | |
| 2012/0014977 A1 * | 1/2012 | Furihata | C07K 14/4748 424/185.1 |
| 2012/0021410 A1 | 1/2012 | Yin et al. | |
| 2012/0022243 A1 | 1/2012 | Yin | |

(Continued)

FOREIGN PATENT DOCUMENTS

| | | |
|---|---|---|
| CN | 1432061 A | 7/2003 |
| CN | 1836050 A | 9/2006 |

(Continued)

OTHER PUBLICATIONS

"How many species of bacteria are there?", WiseGeek.com, accessed Jan. 21, 2014. (Year: 2014).*
"List of sequenced bacterial genomes", Wikipedia.com; accessed Jan. 24, 2014. (Year: 2014).*
Sah et al., "Complete Genome Sequence of a 2019 Novel Coronavirus (SARS-CoV-2) Strain Isolated in Nepal", Microbiology, vol. 9, Issue 11, Mar. 12, 2020, pp. 1-3. (Year: 2019).*
Zeberg et al., "The major genetic risk factor for severe COVID-19 is inherited from Neanderthals", Nature, Sep. 30, 2020, pp. 1-13. (Year: 2020).*
Foster et al., "A human gut bacterial genome and culture collection for improved metagenomic analysis", Nature Biotechnology, vol. 37, Feb. 2019, 186-192. (Year: 2019).*

(Continued)

*Primary Examiner* — Narayan K Bhat
(74) *Attorney, Agent, or Firm* — Wolf, Greenfield & Sacks, P.C.

(57) ABSTRACT

Provided herein, in some aspects, are methods of imaging molecules without a microscope or other specialized equipment, referred to herein as "microscope-free imaging (MFI)." Herein, "molecular instruments" (e.g., DNA-based and protein-based molecules) are used, instead of microscopes, in a "bottom-up" approach for inspecting molecular targets.

19 Claims, 34 Drawing Sheets

Specification includes a Sequence Listing.

(56) References Cited

U.S. PATENT DOCUMENTS

| | | | |
|---|---|---|---|
| 2012/0165219 A1* | 6/2012 | Van Der Zaag | C12Q 1/6834 506/9 |
| 2012/0231972 A1* | 9/2012 | Golyshin | C12Q 1/00 506/11 |
| 2012/0253689 A1* | 10/2012 | Rogan | G16B 30/00 702/20 |
| 2013/0072390 A1* | 3/2013 | Wang | C12P 19/28 506/9 |
| 2013/0225623 A1* | 8/2013 | Buxbaum | A61K 31/44 514/277 |
| 2014/0087377 A1 | 3/2014 | Park et al. | |
| 2014/0141984 A1 | 5/2014 | Swartz et al. | |
| 2014/0255921 A1 | 9/2014 | Moysey et al. | |
| 2014/0349288 A1* | 11/2014 | Church | C12Q 1/6837 435/6.11 |
| 2015/0107475 A1 | 4/2015 | Jung et al. | |
| 2016/0312272 A1 | 10/2016 | Barish et al. | |
| 2017/0349939 A1 | 12/2017 | Metzker et al. | |
| 2018/0073068 A1 | 3/2018 | Peter et al. | |
| 2018/0148775 A1 | 5/2018 | Wang et al. | |
| 2019/0285644 A1 | 9/2019 | Regev et al. | |
| 2020/0102556 A1 | 4/2020 | Da Veiga Beltrame et al. | |
| 2020/0109426 A1 | 4/2020 | Xuan et al. | |
| 2020/0362398 A1 | 11/2020 | Kishi et al. | |
| 2021/0019973 A1 | 1/2021 | Yin et al. | |
| 2021/0147902 A1 | 4/2021 | Saka et al. | |
| 2021/0277452 A1 | 9/2021 | Kim et al. | |
| 2021/0388430 A1 | 12/2021 | Zhang et al. | |

FOREIGN PATENT DOCUMENTS

| | | | |
|---|---|---|---|
| CN | 101048505 A | 10/2007 | |
| CN | 101541975 A | 9/2009 | |
| CN | 102317471 A | 1/2012 | |
| CN | 102782158 A | 11/2012 | |
| CN | 103014168 A | 4/2013 | |
| CN | 104164488 A | 11/2014 | |
| JP | 2008-017853 A | 1/2008 | |
| JP | 2013-540451 A | 11/2013 | |
| JP | 2014-504153 A | 2/2014 | |
| JP | 2015-523864 A | 8/2015 | |
| JP | 2002-503948 A | 5/2020 | |
| WO | WO 01/94625 A2 | 12/2001 | |
| WO | WO 2004/046321 A2 | 6/2004 | |
| WO | WO 2007/117256 A1 | 10/2007 | |
| WO | WO 2010/107416 A1 | 9/2010 | |
| WO | WO 2010/146349 A1 | 12/2010 | |
| WO | WO 2011/156434 A2 | 12/2011 | |
| WO | WO 2012/057689 A1 | 5/2012 | |
| WO | WO 2012/058488 A1 | 5/2012 | |
| WO | WO 2012/071428 A2 | 5/2012 | |
| WO | WO 2012/078312 A2 | 6/2012 | |
| WO | WO 2012/112804 A1 | 8/2012 | |
| WO | WO 2013/012434 A1 | 1/2013 | |
| WO | WO 2013/022694 A1 | 2/2013 | |
| WO | WO 2013/140107 A1 | 9/2013 | |
| WO | WO 2013/188912 A1 | 12/2013 | |
| WO | WO 2014/018675 A1 | 1/2014 | |
| WO | WO 2014/071361 A1 | 5/2014 | |
| WO | WO 2014/074597 A1 | 5/2014 | |
| WO | WO 2014/130388 A1 | 8/2014 | |
| WO | WO-2014130388 A1 * | 8/2014 | C12Q 1/6869 |
| WO | WO 2014/135838 A1 | 9/2014 | |
| WO | WO-2014135838 A1 * | 9/2014 | C12N 9/14 |
| WO | WO-2014144371 A1 * | 9/2014 | C12Q 1/682 |
| WO | WO 2015/095633 A1 | 6/2015 | |
| WO | WO 2015/114469 A2 | 8/2015 | |
| WO | WO 2015/178978 A2 | 11/2015 | |
| WO | WO 2016/011089 A1 | 1/2016 | |
| WO | WO 2016/032562 A1 | 3/2016 | |
| WO | WO 2016/144755 A1 | 9/2016 | |
| WO | WO 2017/143006 A1 | 8/2017 | |
| WO | WO 2017/205719 A1 | 11/2017 | |
| WO | WO 2018/057502 A1 | 3/2018 | |
| WO | WO 2019/147945 A1 | 8/2019 | |
| WO | WO 2019/183359 A1 | 9/2019 | |

OTHER PUBLICATIONS

Sah et al., "Complete Genome Sequence of a 2019 Novel Coronavirus (SARS-CoV-2) Strain Isolated in Nepal", Microbiology, vol. 9, Issue 11, Mar. 12, 2020, pp. 1-3. (Year: 2020).*

"New COVID-19 Variants", Centers for Disease Control and Prevention, Jan. 15, 2021, pp. 1-3. (Year: 2021).*

Assarsson et al., Homogenous 96-plex PEA immunoassay exhibiting high sensitivity, specificity, and excellent scalability. PLoS One. Apr. 22, 2014;9(4):e95192 (1-11). doi: 10.1371/journal.pone.0095192. eCollection 2014.

Beliveau et al., Versatile design and synthesis platform for visualizing genomes with Oligopaint FISH probes. Proc Natl Acad Sci USA. Dec. 26, 2012;109(52):21301-6. doi:10.1073/pnas.1213818110. Epub Dec. 11, 2012.

Choi et al., Next-generation in situ hybridization chain reaction: higher gain, lower cost, greater durability. ACS Nano. May 27, 2014;8(5):4284-94. doi: 10.1021/nn405717p. Epub Apr. 8, 2014.

Christensen et al., Role of the Bombyx mori R2 element N-terminal domain in the target-primed reverse transcription (TPRT) reaction. Nucleic Acids Res. Nov. 10, 2005;33(20):6461-8.

Dirks et al., Triggered amplification by hybridization chain reaction. Proc Natl Acad Sci U S A. Oct. 26, 2004;101(43): 15275-8. Epub Oct. 18, 2004.

Fields et al., A novel genetic system to detect protein-protein interactions. Nature. Jul. 20, 1989;340(6230):245-6.

Fredriksson et al., Protein detection using proximity-dependent DNA ligation assays. Nat Biotechnol. May 2002;20(5):473-7.

Geiss et al., Direct multiplexed measurement of gene expression with color-coded probe pairs. Nat Biotechnol. Mar. 2008;26(3):317-25. doi: 10.1038/nbt1385. Epub Feb. 17, 2008.

Giepmans et al., The fluorescent toolbox for assessing protein location and function. Science. Apr. 14, 2006;312(5771):217-24.

Green et al., Toehold switches: de-novo-designed regulators of gene expression. Cell. Nov. 6, 2014;159(4):925-39. doi: 10.1016/j.cell.2014.10.002. Epub Oct. 23, 2014.

Iinuma et al., Polyhedra self-assembled from DNA tripods and characterized with 3D DNA-PAINT. Science. Apr. 4, 2014;344(6179):65-9. doi: 10.1126/science.1250944. Epub Mar. 13, 2014.

Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.

Jungmann et al., Single-molecule kinetics and super-resolution microscopy by fluorescence imaging of transient binding on DNA origami. Nano Lett. Nov. 10, 2010;10(11):4756-61.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Li et al., Multiplexed detection of pathogen DNA with DNA-based fluorescence nanobarcodes. Nat Biotechnol. Jul. 2005;23(7):885-9. Epub Jun. 12, 2005.

Lin et al., Submicrometre geometrically encoded fluorescent barcodes self-assembled from DNA. Nat Chem. Oct. 2012;4(10):832-9.

Radding et al., Uptake of homologous single-stranded fragments by superhelical DNA. IV. Branch migration. J Mol Biol. Nov. 1977;116(4):825-39.

Raj et al., Imaging individual mRNA molecules using multiple singly labeled probes. Nat Methods. Oct. 2008;5(10):877-9. doi: 10.1038/nmeth.1253. Epub Sep. 21, 2008.

Rothemund, Folding DNA to create nanoscale shapes and patterns. Nature. Mar. 16, 2006;440(7082):297-302.

Santalucia et al., The thermodynamics of DNA structural motifs. Annu Rev Biophys Biomol Struct. 2004;33:415-40.

Smith et al., Overstretching B-DNA: the elastic response of individual double-stranded and single-stranded DNA molecules. Science. Feb. 9, 1996;271(5250):795-9.

(56) References Cited

OTHER PUBLICATIONS

Woo et al., Programmable molecular recognition based on the geometry of DNA nanostructures. Nat Chem. Aug. 2011;3(8):620-7. doi: 10.1038/nchem.1070. Epub Jul. 10, 2011. Erratum in: Nat Chem. Oct. 2011;3(10):829. Nat Chem. 2011;3(8):620-7.
Yin et al., Programming biomolecular self-assembly pathways. Nature. Jan. 17, 2008;451(7176):318-22. doi:10.1038/nature06451.
Yoshimura et al., Ultrafast reversible photo-cross-linking reaction: toward in situ DNA manipulation. Org Lett. Aug. 7, 2008;10(15):3227-30. doi:10.1021/ol801112j. Epub Jun. 27, 2008.
Yurke et al., A DNA-fuelled molecular machine made of DNA. Nature. Aug. 10, 2000;406(6796):605-8.
Zadeh et al., NUPACK: Analysis and design of nucleic acid systems. J Comput Chem. Jan. 15, 2011;32(1):170-3. doi: 10.1002/jcc.21596. Epub Jul. 19, 2010.
Zhang et al., Control of DNA strand displacement kinetics using toehold exchange. J Am Chem Soc. Dec. 2, 2009;131(47):17303-14. doi: 10.1021/ja906987s. Epub Nov. 6, 2009.
Zhang et al., Dynamic DNA nanotechnology using strand-displacement reactions. Nat Chem. Feb. 2011;3(2):103-13. doi: 10.1038/nchem.957. Epub Jan. 24, 2011.
Baccouche et al., Dynamic DNA-toolbox reaction circuits: a walkthrough. Methods. May 15, 2014;67(2):234-49. doi: 10.1016/j.ymeth.2014.01.015. Epub Feb. 2, 2014.
Chen et al., Conditionally fluorescent molecular probes for detecting single base changes in double-stranded DNA. Nat Chem. 2013;5(9):782-9. Author Manuscript, 16 pages.
Mongtagne et al., Programming an in vitro DNA oscillator using a molecular networking strategy. Mol SystBiol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.
Pardee et al., Paper-based synthetic gene networks. Cell. Nov. 6, 2014;159(4):940-54. doi: 10.1016/j.cell.2014.10.004. Epub Oct. 23, 2014.
Tribioli et al., Long-term room temperature storage of high-quality embryonic stem cell genomic DNA extracted with a simple and rapid procedure. J Biomol Tech. Sep. 2006;17(4):249-51.
Weibrecht et al., In situ detetion of individual mRNA molecules and protein complexes or post-translational modifications using padlock probes combined with the in situ proximity ligation assay. Nat Protoc. Feb. 2013;8(2):355-72.
Weibrecht et al., Proximity ligation assays: a recetn addition to the proteomics toolbox. Expert Rev of Proteomics. Jun. 2010;7(3):401-9.
Zhang et al., Dynamic DNA nanotechnology using strand-displacement reactions. Nat Chem. 2011;3(2):103-13.
Zhang et al., Optimizing the specificity of nucleic acid hybridization. Nat Chem. Epub Jan. 22, 2012, 7 pages.
Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.
U.S. Appl. No. 13/882,231, filed Jul. 1, 2013, Granted, U.S. Pat. No. 9,284,602.
U.S. Appl. No. 14/553,165, filed Nov. 25, 2014, Granted, U.S. Pat. No. 10,036,059.
U.S. Appl. No. 16/017,570, filed Jun. 25, 2018, Abandoned, 2018-0363045.
U.S. Appl. No. 17/169,145, filed Feb. 5, 2021, Pending.
U.S. Appl. No. 13/882,223, filed Jun. 11, 2013, Granted, U.S. Pat. No. 10,024,796.
U.S. Appl. No. 16/008,719, filed Jun. 14, 2018, Granted, U.S. Pat. No. 10,876,971[1].
U.S. Appl. No. 17/101,705, filed Nov. 23, 2020, Pending.
U.S. Appl. No. 15/622,261, filed Jun. 14, 2017, Published, 2017-0327888.
U.S. Appl. No. 15/999,245, filed Aug. 17, 2018, Published, 2019-0106733.
U.S. Appl. No. 16/464,170, filed May 24, 2019, Published, 2020-0362398[1].
U.S. Appl. No. 16/964,527, filed Jul. 23, 2020, Pending.
U.S. Appl. No. 17/040,041, filed Sep. 21, 2020, Published, 2021-0199731[1].
Douglas et al., Self-assembly of DNA into nanoscale three-dimensional shapes. Nature. May 21, 2009;459(7245):414-8. doi: 10.1038/nature08016.
Fiandaca et al., Self-reporting PNA/DNA primers for PCR analysis. Genome Res. Apr. 2001;11(4):609-13. doi: 10.1101/gr.170401.
Forster et al., A human gut bacterial genome and culture collection for improved metagenomic analyses. Nat Biotechnol. 2019;37(2):186?192. doi:10.1038/s41587-018-0009-7.
Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi: 10.3390/ijms14035765.
Jiang et al., Real-time detection of isothermal amplification reactions with thermostable catalytic hairpin assembly. J Am Chem Soc. May 22, 2013;135(20):7430-3 and Supporting Information, doi: 10.1021/ja4023978. Epub May 9, 2013.
Nazarenko et al., Multiplex quantitative PCR using self-quenched primers labeled with a single fluorophore. Nucleic Acids Res. May 1, 2002;30(9):e37(1-7). doi: 10.1093/nar/30.9.e37.
Simonsson et al., A substrate for telomerase. Trends Biochem Sci. Dec. 2003;28(12):632-8. doi: 10.1016/j.tibs.2003.10.005.
Tisza et al., Discovery of several thousand highly diverse circular DNA viruses. Elife. Feb. 4, 2020;9:e51971. doi: 10.7554/eLife.51971.
Extended European Search Report for Application No. EP 21183689.5, dated Feb. 24, 2022.
Choi et al., Programmable in situ amplification for multiplexed imaging of mRNA expression. Nat Biotechnol. Nov. 2010;28(11):1208-12. Epub Oct. 31, 2010.
Evanko, D. Hybridization chain reaction. Nat Methods. Dec. 2004;1:186.
Ge et al., A highly sensitive target-primed rolling circle amplification (TPRCA) method for fluorescent in situ hybridization detection of microRNA in tumor cells. Anal Chem. Feb. 4, 2014;86(3):1808-15. Epub Jan. 21, 2014.
Ke et al., Three-dimensional structures self-assembled from DNA bricks. Science. Nov. 30, 2012;338(6111):1177-83.
Nilsson et al., Real-time monitoring of rolling-circle amplification using a modified molecular beacon design. Nucleic Acids Res. Jul. 15, 2002;30(14):e66.
Nilsson, M. Lock and roll: single-molecule genotyping in situ using padlock probes and rolling-circle amplification. Histochem Cell Biol. Aug. 2006;126(2):159-64. Epub Jun. 29, 2006.
Urbaneck et al., Small RNA Detection by in Situ Hybridization Methods. Int J Mol Sci. Jun. 10, 2015;16(6):13259-86.
Wei et al., Complex shapes self-assembled from single-stranded DNA tiles. Nature. May 30, 2012;485(7400):623-6.
Yang et al., Regulation of DNA strand displacement using an allosteric DNA toehold. J Am Chem Soc. Oct. 26, 2016;138(42):14076-14082. Epub Oct. 13, 2016.
Zhang et al., Engineering entropy-driven reactions and networks catalyzed by DNA. Science. Nov. 16, 2007;318(5853):1121-5. Erratum in: Science. Dec. 18, 2009;326(5960):1633.
Zhao et al., Rolling circle amplification: applications in nanotechnology and biodetection with functional nucleic acids. Angew Chem Int Ed Engl. 2008;47(34):6330-7.
U.S. Appl. No. 16/334,643, filed Mar. 19, 2019, Pending.
U.S. Appl. No. 16/464,170, filed May 24, 2019, Pending.
PCT/US2019/015161, Jan. 25, 2019, Published, 2019/147945[1].
PCT/US2019/023371, Mar. 21, 2019, Published, 2019/183359[1].
EP 16744150.0, Jun. 25, 2018, Partial European Search Report.
EP 16744150.0, Sep. 25, 2018, Extended European Search Report.

\* cited by examiner

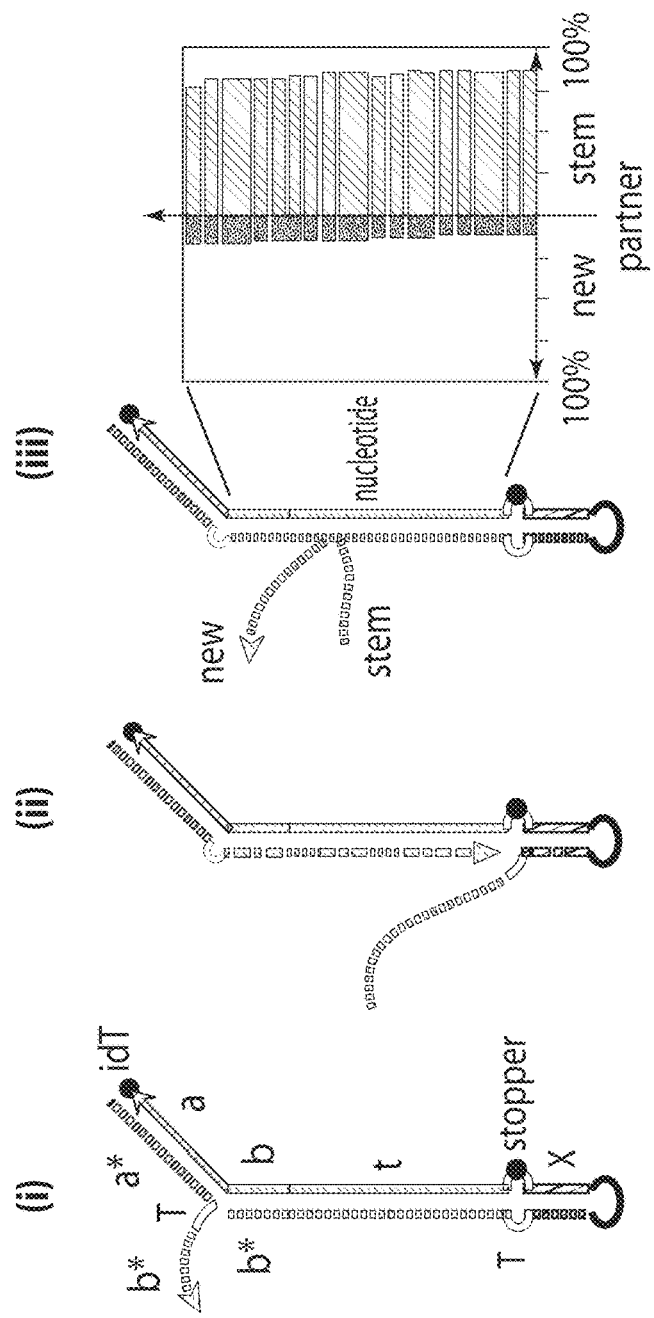
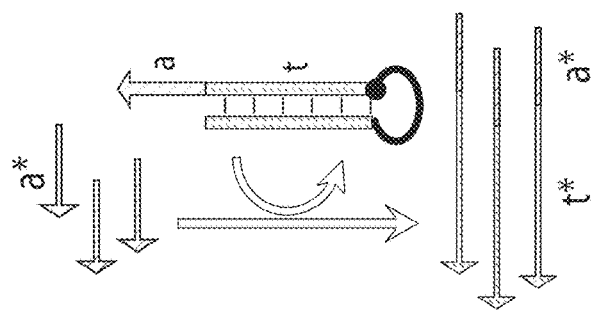
FIG. 3B
FIG. 3A (SEQ ID NO: 1-5, top to bottom)

| Universal primer | | Barcode i | Palindrome p | Barcode j* | | Universal primer* | |
|---|---|---|---|---|---|---|---|
| AGTC | AGCTCGAGCTAGGTC | T AGAGCTAGGCTATC | ACTAGT | GATAGCCTAGCTCT | A | GACCTAGCTCGAGCT | ACTT |
| AGTC | AGCTCGAGCTAGGTC | T TAGCGTAGGCTACA | ACTAGT | GCTAGCTAGGGAGC | A | GACCTAGCTCGAGCT | ACTT |
| AGTC | AGCTCGAGCTAGGTC | T AGCGCTATCCTAGCT | ACTAGT | ATCGTACTGTGACG | A | GACCTAGCTCGAGCT | ACTT |
| AGTC | AGCTCGAGCTAGGTC | T GATCTAGCGTAGCC | ACTAGT | AGGCTCTAGCGACT | A | GACCTAGCTCGAGCT | ACTT |
| AGTC | AGCTCGAGCTAGGTC | T AGGCTCTAGCTAGC | ACTAGT | CGATAGCTAGCGAA | A | GACCTAGCTCGAGCT | ACTT |

FIG. 3F chemically-synthesized
probe precursor precursor extended
by polymerase extended precursor
5' end cleaved
by 'USER' enzymes
(neb.com)

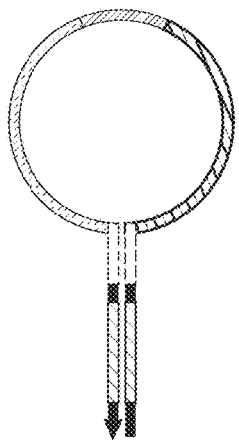

steps:
i. anneal records into haripins (two hairpins per dsDNA record)
ii. add 3'T overhang with Klenow or Taq pol
iii. ligate to A-overhang adapter pair ("A-tailing")

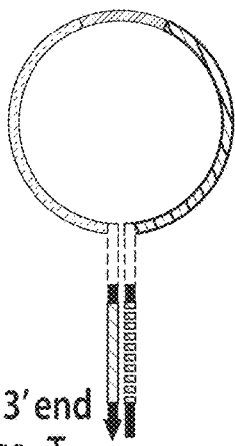

single T overhang added at 3' end by klenow or Taq polymerase=T

A
AS15 = ligation stem
EBC4 = optional 4nt experiment barcode
N5= random 5nt, sequencer-required sequencing adaters may be in separate strands or as hairpin sequencing adapters

FIG. 7B

```
            BC143 - BC288
(= protein A, #43 --- protein B, #64)
                 .
                 .
          BC983 - BC165
          BC049 - BC274
          BC657 - BC637
          BC970 - BC166
                 .
                 .
                 .
                 .
``` alternative: cut records with restriction endonucleases, then ligate via "sticky ends"

alternative: digestion of excess non-ligated record material with one or more exonucleases alternative: protect via adapter pair in closed hairpin, with optional polymerase block or cleavable linker

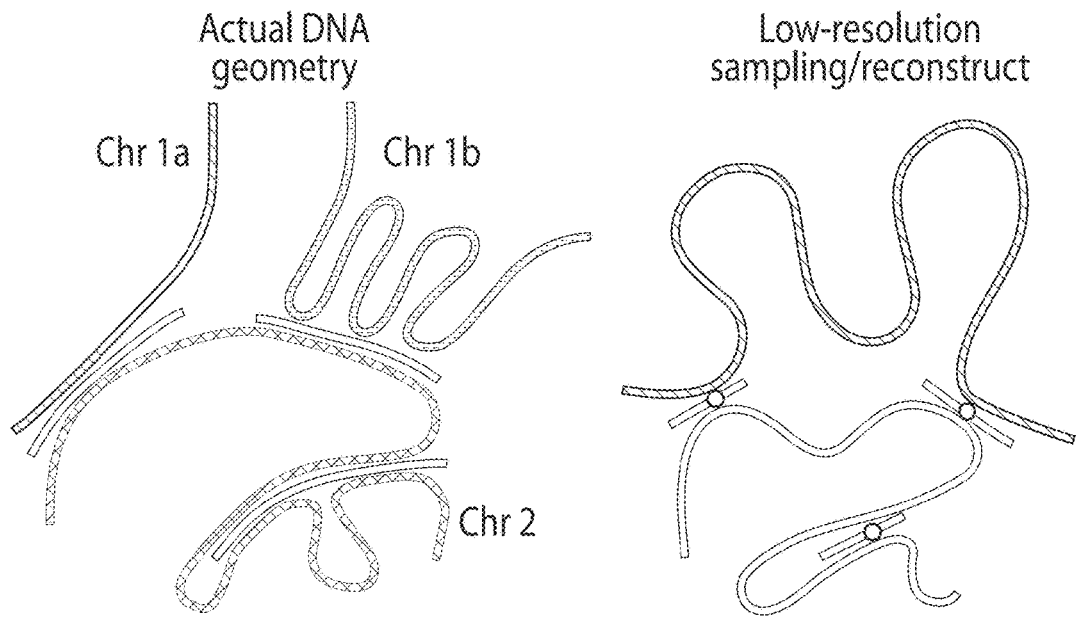
FIG. 16A
FIG. 16B
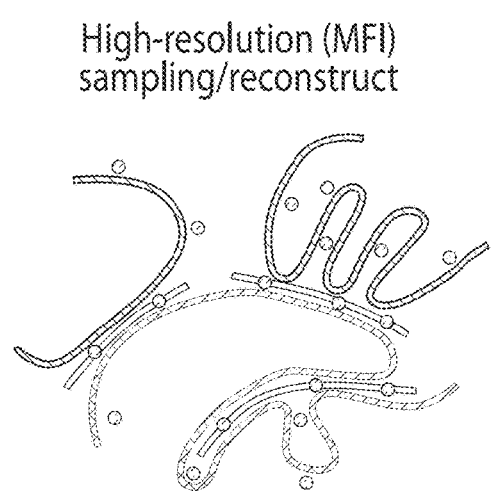
FIG. 16C
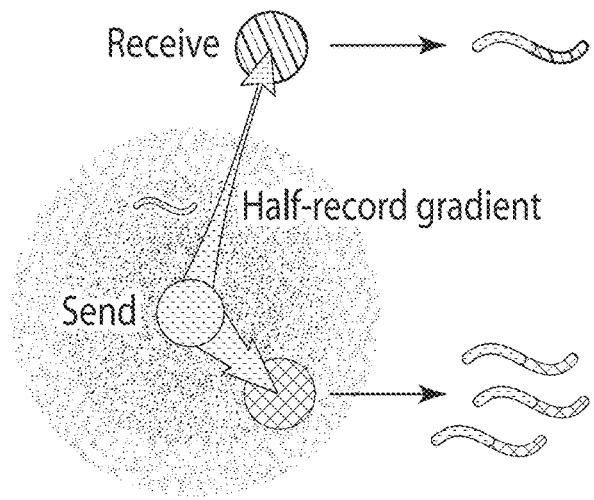
FIG. 17

MICROSCOPE-FREE IMAGING

RELATED APPLICATIONS

This application claims the benefit under 35 U.S.C. § 119(e) of U.S. provisional application No. 62/110,050, filed Jan. 30, 2015, which is incorporated by reference herein in its entirety.

FEDERALLY SPONSORED RESEARCH

This application is a national stage filing under 35 U.S.C. § 371 of international application number PCT/US2016/015503, filed Jan. 29, 2016, which claims the benefit under 35 U.S.C. § 119(e) of U.S. provisional application No. 62/110,050, filed Jan. 30, 2015, each of which is incorporated by reference herein in its entirety.

BACKGROUND OF INVENTION

Using a microscope to simultaneously image, at single molecule resolution, the relevant molecules of complex molecular systems of a living organism is challenging, particularly with respect to high-throughput and multiplexing analyses. Further, other techniques, such as co-immunoprecipitation and proximity ligation, often used to resolve molecular interactions, are inherently destructive, which prevents the repeat sampling required to elucidate individual molecular networks.

SUMMARY OF INVENTION

Provided herein, in some aspects, are methods of imaging molecules without a microscope or other specialized equipment. Such methods are referred to herein as "microscope-free imaging (MFI)" methods. Current imaging technologies use microscopes in a "top-down" approach to probe molecular targets. Herein, "molecular instruments" (e.g., DNA-based and protein-based molecules) are used, instead of microscopes, in a "bottom-up" approach for inspecting molecular targets. Methods of the present disclosure provide for higher spatial resolution (e.g., to visualize biological structures as well as true-connectivity and dynamics data within individual networks), greater multiplexing capabilities and higher throughput analyses relative to current microscopy imaging techniques. Further, methods of the present disclosure provide in situ access to molecular targets in their native states.

Some aspects of the present disclosure provide nucleic acid barcoded probes that include a nucleic acid arranged to form a hairpin structure having a partially-double-stranded primer-binding region, a double-stranded barcode region, a double-stranded palindromic region, and a single-stranded loop region containing a target-binding moiety, wherein a synthetic non-DNA linker that terminates polymerization is located between the double-stranded palindromic region and the loop region.

Some aspects of the present disclosure provide nucleic acid barcoded probes that include one or more nucleic acid strands arranged into (a) a double-stranded palindromic region, (b) a double-stranded barcode region, and (c) a primer-binding region.

In some embodiments, a nucleic acid barcoded probe comprises a first nucleic acid strand comprising a first palindromic sequence, a first barcode sequence and a primer-binding sequence, and a second nucleic acid strand comprising a second palindromic sequence that is complementary to and binds to the first palindromic sequence and a second barcode sequence that is complementary to and binds to the first barcode sequence, wherein the first nucleic acid strand and the second nucleic acid strand are attached to each other through a linker (e.g., a non-nucleic acid linker, or a contiguous stretch of nucleic acids) and are arranged into a double-stranded palindromic region, a double-stranded barcode region, and a partially double stranded (or single-stranded) primer-binding region (e.g., forms a hairpin loop structure, such as the structure shown in FIG. 5).

In some embodiments, a primer-binding region is single-stranded. In some embodiments, a primer-binding region is partially double-stranded.

In some embodiments, a double-stranded palindromic region has a length of 4 to 10 nucleotide base pairs. In some embodiments, a double-stranded barcode region has a length of 2 to 100 nucleotide base pairs. In some embodiments, a primer-binding region has a length of 4 to 40 nucleotides.

In some embodiments, a barcoded probe further comprises adjacent to the double-stranded palindromic region a molecule or modification that terminates polymerization. Two nucleic acid regions are considered "adjacent" to each other if they within 0 to 10 nucleotides of each other. In some embodiments, two regions are considered "immediately adjacent" to each other if there are no nucleotides between the two regions, e.g., the two regions are contiguous with one another.

In some embodiments, a barcoded probe further comprises adjacent to the double-stranded palindromic region a synthetic non-DNA linker that terminates polymerization. For example, a barcoded probe may further comprise adjacent to the double-stranded palindromic region a triethylene glycol spacer that terminates polymerization.

In some embodiments, a barcoded probe comprises a double-stranded displacement region adjacent to the molecule or modification that terminates polymerization. A double-stranded displacement region may have, for example, a length of 2 to 10 nucleotide base pairs.

In some embodiments, a barcoded probe is arranged to form a hairpin structure comprising a single-stranded loop region. A single-stranded loop region may have, for example, a length of 3 to 50 nucleotides.

In some embodiments, a barcoded probe further comprises a target-binding moiety. A target-binding moiety, in some embodiments, is attached to the single-stranded loop region.

In some embodiments, a target-binding moiety is selected from the group consisting of: biotin (e.g., as a binding partner to avidin or streptavidin), an antibody (or an antibody fragment, e.g., Fc fragment), an aptamer, a nanobody, a nucleic acid, a drug and an atom. An "aptamer" is oligonucleic acid or peptide molecule that binds to a specific molecular target. A DNA, RNA or XNA aptamer typically includes a short (e.g., 5 to 30 nucleotides) strands of oligonucleotides. A peptide aptamer typically includes a short variable peptide domain, attached at both ends to a protein scaffold. A "nanobody" is a single-domain antibody (also referred to as antibody fragment) that includes a single monomeric variable antibody domain and is able to bind selectively to a molecular target.

In some embodiments, a barcoded probe comprises at least one locked nucleic acid (LNA) nucleotide. A LNA may be located, for example, in or adjacent to the double-stranded barcoded region.

In some embodiments, a barcoded probe further comprises a single-stranded poly-T (or poly-A) end sequence (e.g., at the 3' end or the 5' end).

In some embodiments, a barcoded probe is bound to a molecular target through a target-binding moiety.

Some aspects of the present disclosure provide pluralities of nucleic acid barcoded probes, as provided herein.

In some embodiments, the double-stranded palindromic region is the same for each probe of the plurality.

In some embodiments, the double-stranded barcode region is unique to each probe of the plurality.

In some embodiments, a plurality comprises subsets of barcoded probes, each subset comprising a unique barcode region.

In some embodiments, the primer-binding region is the same for each probe of a plurality.

In some embodiments, the primer-binding region is unique for each subset of barcoded probes of a plurality.

In some embodiments, each probe of a plurality is bound to a molecular target through a target-binding moiety.

Some aspects of the present disclosure provide compositions that include a plurality of barcoded probes, as provided herein, and primer that is at least partially complementary to a primer-binding region of a probe of the plurality.

In some embodiments, a primer comprises at least one nucleotide mismatch relative to the primer-binding region.

In some embodiments, a primer comprises at least one artificial linker that is not complementary to and/or does not bind to the primer-binding region.

In some embodiments, compositions further comprise a strand-displacement polymerase. For example, compositions may comprise a strand-displacement polymerase selected from the group consisting of: Bsu DNA polymerase, large fragment; phi29 polymerase; Deep VentR polymerase; Klenow fragment polymerase; and modified Taq polymerase.

In some embodiments, compositions further comprise a helper nucleic acid strand that is partially complementary to the single-stranded primer binding region, is partially complementary to a single-stranded region adjacent to the primer binding region, and binds transiently to the single-stranded region adjacent to the primer binding region. In some embodiments, a helper strand has a length of 3 to 20 nucleotides.

Some aspects of the present disclosure provide methods of detecting molecular target interactions. In some embodiments, the methods include the steps of (a) combining in a single reaction the plurality of nucleic acid barcoded probes with (i) a primer complementary to the primer-binding region of a probe of the plurality and (ii) a strand-displacement polymerase, and (b) incubating the reaction under conditions that result in production of barcoded records.

In some embodiments, the barcoded records are double-stranded.

In some embodiments, the step of (b) comprises incubating the sample at physiological conditions. "Physiological conditions" encompasses a temperature range of 20-40 degrees Celsius (° C.) (e.g., 20-25° C., 20-30° C., 20-35° C., 25-40° C., 25-35° C., 25-30° C., 30-40° C., 35-40° C., or 37° C.), pH of 6-8 (e.g., pH 6, 6.5, 7, 7.5 or 8), sodium concentrations of 0-1 M (typically 145 mM), and magnesium concentration of 0-20 mM (e.g., 1-2 mM). Thus, in some embodiments, the step of (b) comprises incubating the sample at a temperature of 37° C. in a buffer containing magnesium at a concentration of 2 mM. In some embodiments, the buffer is commercially available, e.g., as "1× Thermo Pol Buffer" (New England Biolabs) or similar.

In some embodiments, the step of (b) comprises incubating the sample at a temperature of 37° C. (e.g., in a buffer containing 2 mM magnesium) for a time of 0.5 to 3.0 hours.

In some embodiments, nucleic acid barcoded probes of the plurality are regenerated following production of the double-stranded barcoded records.

In some embodiments, methods further comprise collecting barcoded records from the sample.

In some embodiments, the methods further comprise purifying barcoded records collected from the sample.

In some embodiments, the methods further comprise sequencing barcoded records collected from the sample, thereby producing sequencing data.

In some embodiments, the methods further comprise reconstructing from the sequencing data an image of molecular target interactions.

In some embodiments, the methods further comprise attaching the barcoded records to sequence-specific adapters.

In some embodiments, attaching the barcoded records to sequence-specific adapters comprises (i) dissociating double-stranded barcoded records into single-stranded barcoded records, (ii) self-annealing each single-stranded barcoded record to form a hairpin structure, and (iii) ligating each hairpin structure to an adapter sequence, thereby forming adaptor-barcoded records.

In some embodiments, the methods further comprise amplifying the adaptor-barcode records by polymerase chain reaction (PCR), thereby producing copies of the adaptor-barcode records.

In some embodiments, the methods further comprise purifying the copies of the adaptor-barcode records, thereby producing purified copies of the adaptor-barcode records.

In some embodiments, the methods further comprise sequencing the purified copies of the adaptor-barcode records, thereby determining the sequence of the barcoded records.

In some embodiments, the methods further comprise computationally processing the sequence of the barcoded records to produce a representative network of molecular target interactions. "Computationally processing" in the context of the present disclosure refers to the process by which nucleic acid sequences (e.g., of barcoded records) are processed using a computer and a model, e.g., understood and expressed as an algorithm or protocol.

In some embodiments, a primer include a first nucleic acid strand comprising a first sequence complementary to the single-stranded primer-binding region and a second sequence; and a second nucleic acid strand comprising a third sequence complementary to the single-stranded primer-binding region and a fourth sequence complementary to and bound to the second sequence, wherein the first and second nucleic acid strands are arranged into a double-stranded region flanked by single-stranded primer regions.

In some embodiments, the double-stranded region contains a barcode sequence.

In some embodiments, the primer further comprises at least one sequencing site or attachment site.

In some embodiments, the sample is a biological sample. For example, the biological sample may be a cell or cell lysate.

Some aspects of the present disclosure provide pairs of nucleic acid barcoded probes that include: (a) a first nucleic acid barcoded probe arranged into (i) a double-stranded barcode region, and (ii) a single-stranded primer-binding region, and (b) a second single-stranded barcoded probe comprising a barcode region and a primer region complementary to the single-stranded primer-binding region.

In some embodiments, the double-stranded barcode region of the first nucleic acid barcoded probe has a length of 5 to 50 nucleotide base pairs.

In some embodiments, the single-stranded primer-binding region of the first nucleic acid barcoded probe has a length of 4 to 50 nucleotides.

In some embodiments, the barcode region of the second nucleic acid barcoded probe has a length of 5 to 50 nucleotides.

In some embodiments, the primer region of the second nucleic acid barcoded probe has a length of 4 to 50 nucleotides.

In some embodiments, the first nucleic acid barcoded probe further comprises adjacent to the double-stranded barcode region a molecule or modification that terminates polymerization. For example, the first nucleic acid barcoded probe may further comprise adjacent to the double-stranded barcode region a synthetic non-DNA linker that terminates polymerization.

In some embodiments, the first nucleic acid barcoded probe comprises a double-stranded displacement region adjacent to the molecule or modification that terminates polymerization.

In some embodiments, the double-stranded displacement region has a length of 2 to 10 nucleotide base pairs.

In some embodiments, the first nucleic acid barcoded probe is arranged to form a hairpin structure comprising a single-stranded loop region. In some embodiments, the single-stranded loop region has a length of 3 to 50 nucleotides. In some embodiments, the single-stranded loop region contains the single-stranded primer-binding region of (ii).

In some embodiments, the first nucleic acid barcoded probe and/or the second nucleic acid barcoded probe further comprise(s) a target-binding moiety. In some embodiments, the target-binding moiety is located at an end distal to the single-stranded primer-binding region of the first nucleic acid barcoded probe and/or at an end distal to the primer region of the second nucleic acid barcoded probe. In some embodiments, the target-binding moiety is selected from the group consisting of: biotin, an antibody, an aptamer, a nanobody and a nucleic acid.

In some embodiments, the first nucleic acid barcoded probe and the second nucleic acid barcoded probe each is bound to a molecular target through a target-binding moiety.

Some aspects of the present disclosure provide compositions that include a pair of nucleic acid barcoded probes, as provided herein, and a third nucleic acid barcoded probe arranged into a double-stranded barcode region, and a single-stranded primer-binding region, wherein the single-stranded primer-binding region is complementary to and binds to the primer region of the second nucleic acid barcoded probe.

In some embodiments, the third nucleic acid barcoded probe further comprises a target-binding moiety. In some embodiments, the third nucleic acid barcoded probe is bound to a molecular target through a target-binding moiety is bound to a molecular target.

Some aspects of the present disclosure provide compositions that include a pair of nucleic acid barcoded probes, as provided herein, and a strand-displacement polymerase.

In some embodiments, the strand-displacement polymerase selected from the group consisting of: Bst large fragment polymerase, phi 29 polymerase, Deep VentR polymerase, Klenow fragment polymerase, and modified Taq polymerase.

Some aspects of the present disclosure provide methods of detecting molecular target interactions that includes the steps of (a) combining in a single reaction a pair of nucleic acid barcoded probes, as provided herein, and a strand-displacement polymerase, and (b) incubating the reaction under conditions that result in production of single-stranded barcoded records.

Some aspects of the present disclosure provide methods of detecting molecular target interactions that includes the steps of combining in a single reaction (a) two single-stranded nucleic acid barcoded probes, each comprising a palindromic sequence, a barcode sequence and a primer-binding sequence, wherein the barcodes sequences are different from each other, and wherein each barcoded probe is attached to a molecular target, (b) a partially double-stranded primer arranged into a double-stranded region flanked by 3' single-stranded flanking regions that each contain a primer complementary to the primer-binding sequence, wherein the double-stranded region contains a reversible covalent binding site; and a strand-displacing polymerase; incubating (a) and (b) under conditions sufficient to permit binding of the primers to the primer-binding sites and extension of each 3' flanking region of the primers; and heating the reaction to a temperature of at least 50° C. to permit dissociation of the primers from the two single-stranded nucleic acid barcoded probes, thereby regenerating (a) and (b).

BRIEF DESCRIPTION OF DRAWINGS

The accompanying drawings are not intended to be drawn to scale. For purposes of clarity, not every component may be labeled in every drawing.

FIG. 3A shows a schematic overview of the autocyclic copy-and-release of an example of a hairpin-encoded DNA template domain t onto multiple copies of primer strand a, producing sequences a*-t*. FIG. 3B shows an example mechanism of initial primer binding (i), extension (ii), and random walk of the strand displacement branch (iii), with computationally-predicted relative association probabilities shown for each template nucleotide. Domain lengths may be, for example, 6-20 nucleotides (a), 5 nucleotides (b), 0-30 nucleotides (t), and 5 nucleotides (x). Complementary domains are shown in dotted lines. FIG. 3F shows sequencing data for different DNA records generating using the probes and method of FIG. 3A.

FIG. 4A shows an example of a chemically-synthesized probe precursor (A6=AAAAAA; U=deoxyuridine; a16=U/CAT/U/CCCAGC/U/TAC/U (SEQ ID NO: 7); ax5=CTCAC; H22=random 22-nucleotide combination of A, C and/or T; T=thymidine; DS6=CGCTGG; spacer 9=(Integrated DNA Technologies) "iSp9"; p6=ACCGGT; Probe precursor sequence: AAAAAA/U/CAT/U/CCCAGC/U/TAC/U/CTCACHHHHHHHHHHHHHHHHHHHHHHA CCGGTTCGCTGGTT/iBiodT/TTCCAGCG/iSp9/ACCGGT (SEQ ID NO:6)). FIG. 4B shows the probe precursor of FIG. 4A extended by polymerase (BCi20=barcode sequence). FIG. 4C shows the extended probe precursor of FIG. 4B having its 5' end cleaved by 'USER' enzymes (New England Biolabs).

FIGS. 7A-7C show an example of a method of processing DNA records of the present disclosure. The records are collected in supernatant (FIG. 7A) and ligated to sequencing-specific "adapters" (FIG. 7B). Then, several rounds of PCR are completed (FIG. 7C). Alternatively, records may be copied before adapters added, using a variety of standard methods, ultimately resulting in many copies of each original record, each with adapter sequences.

FIG. 9A shows an example of an auto-cycling probe having a simple "distal loop" region. FIG. 9B shows an example of an auto-cycling probe having a locked nucleic acid (LNA). FIG. 9C shows an example of an auto-cycling probe having a covalent linkage or other linker instead of a stem or loop. FIG. 9D shows an example of an auto-cycling probe having a primer weakened by a bulge, weak match, or mismatch. FIG. 9E shows an example of an auto-cycling probe having a stronger palindromic or other 'p' sequence. FIG. 9F shows an example of an auto-cycling probe having a dynamic "helper" dissociation strand comprised of either end of the probe, the record itself, or as a third strand (shown). FIG. 9G shows an example of an auto-cycling double-ended or looped probe having two competitors.

FIGS. 16A-16C show an example application of a microscope-free imaging method of the present disclosure to nucleome organization. Gray strokes indicate chromosomes interactions (FIG. 16A). FIG. 16B shows that chromosome copies sampled at low resolution (dots) are not differentiated, and reconstitution of interactions is poor. FIG. 16C shows that, at high resolution (dots), critical interactions and chromosome copy are evident using microscope-free imaging. Interactions between DNA and RNA or protein are also accessible by microscope-free imaging at this resolution (not depicted).

FIG. 17 shows an example of a longer-range microscope-free imaging of the present disclosure.

FIG. 20B shows a PCR amplification and denaturing PAGE gel of a recording from active probe, after intermediate wash, and recording from inactive probe. The intermediate wash result ensures there are no leftover records. A single set of nanostructures was used for all steps and re-sampled.

DETAILED DESCRIPTION OF INVENTION

Living organisms are complex molecular systems. Imaging provides a natural and direct way to investigate such systems and has emerged as a central method for biological study. An ideal way to study such systems is to simultaneously visualize all the relevant molecules in their native state with single molecule resolution. One way to visualize biological systems is by microscope, although using microscopes to image the molecular world poses several challenges, including "blurred vision," partial "color blindness," limited throughput, and restricted sample access. In a crowded population of molecules that dynamically reconfigure, it is difficult to clearly visualize single molecules, which leads to "blurred vision"; only a small number of different colors (e.g., 3 or 4) can used to simultaneously track multiple distinct molecules, which results in partial "color blindness"; microscopes have a limited visual field, permitting observation of only a small population of selected molecules in selected regions, thereby limiting throughput; and it is difficult to clearly visualize molecules in their native living state, particularly because molecules (e.g., as components of a biological sample) are often taken out of their biological context and processed to fit the particular observing platform of the microscope (e.g., in a thin fixed or frozen specimen slice).

Figure 1:
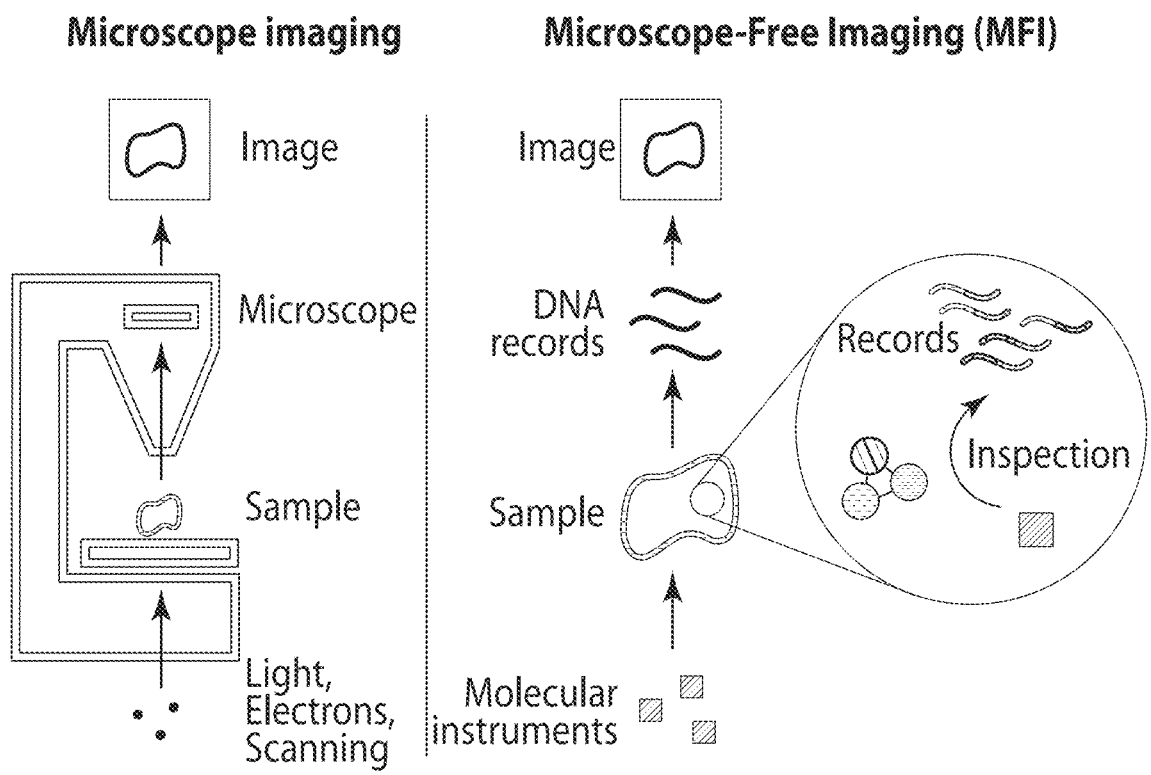
FIG. 1 shows a schematic comparison of microscope imaging and an example of microscope-free imaging of the present disclosure.

Thus, there is a need for an alternative to microscopy for imaging molecular interactions of complex biological systems. Provided herein, in some aspects, are microscope-free imaging (MFI) methods and related compositions directed to a "bottom-up" analysis of large populations of molecular targets, each linked to a unique nucleic acid barcoded probe, referred to herein as "barcoded targets" (see, e.g., FIGS. 1 and 2A). For example, when barcoded targets are proximate to each other, nucleic acid records (referred to herein simply as "records") of the spatial configuration of the barcoded targets (e.g., the proximity and/or arrangement of barcoded targets relative to each other) are created repeatedly, without destroying the barcoded targets. Thus, over time, as barcoded targets change their spatial configuration (e.g., interact with different barcoded targets), records of these changes are generated. The records are later read by, for example, high-throughput nucleic acid sequencing, and images of the underlying molecular targets are computational reconstructed. Two molecular targets are considered to be "proximate" to each other if, for example, they physically or chemically interact with or otherwise associate with each other. Two molecular targets are also considered to be "proximate" to each other if the distance between the two targets is 0 nanometer (nm) to 100 nm (or 0 nucleotide (nt) to 100 nt). For example, the distance between two targets proximate to each other may be 0 nm to 5 nm, 0 nm to 10 nm, 0 nm to 20 nm, 0 nm to 30 nm, 0 nm to 40 nm, or 0 nm to 50 nm.

The present methods and compositions provide, in some embodiments, a platform to image at high spatial resolution, with multiplexing capability, dynamic processes of single molecular targets (or, alternatively, a single species of molecular targets) in situ in a massively parallel manner, enabling high-throughput molecular imaging. Advantageously, microscope-free imaging, as provided herein, avoids harsh and damaging sample processing while permitting ultra-high resolution, precise computational production of images of molecular structures, digital molecular calculations, analyses of interaction stoichiometry and state distribution, and true connectivity and dynamics data obtained from individual molecular networks.

Figure 2A:
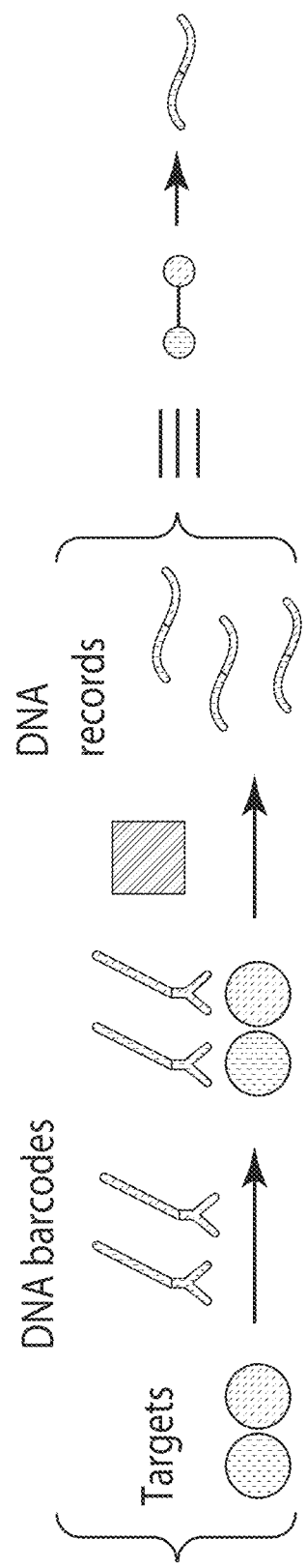
FIG. 2A shows a simplified overview of DNA barcoding of molecular targets and subsequent DNA recordation of target proximity relative to one another.
Figure 2B:
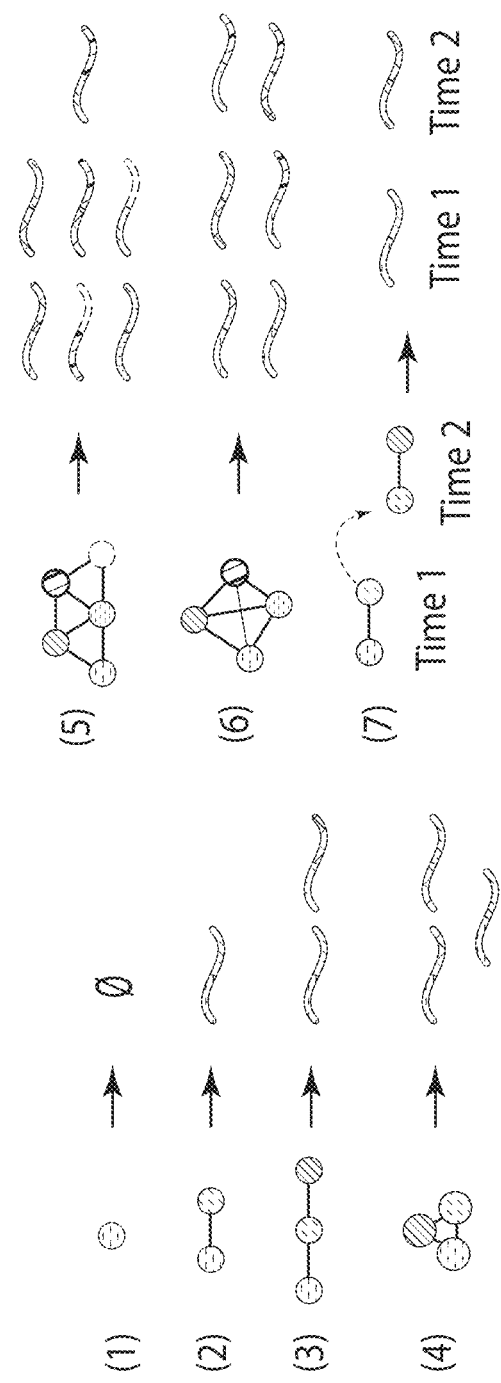
FIG. 2B, panels (1)-(7), show schematics of DNA records indicative of molecular target proximity and geometry.
Figure 2C:
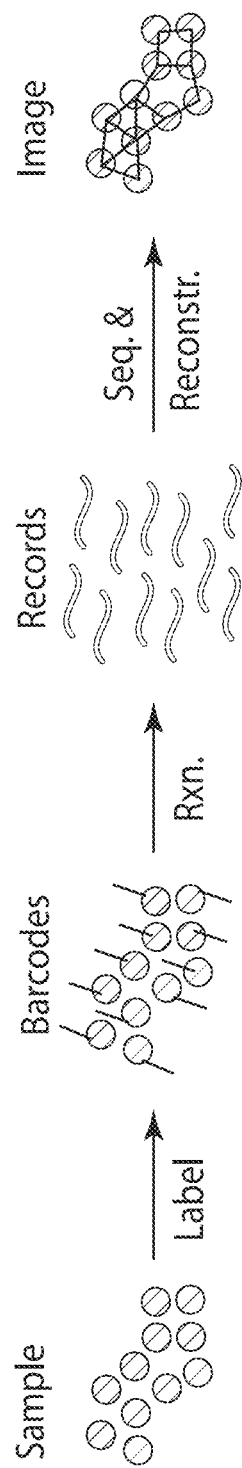
FIG. 2C shows a simplified overview of one example of a microscope-free imaging method of the present disclosure.

The methods provided herein use a nucleic acid (e.g., a DNA, such as a random DNA) "barcode" to uniquely label each molecular target of interest (FIG. 2A). When two barcoded targets are proximate to each other, a record encoding the identities of both barcodes is generated autonomously. For an isolated barcoded target (that is, a barcoded target that is not proximate to another barcoded target), no record is generated (FIG. 2B(1)). For a proximate pair of barcoded targets, a record unique to the pair is generate (FIG. 2B(2)), while for three proximate barcoded targets, two records are generated, each record unique to a single pair of the three barcoded targets (FIG. 2B(3)). Likewise, for more complex spatial configurations, multiple records are generated, each record unique to each pair of the complex configuration (FIGS. 2B(5) and 2B(6). In this manner, precise interconnectivity and, by inference, overall geometry can be recorded. Further, for dynamic configurations, records in proportion to association times are generated and, in some instances, may be time-stamped (FIG. 2B(7)). A summary of an example of a microscope-free imaging method, as provided herein, is schematize in FIG. 2C. Each molecular target in a sample is labeled with a unique barcode, repeat and continuous molecular reconfigurations (e.g., associations/interactions) autonomously produce records, and the records are read using high-throughput sequencing, followed by image production by computational reconstruction of the dynamic molecular target reconfigurations. The terms "reconfigure" and "reconfiguration," as used herein, refer to a change in positions of molecular targets relative to each other over time. For example, at time 1, three molecular targets may be arranged into a linear configuration, and at time 2, the three molecular targets may be arranged in a triangular configuration. The three molecules have thus "reconfigured" at time 2, relative to time 1.

Figure 3C:
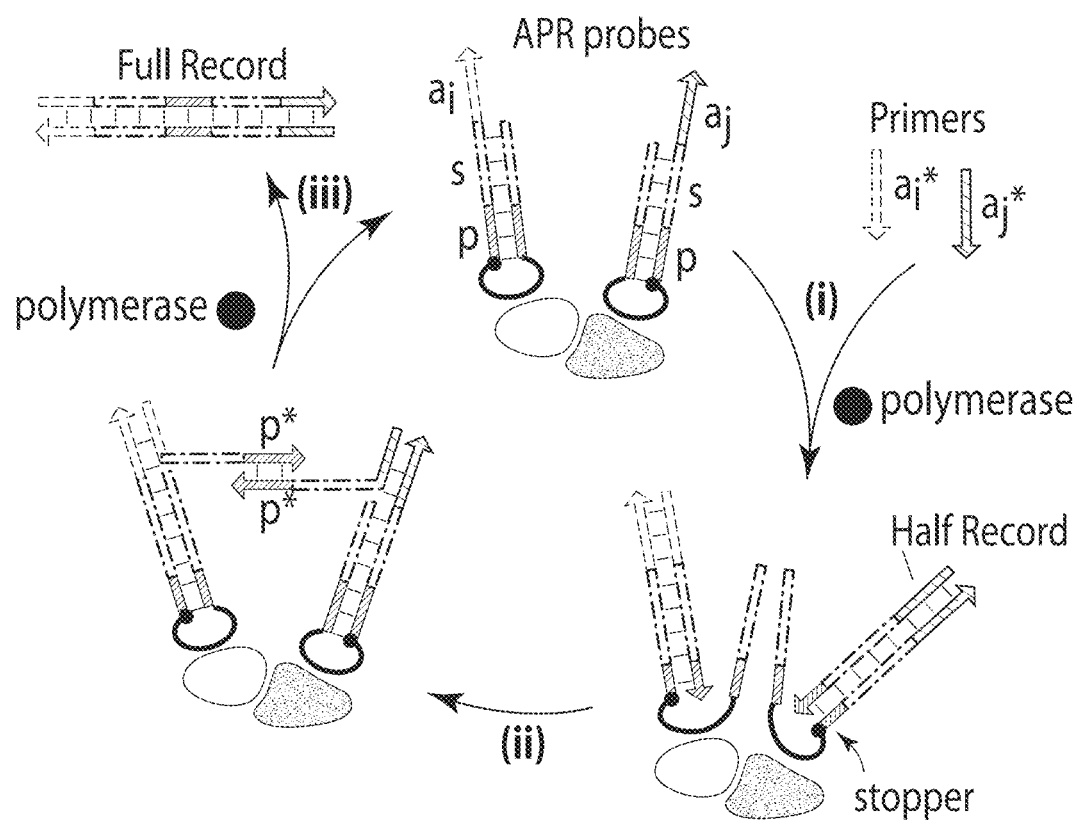
FIG. 3C shows a schematic of an example of an "auto-cycling" microscope-free imaging method of the present disclosure, also referred to as "auto-cyclic proximity recording" or "APR." An APR cycle, in this example, applies pairs of primer exchange hairpins as probes, with individual extension to bound half records (i), strand displacement and 3' palindromic domain hybridization (ii), and half-record extension to full records (iii).

Microscope-free imaging of the present disclosure is based on an "autocycle" reaction. This repetitive autocycling (e.g., repeated probe and target generation) limits aberrantly-produced records (e.g., those formed in solution) to one-copy, which can be easily discarded. Typically, but not always, the reaction takes place at 37° C. in the presence of a displacing polymerase. The barcodes used to identify single molecular targets are incorporated into nucleic acid probes (referred to herein as "nucleic acid barcoded probes" or simply "barcoded probes"), which are linked to molecular targets, in some embodiments, through a target binding moiety (e.g., biotin, an antibody, an aptamer, a nanobody or a nucleic acid). The barcoded probes are designed such that in the presence of a displacing polymerase and a universal, soluble primer, the barcoded probes direct an auto-cyclic process that repeatedly produces records of proximate barcodes. FIG. 3A depicts an example of a molecular mechanism underlying methods of the present disclosure. In step (1), a soluble universal u* primer binds each probe at a common single-stranded primer-binding u region, and a displacing polymerase extends the primer through the barcode (i or j) region and a palindromic p region to a molecule or modification that terminates polymerization (e.g., a synthetic non-DNA linker), thereby generating a "half-record," which refers to a newly generated nucleic acid strand containing a universal u* primer, a barcode (i or j) and a palindromic p* sequence (e.g., u*-i*-p* or u*-j*-p*). Note that a letter with a superscript "*" denotes a sequence complementary to the sequence represented by the corresponding letter without the "*." In step (2), half-records are partially displaced from the barcoded probe by a "strand displacement" mechanism (see, e.g., Yurke et al., *Nature* 406: 605-608, 2000; and Zhang et al. *Nature Chemistry* 3: 103-113, 2011, each of which is incorporated by reference herein), and proximate half-records hybridize to each other through the 3' palindromic regions p*. In step (3), the half-records are extended through the barcode (i and j) regions and primer-binding u regions, releasing soluble, full records that encode both barcode (i and j) probes. The barcoded probes are "regenerated" and able to undergo additional cycles in the same or other molecular target pairings. Upon termination of the cycling reaction, records are collected, prepared, and sequenced by, for example, massively parallel next generation sequencing techniques. Sequence data represent spatial configurations and, in some instances, connectivities/interactions, of molecular targets, ready for statistical analysis and image reconstruction.

"Strand displacement" refers to the mechanism by which two nucleic acid strands with identical sequences, when proximate to a single complementary nuclei acid strand (or segment of a strand), undergo relatively rapid (e.g., timescale<1s) competition for that complement strand, 'displacing' each other from the complement presumably by a 'random-walk' mechanism.

Barcoded Probes

Figure 5A:
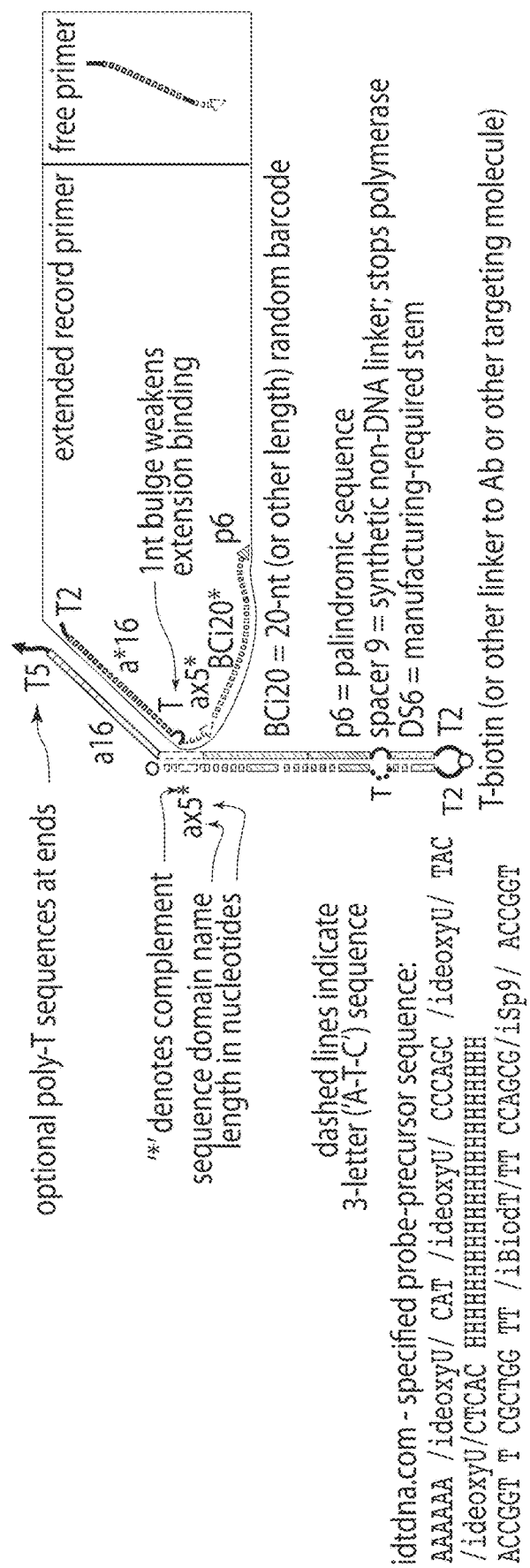
FIG. 5A shows additional details of the probe depicted in FIG. 4C, including the full probe precursor sequence (SEQ ID NO:6).
Figure 5B:
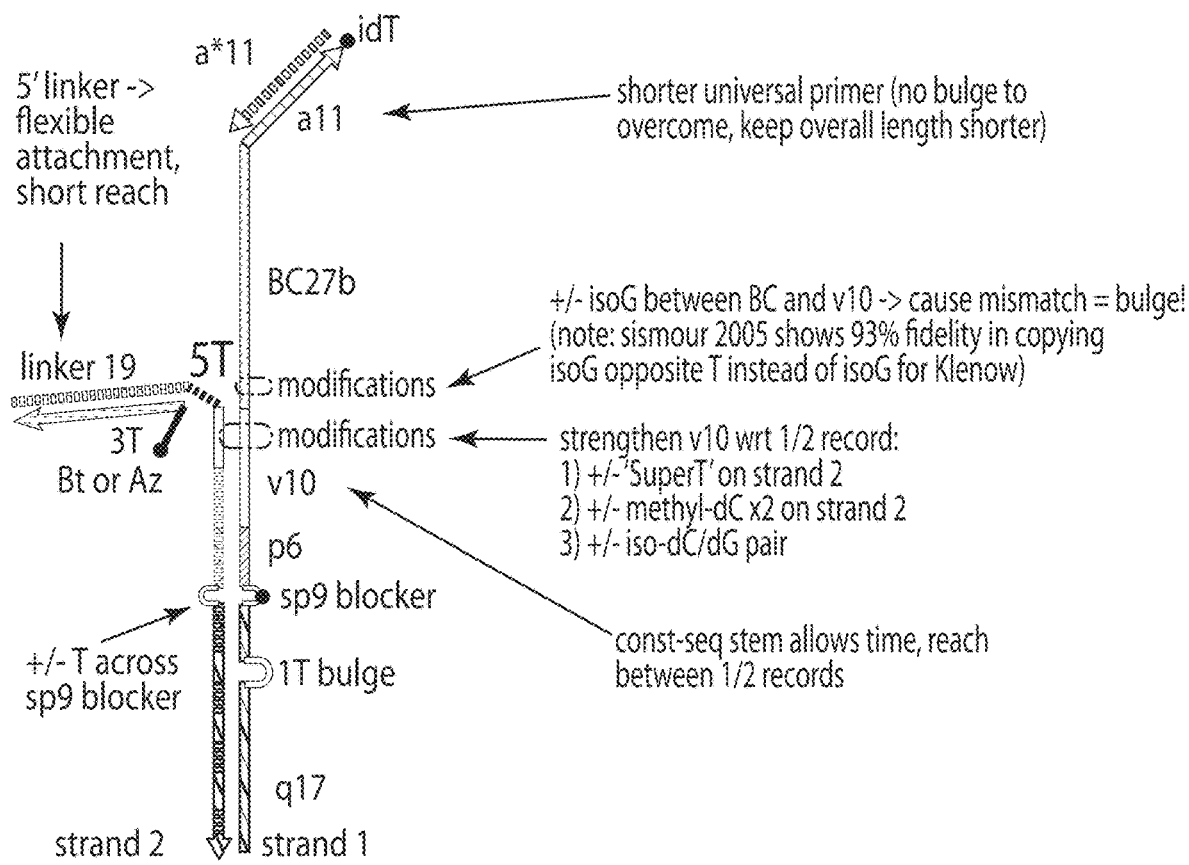
FIG. 5B shows an example of a truncated probe having a 5' end attachment (linker), two features that decrease the maximum distance at which proximity is detected to as few as 6 nm.
Figure 6A:
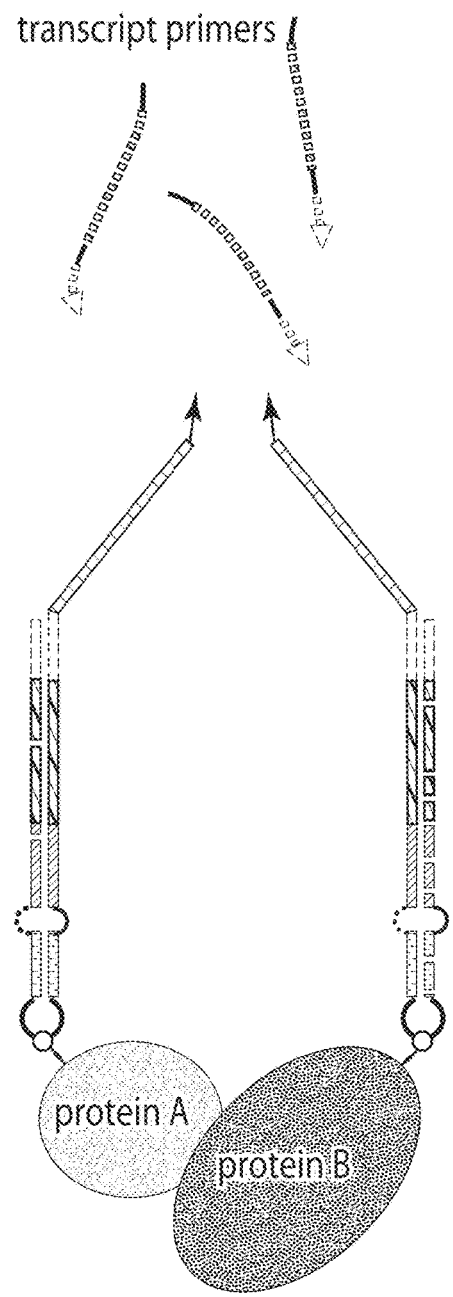
FIGS. 6A-6D show an example of a method of producing a DNA record of the present disclosure. Probes are bound to targets and soluble record primers are added (FIG. 6A). Primers bind and barcodes are copied by displacing the polymerase (FIG. 6B). Two extended records are automatically displaced from the probe and hybridize at palindromic 3' ends (FIG. 6C). The same polymerase extends the records through the second barcode and displaces the records from the probes (FIG. 6D). Example reaction conditions: buffer— 1× Bst buffer in water; polymerase—Bst, with alternate phi29 or other displacing polymerase; temperature—37° C.; time—0.5 to 3 hours, or more.
Figure 6B:
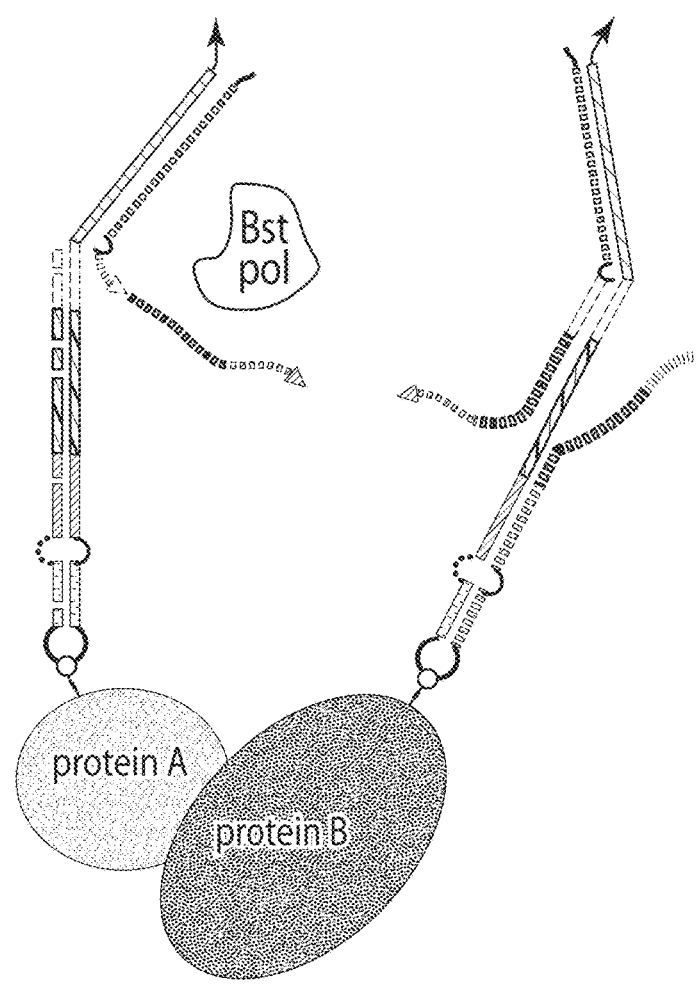
Figure 6C:
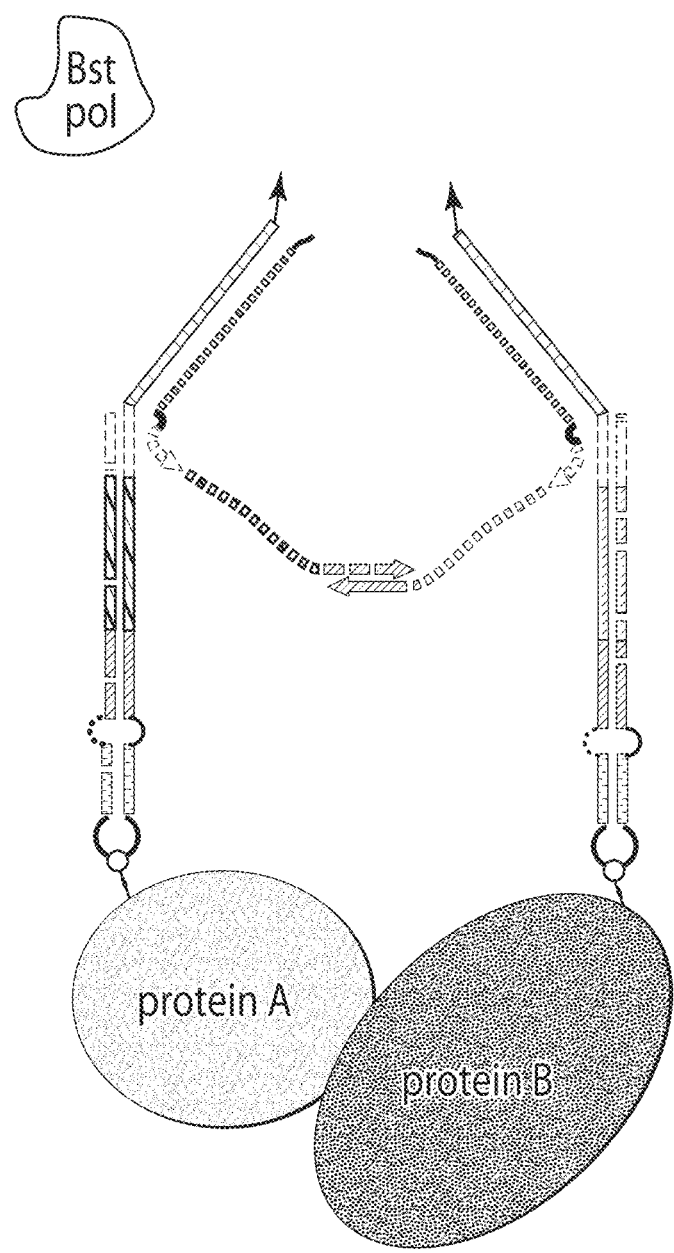
Figure 6D:
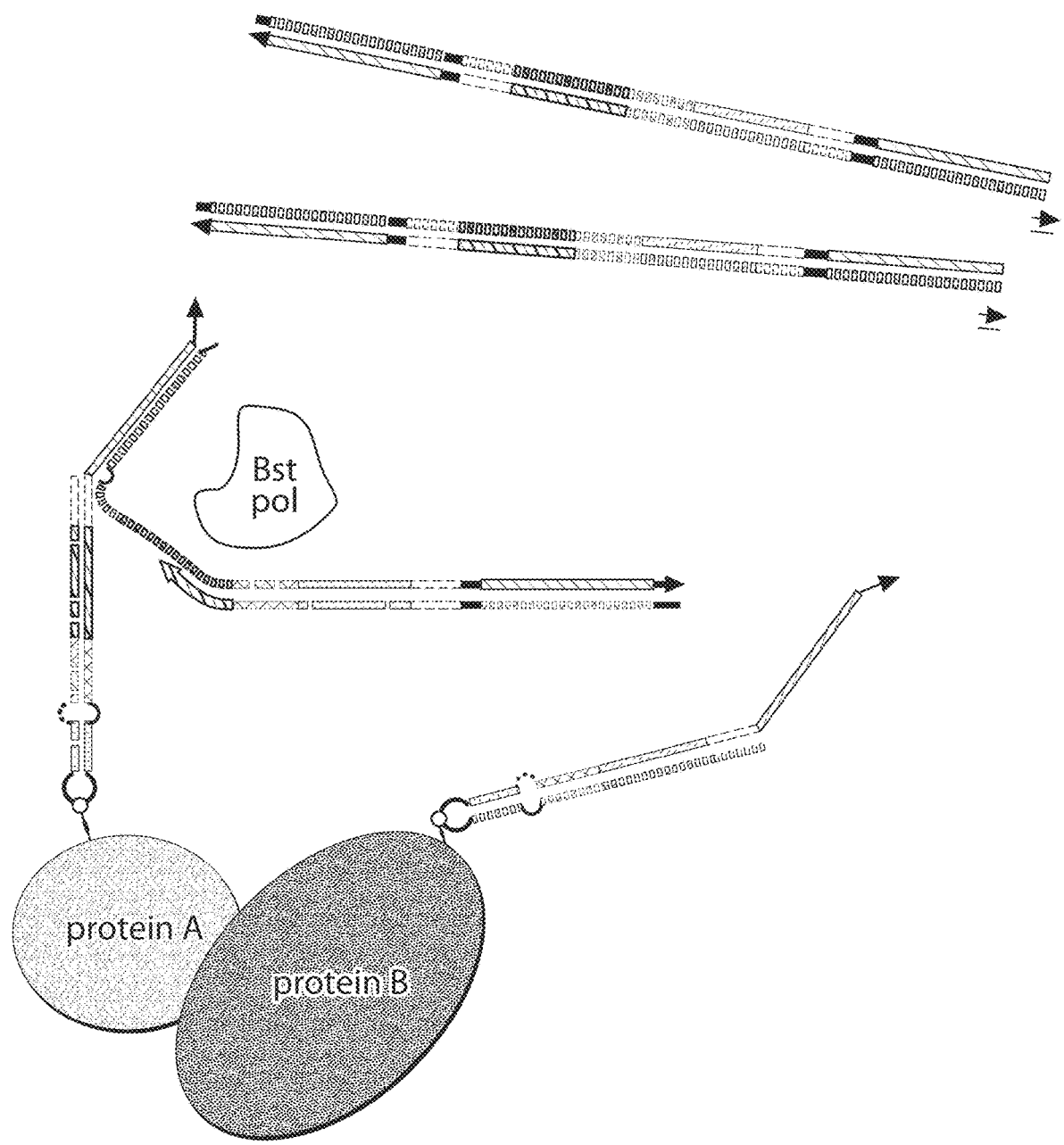
Figure 7A:
Figure 7C:
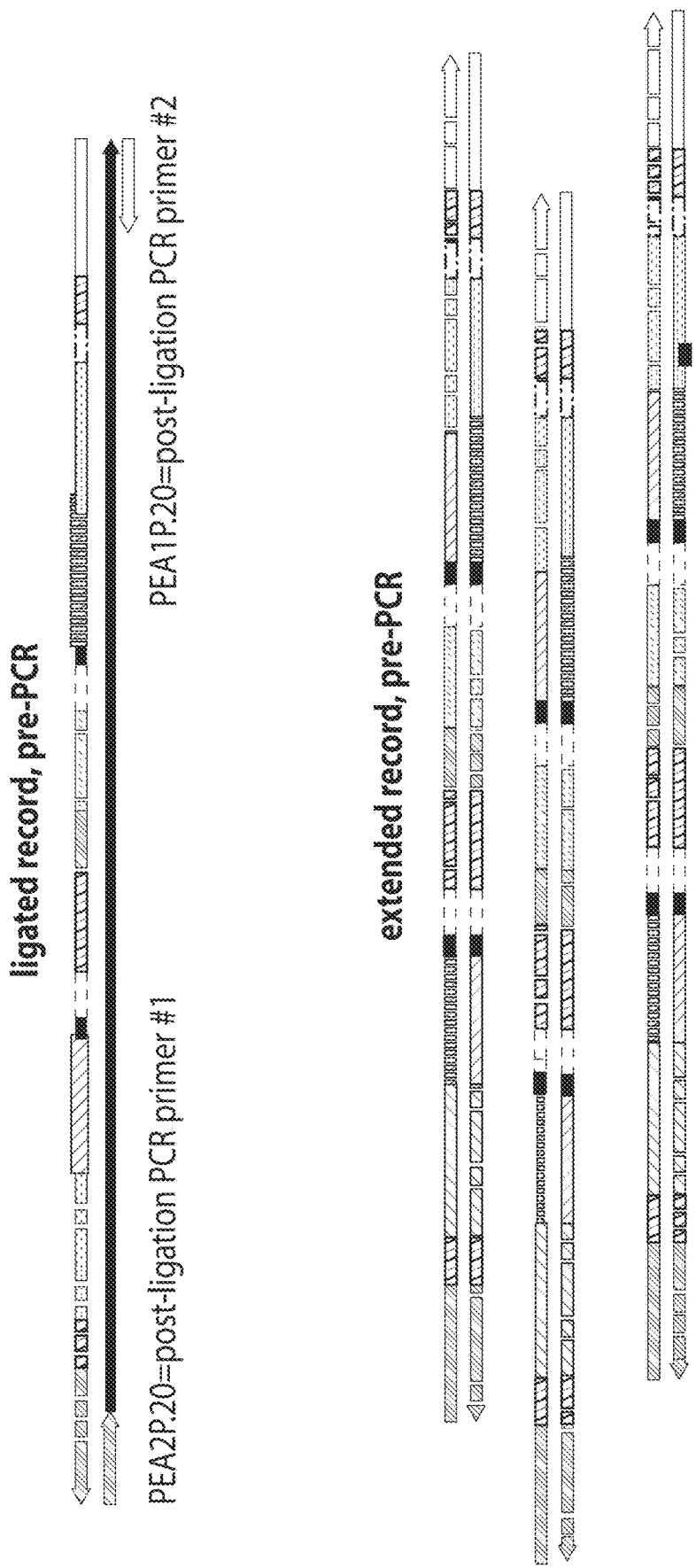
Figures 8A, 8B:
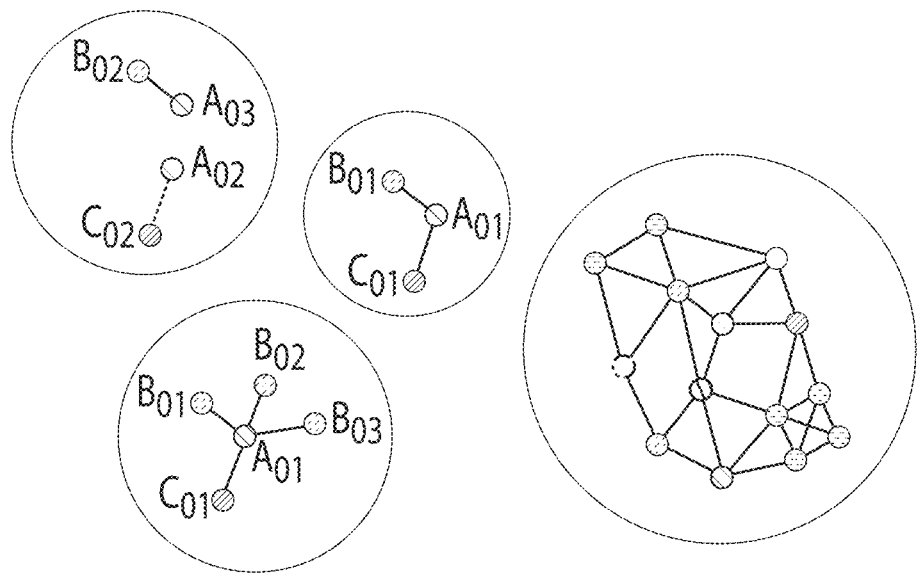
FIGS. 8A-8B show an example of a method of reading DNA records and a reconstruction processes. Records are gel- or column-purified and sequenced (e.g., by Next-Generation Sequencing) (FIG. 8A). The results are then processed computationally for network extraction (FIG. 8B).

Nucleic acid barcoded probes of the present disclosure, in some embodiments, comprise one or more nucleic acid strands arranged into a double-stranded palindromic region, a double-stranded barcode region, and a primer-binding region. In some embodiments, the barcoded probes are arranged to form a hairpin structure, which is a single stretch of contiguous nucleotides that folds and forms a double-stranded region, referred to as a "stem," and a single-stranded region, referred to as a "loop." The double-stranded region is formed when nucleotides of two regions of the same nucleic acid base pair with each other (intramolecular base pairing). An example of a barcoded nucleic acid hairpin is depicted in FIG. 5.

Nucleic acid barcoded probes of the present disclosure, in some embodiments, comprise a two parallel nucleic acid strands (e.g., as two separate nucleic acids or as a contiguous folded hairpin). One of the strands is referred to as a "complementary strand," and the other strand is referred to as a "displacement strand." The complementary strand typically contains the primer-binding region, or at least a single-stranded segment of the primer-binding region, where the primer binds (e.g., hybridizes). The complementary strand and the displacement strand are bound to each other at least through a double-stranded barcoded region and through a double-stranded palindromic region. The "displacement strand" is the strand that is initially displaced by a newly-generated half-record, as described herein, and, in turn, displaces the newly-generated half-record as the displacement strand "re-binds" to the complementary strand.

Two nucleic acids or two nucleic acid regions are "complementary" to one another if they base-pair, or bind, to each other to form a double-stranded nucleic acid molecule via Watson-Crick interactions (also referred to as hybridization). As used herein, "binding" refers to an association between at least two molecules due to, for example, electrostatic, hydrophobic, ionic and/or hydrogen-bond interactions under physiological conditions.

A "double-stranded region" of a nucleic acid refers to a region of a nucleic acid (e.g., DNA or RNA) containing two parallel nucleic acid strands bound to each other by hydrogen bonds between complementary purines (e.g., adenine and guanine) and pyrimidines (e.g., thymine, cytosine and uracil), thereby forming a double helix. In some embodiments, the two parallel nucleic acid strands forming the double-stranded region are part of a contiguous nucleic acid strand. For example, as discussed above, the present disclosure provides nucleic acid barcoded probes in the form of hairpin structures (e.g., FIG. 5).

A "single-stranded region" of a nucleic acid refers to a region of a nucleic acid containing a single nucleic acid strand, unbound to (unpaired with) a second nucleic acid strand. It should be understood that a barcoded probe in the form of a hairpin structure contains both a double-stranded region (a paired region), referred to as the "stem," and a single-stranded region (an unpaired region), referred to as the "loop," as discussed above.

A "double-stranded palindromic region" refers to a region of a nucleic acid (e.g., DNA or RNA) barcoded probe that is the same sequence of nucleotides whether read 5' (five-prime) to 3' (three prime) on one strand or 5' to 3' on the complementary strand with which it forms a double helix. For example, the following sequence, shown in FIG. 5, is considered a palindromic sequences: ACCGGT. Thus, a double-stranded palindromic region containing the foregoing sequence is arranged, as follows:

```
5'-ACCGGT-3'
3'-TGGCCA-5';
```

As shown in FIG. 3A, palindromic (p*) sequences permit joining of barcoded probes (and indirectly, barcoded targets) that are proximate to each other. Polymerase extension of a primer bound to the primer-binding region produces a "half-record," which refers to the newly generated nucleic acid strand. Generation of the half record displaces one of the strands of the barcoded probe, referred to as the "displacement strand." This displacement strand, in turn, displaces a portion of the half record (by binding to its "complementary strand"), starting at the 3' end, enabling the 3' end of the half record, containing the palindromic sequence, to bind to another half record similarly displaced from a proximate barcoded nucleic acid.

In some embodiments, a double-stranded palindromic region has a length of 4 to 10 nucleotide base pairs. That is, in some embodiments, a double-stranded palindromic region may comprise 4 to 10 contiguous nucleotides bound to 4 to 10 respectively complementary nucleotides. For example, a double-stranded palindromic region may have a length of 4, 5, 6, 7, 8, 9 or 10 nucleotide base pairs. In some embodiments, a double-stranded palindromic region may have a length of 5 to 6 nucleotide base pairs. In some embodiments, the double-stranded palindromic region is longer than 10 nucleotide base pairs. For example, the double-stranded palindromic region may have a length of 4 to 50 nucleotide base pairs. In some embodiments, the double-stranded palindromic region has a length of 4 to 40, 4 to 30, or 4 to 20 nucleotide base pairs. In some embodiments, the palindromic region may be replaced with an arbitrary sequence complementary to that produced by another probe. In such embodiments, the probes would be able to pair only with probes having complementary 3' end sequences.

A double-stranded palindromic region may comprise guanine (G), cytosine (C), adenine (A) and/or thymine (T). In some embodiments, the percentage of G and C nucleotide base pairs (G/C) relative to A and T nucleotide base pairs (A/T) is greater than 50%. For example, the percentage of G/C relative to A/T of a double-stranded palindromic region may be 50% to 100%. In some embodiments, the percentage of G/C relative to A/T is greater than 60%, 65%, 70%, 75%, 80%, 85%, 90%, 95%.

In some embodiments, a double-stranded palindromic region may include an even number of nucleotide base pairs, although double-stranded palindromic region of the present disclosure are not so limited. For example, a double-stranded palindromic region may include 4, 6, 8 or 10 nucleotide base pairs. Alternatively, a double-stranded palindromic region may include 5, 7 or 9 nucleotide base pairs.

Among a plurality of nucleic acid barcoded probes, typically, the double-stranded palindromic regions are the same for each probe of the plurality such that any two probes proximate to each other are able to bind to each other through generated half-records containing the palindromic sequence. In some embodiments, however, the double-stranded palindromic regions may be the same only among a subset of barcoded probes of the plurality such that two different subsets contain two different double-stranded palindromic regions.

A "double-stranded barcoded region" refers to a double-stranded region of a nucleic acid (e.g., DNA or RNA) barcoded probe that identifies the probe as belonging to a particular molecular target or species of molecular target. A double-stranded barcoded region may comprise any combination of nucleotides in random or rationally-designed order. In some embodiments, a double-stranded barcoded region has a length of 2 to 100 nucleotide base pairs. That is, in some embodiments, a double-stranded barcoded region may comprise 2 to 100 contiguous nucleotides bound to 2 to 100 respectively complementary nucleotides. For example, a double-stranded barcoded region may have a length of 2, 3, 4, 5, 6, 7, 8, 9, 10, 11, 12, 13, 14, 15, 16, 17, 18, 19 or 20 nucleotide base pairs. In some embodiments, a double-stranded barcoded region may have a length of 2 to 5, 2 to 10, 2 to 15, 2 to 20, 2 to 25, 2 to 30, 2 to 35, 2 to 40, 2 to 45, or 2 to 50 nucleotide base pairs. In some embodiments, a double-stranded barcoded region may have a length of 35 to 50, 35 to 60, 35 to 70, 35 to 80, 35 to 90, or 35 to 100 nucleotide base pairs. In some embodiments, a double-stranded barcoded region is longer than 100 nucleotide base pairs. For example, a double-stranded barcoded region may have a length of 2 to 200 nucleotide base pairs. In some embodiments, a double-stranded barcoded region has a length of 2 to 190, 2 to 180, 2 to 170, 2 to 160, 2 to 150, 2 to 140, 2 to 130, 2 to 120, or 2 to 110 nucleotide base pairs.

A nucleic acid barcoded probe is considered "unique" or "specific" to a molecular target if the barcoded region of the probe is associated only with that molecular target and can be used to identify only that molecular target among a population of molecules, including other molecular targets with their own unique barcoded probes. Similarly, nucleic acid barcoded probe is considered "unique" or "specific" to a species of molecular target, if the barcoded region of the probe is associated only with that of molecular target and can be used to identify only that species of molecular target among a population of molecules.

A "primer-binding region" refers to a region of a nucleic acid (e.g., DNA or RNA) barcoded probe where a single-stranded primer (e.g., DNA or RNA primer) binds to start replication. A primer-binding region may be a single stranded region or a partially double stranded region, which refers to a region containing both a single-stranded segment and a double-stranded segment. An example of a partially double-stranded primer-binding region is shown in FIG. 5, where "a16" denotes a single-stranded segment of the primer-binding region, and "ax5" denotes a double-stranded segment of the primer-binding region. A primer-binding region may comprise any combination of nucleotides in random or rationally-designed order. In some embodiments, a primer-binding region has a length of 4 to 40 nucleotides (or nucleotide base pairs, or a combination of nucleotides and nucleotide base pairs, depending the single- and/or double-stranded nature of the primer-binding region). For example, a primer-binding region may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides (and/or nucleotide base pairs). In some embodiments, a primer-binding region may have a length of 4 to 10, 4 to 15, 4 to 20, 4 to 25, 4 to 30, 4 to 35, or 4 to 40 nucleotides (and/or nucleotide base pairs). In some embodiments, a primer-binding region is longer than 40 nucleotides. For example, a primer-binding region may have a length of 4 to 100 nucleotides. In some embodiments, a primer-binding region has a length of 4 to 90, 4 to 80, 4 to 70, 4 to 60, or 4 to 50 nucleotides.

In some embodiments, a primer-binding region is designed to accommodate binding of more than one (e.g., 2 or 3 different) primers.

With reference again to FIG. 3A and FIG. 5, as an example, extension of a primer (bound to a primer-binding site) by a displacing polymerase is typically terminated by the presence of a molecule or modification that terminates polymerization. Thus, in some embodiments, nucleic acid barcoded probes of the present disclosure comprise a molecule or modification that terminates polymerization. A molecule or modification that terminates polymerization ("stopper" or "blocker") is typically located in a double-stranded region of a barcoded probe, adjacent to the double-stranded palindromic region, such that polymerization terminates extension of the primer through the double-stranded palindromic region. For nucleic acid barcoded probes arranged in the form of a hairpin, a molecule or modification that terminates polymerization may be located between the double-stranded palindromic region and the hairpin loop, as shown in FIG. 5 ("spacer 9"). In some embodiments, the molecule that terminate polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" or "blocker" modification be improved by lowering dNTP concentrations (e.g., from 200 µm) in a reaction to 100 µm, 10 µm, 1 µm, or less.

Inclusion of a molecule or modification that terminates polymerization often creates a "bulge" in a double-stranded region of a barcoded probe (e.g., a stem region for hairpin structures) because the molecule or modification is not paired (see, e.g., FIG. 5). Thus, in some embodiments, barcoded probes are designed to include, opposite the molecule or modification, a single nucleotide (e.g., thymine), at least two of same nucleotide (e.g., a thymine dimer (TT) or trimer (TTT)), or an non-natural modification.

Thus, to prevent the polymerase from extending an end (e.g., a 5' or 3' end) of a barcoded probe, a poly-T sequence (e.g., a sequence of 2, 3, 4, 5, 7, 8, 9 or 10 thymine nucleotides) may be used, as shown, for example, in FIG. 5. Alternatively, a synthetic base (e.g., an inverted dT) or other modification may be added to an end (e.g., a 5' or 3' end) of a barcoded probe to prevent unwanted polymerization of the probe. Other termination molecules (molecules that prevent extension of a 3' end not intended to be extended) include, without limitation, iso-dG and iso-dC or other unnatural nucleotides or modifications.

As discussed above, generation of a half record (see, e.g., FIG. 3A) displaces one of the strands of the barcoded probe. This displaced strand, in turn, displaces a portion of the half record, starting at the 3' end. This displacement of the half-record is facilitated, in some embodiments, by a "double-stranded displacement region" adjacent to the molecule or modification that terminates polymerization (see, e.g., FIG. 5, "DS6"). In embodiments wherein the barcoded probe has a hairpin structure, the double-stranded displacement region may be located between the molecule or modification that terminates polymerization and the hairpin loop (see, e.g., FIG. 5). A double-stranded displacement region may comprise any combination of nucleotides in random or rationally-designed order. In some embodiments, a double-stranded displacement region has a length of 2 to 10 nucleotide base pairs. For example, a double-stranded displacement region may have a length of 2, 3, 4, 5, 6, 7, 8, 9 or 10 nucleotide base pairs. In some embodiments, a double-stranded palindromic region may have a length of 5 to 6 nucleotide base pairs. In some embodiments, a double-stranded palindromic region may contain only a combination of C and G nucleotides.

Displacement of the half-record may also be facilitated, in some embodiments, by modifying the reaction conditions. For example, some auto-cyclic reactions may include, instead of natural, soluble dNTPs for new strand generation, phosphorothioate nucleotides (2'-Deoxynucleoside Alpha-Thiol 2'-Deoxynucleoside Alpha-Thiol Triphosphate Set, Trilink Biotechnologies). These are less stable in hybridization that natural dNTPs, and result in a weakened interaction between half record and stem. They may be used in any combination (e.g., phosphorothioate A with natural T, C, and G bases, or other combinations or ratios of mixtures). Other such chemical modifications may be made to weaken the half record pairing and facilitate displacement.

Similarly, the probe itself may be modified, in some embodiments, with unnatural nucleotides that serve instead to strengthen the hairpin stem. In such embodiments, the displacing polymerase that generates the half record can still open and copy the stem, but, during strand displacement, stem sequence re-hybridization is energetically favorable over half-record hybridization with stem template. Non-limiting examples of unnatural nucleotides include 5-methyl dC (5-methyl deoxycytidine; when substituted for dC, this molecule increase the melting temperature of nucleic acid by as much as 5° C. per nucleotide insertion), 2,6-diaminopurine (this molecule can increase the melting temperature by as much as 1-2° C. per insertion), Super T (5-hydroxybutynl-2'-deoxyuridine also increases melting temperature of nucleic acid), and/or locked nucleic acids (LNAs). They may occur in either or both strands of the hairpin stem.

In some embodiments, unnatural nucleotides may be used to introduce mismatches between new half record sequence and the stem. For example, if an isoG nucleotide existed in the template strand of the stem, a polymerase, in some cases, will mistakenly add one of the soluble nucleotides available to extend the half record, and in doing so create a 'bulge' between the new half record and the stem template strand, much like the bulge (included in the primer) of FIG. 5A. It will serve the same purpose of weakening half-record-template interaction and encourage displacement.

In some embodiments, nucleic acid barcoded probes of the present disclosure are arranged to form a hairpin structure, which is a single stretch of contiguous nucleotides that folds and forms a double-stranded region, referred to as a "stem," and a single-stranded region, referred to as a "loop." In some embodiments, the single-stranded loop region has a length of 3 to 50 nucleotides. For example, the single-stranded loop region may have a length of 3, 4, 5, 6, 7, 8, 9 or 10 nucleotides. In some embodiments, the single-stranded loop region has a length of 3 to 10, 3 to 15, 3 to 20, 3 to 25, 3 to 30, 3 to 35, 3 to 40, 3 to 45, or 3 to 50 nucleotides. In some embodiments, the single-stranded loop region is longer than 50 nucleotides. For example, the single-stranded loop region may have a length of 3 to 200 nucleotides. In some embodiments, the single-stranded loop region has a length of 3 to 175, 3 to 150, 3 to 100, or 3 to 75 nucleotides. In some embodiments, a loop region includes smaller regions of intramolecular base pairing. A hairpin loop, in some embodiments permits flexibility in the orientation of the barcoded probe relative to a target binding-moiety. That is, the loop typically allows the barcoded probe to occupy a variety of positions and angles with respect to the target-binding moiety, thereby permitting interactions with a multitude of nearby probes (e.g., attached to other targets) in succession.

Nucleic acid barcoded probes of the present disclosure are typically attached to molecular target through a target-binding moiety. In some embodiments, the target-binding moiety is attached to an end of the barcoded probe (e.g., the end distal to the primer-binding region). In some embodiments, the target-binding moiety is attached to the single-stranded loop region of a barcoded probe arranged in the form of a hairpin (see, e.g., FIG. 5).

Examples of target-binding moieties for use as provided herein include, without limitation, biotin, antibodies, aptamers, nanobodies, nucleic acids, a drugs (e.g., small molecule drugs) and atoms (e.g., Li). Other targeting molecules are contemplated. In some embodiments, a molecular target may be attached to a barcoded probe through hybridization or "click chemistry." See, e.g., Kolb H. C., et al. *Angewandte Chemie International Edition* 2001, 40 (11): 2004-2021; and Evans R. A. *Australian Journal of Chemistry*, 2007, 60 (6): 384-395.

Nucleic acid barcoded probes of the present disclosure, in some embodiments, comprise at least one locked nucleic acid (LNA) nucleotides or other modified base. Pairs of LNAs, or other modified bases, can serve as stronger (or weaker) base pairs in double-stranded regions of barcoded probes, thus biasing the strand displacement reaction. In some embodiments, at least one LNA molecule is located on a complementary stranded of a barcoded probe, between a double-stranded barcoded region and a single-stranded primer-binding region.

Nucleic acid barcoded probes of the present disclosure, in some embodiments, are bound to a molecular target. A "molecular target" is any molecule that one wishes to observe or quantitate. Examples of molecular targets include, without limitation, proteins, saccharides (e.g., polysaccharides), lipids, nucleic acids (e.g., DNA, RNA, microRNAs), and small molecules. Molecular target may be DNA or RNA. In some embodiments, molecular target are RNA interference molecules, such as short-interfering RNAs (siRNAs) or micro RNAs (microRNAs). In some embodiments, molecular target are antisense molecules, such as DNA antisense synthetic oligonucleotides (ASOs).

In some embodiments, a molecular target is a biomolecule. As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. Examples of molecular targets, specifically biomolecules, include, without limitation, DNA, RNA, cDNA, or the DNA product of RNA subjected to reverse transcription, A23187 (Calcimycin, Calcium Ionophore), Abamectine, Abietic acid, Acetic acid, Acetylcholine, Actin, Actinomycin D, Adenosine, Adenosine diphosphate (ADP), Adenosine monophosphate (AMP), Adenosine triphosphate (ATP), Adenylate cyclase, Adonitol, Adrenaline, epinephrine, Adrenocorticotropic hormone (ACTH), Aequorin, Aflatoxin, Agar, Alamethicin, Alanine, Albumins, Aldosterone, Aleurone, Alpha-amanitin, Allantoin, Allethrin, α-Amanatin, Amino acid, Amylase, Anabolic steroid, Anethole, Angiotensinogen, Anisomycin, Antidiuretic hormone (ADH), Arabinose, Arginine, Ascomycin, Ascorbic acid (vitamin C), Asparagine, Aspartic acid, Asymmetric dimethylarginine, Atrial-natriuretic peptide (ANP), Auxin, Avidin, Azadirachtin A-C35H44O16, Bacteriocin, Beauvericin, Bicuculline, Bilirubin, Biopolymer, Biotin (Vitamin H), Brefeldin A, Brassinolide, Brucine, Cadaverine, Caffeine, Calciferol (Vitamin D), Calcitonin, Calmodulin, Calmodulin, Calreticulin, Camphor-(C10H16O), Cannabinol, Capsaicin, Carbohydrase, Carbohydrate, Carnitine, Carrageenan, Casein, Caspase, Cellulase, Cellulose-(C6H10O5), Cerulenin, Cetrimonium bromide (Cetrimide)-C19H42BrN, Chelerythrine, Chromomycin A3, Chaparonin, Chitin, α-Chloralose, Chlorophyll, Cholecystokinin (CCK), Cholesterol, Choline, Chondroitin sulfate, Cinnamaldehyde, Citral, Citric acid, Citrinin, Citronellal, Citronellol, Citrulline, Cobalamin (vitamin B12), Coenzyme, Coenzyme Q, Colchicine, Collagen, Coniine, Corticosteroid, Corticosterone, Corticotropin-releasing hormone (CRH), Cortisol, Creatine, Creatine kinase, Crystallin, α-Cyclodextrin, Cyclodextrin glycosyltransferase, Cyclopamine, Cyclopiazonic acid, Cysteine, Cystine, Cytidine, Cytochalasin, Cytochalasin E, Cytochrome, Cytochrome C, Cytochrome c oxidase, Cytochrome c peroxidase, Cytokine, Cytosine-C4H5N3O, Deoxycholic acid, DON (DeoxyNivalenol), Deoxyribofuranose, Deoxyribose, Deoxyribose nucleic acid (DNA), Dextran, Dextrin, DNA, Dopamine, Enzyme, Ephedrine, Epinephrine-C9H13NO3, Erucic acid-CH3(CH2)7CH=CH(CH2)11COOH, Erythritol, Erythropoietin (EPO), Estradiol, Eugenol, Fatty acid, Fibrin, Fibronectin, Folic acid (Vitamin M), Follicle stimulating hormone (FSH), Formaldehyde, Formic acid, Formnoci, Fructose, Fumonisin B1, Gamma globulin, Galactose, Gamma globulin, Gamma-aminobutyric acid, Gamma-butyrolactone, Gamma-hydroxybutyrate (GHB), Gastrin, Gelatin, Geraniol, Globulin, Glucagon, Glucosamine, Glucose-C6H12O6, Glucose oxidase, Gluten, Glutamic acid, Glutamine, Glutathione, Gluten, Glycerin (glycerol), Glycine, Glycogen, Glycolic acid, Glycoprotein (e.g., glycoprotein enzymes such as prostate-specific antigen (PSA)), Gonadotropin-releasing hormone (GnRH), Granzyme, Green fluorescent protein, Growth hormone, Growth hormone-releasing hormone (GHRH), GTPase, Guanine, Guanosine, Guanosine triphosphate (+GTP), Haptoglobin, Hematoxylin, Heme, Hemerythrin, Hemocyanin, Hemoglobin, Hemoprotein, Heparan sulfate, High density lipoprotein, HDL, Histamine, Histidine, Histone, Histone methyltransferase, HLA antigen, Homocysteine, Hormone, human chorionic gonadotropin (hCG), Human growth hormone, Hyaluronate, Hyaluronidase, Hydrogen peroxide, 5-Hydroxymethylcytosine, Hydroxyproline, 5-Hydroxytryptamine, Indigo dye, Indole, Inosine, Inositol, Insulin, Insulin-like growth factor, Integral membrane protein, Integrase, Integrin, Intein, Interferon, Inulin, Ionomycin, Ionone, Isoleucine, Iron-sulfur cluster, K252a, K252b, KT5720, KT5823, Keratin, Kinase, Lactase, Lactic acid, Lactose, Lanolin, Lauric acid, Leptin, Leptomycin B, Leucine, Lignin, Limonene, Linalool, Linoleic acid, Linolenic acid, Lipase, Lipid, Lipid anchored protein, Lipoamide, Lipoprotein, Low density lipoprotein, LDL, Luteinizing hormone (LH), Lycopene, Lysine, Lysozyme, Malic acid, Maltose, Melatonin, Membrane protein, Metalloprotein, Metallothionein, Methionine, Mimosine, Mithramycin A, Mitomycin C, Monomer, Mycophenolic acid, Myoglobin, Myosin, Natural phenols, Nucleic Acid, Ochratoxin A, Oestrogens, Oligopeptide, Oligomycin, Orcin, Orexin, Ornithine, Oxalic acid, Oxidase, Oxytocin, p53, PABA, Paclitaxel, Palmitic acid, Pantothenic acid (vitamin B5), parathyroid hormone (PTH), Paraprotein, Pardaxin, Parthenolide, Patulin, Paxilline, Penicillic acid, Penicillin, Penitrem A, Peptidase, Pepsin, Peptide, Perimycin, Peripheral membrane protein, Perosamine, Phenethylamine, Phenylalanine, Phosphagen, phosphatase, Phospholipid, Phenylalanine, Phytic acid, Plant hormones, Polypeptide, Polyphenols, Polysaccharides, Porphyrin, Prion, Progesterone, Prolactin (PRL), Proline, Propionic acid, Protamine, Protease, Protein, Proteinoid, Putrescine, Pyrethrin, Pyridoxine or pyridoxamine (Vitamin B6), Pyrrolysine, Pyruvic acid, Quinone, Radicicol, Raffinose, Renin, Retinene, Retinol (Vitamin A), Rhodopsin (visual purple), Riboflavin (vitamin B2), Ribofuranose, Ribose, Ribozyme, Ricin, RNA-Ribonucleic acid, RuBisCO, Safrole, Salicylaldehyde, Salicylic acid, Salvinorin-A-C23H28O8, Saponin, Secretin, Selenocysteine, Selenomethionine, Selenoprotein, Serine, Serine kinase, Serotonin, Skatole, Signal recognition particle, Somatostatin, Sorbic acid, Squalene, Staurosporin, Stearic acid, Sterigmatocystin, Sterol, Strychnine, Sucrose (sugar), Sugars (in general), superoxide, T2 Toxin, Tannic acid, Tannin, Tartaric acid, Taurine, Tetrodotoxin, Thaumatin, Topoisomerase, Tyrosine kinase, Taurine, Testosterone, Tetrahydrocannabinol (THC), Tetrodotoxin, Thapsigargin, Thaumatin, Thiamine (vitamin B1)-C12H17ClN4OS.HCl, Threonine, Thrombopoietin, Thymidine, Thymine, Triacsin C, Thyroid-stimulating hormone (TSH), Thyrotropin-releasing hormone (TRH), Thyroxine (T4), Tocopherol (Vitamin E), Topoisomerase, Triiodothyronine (T3), Transmembrane receptor, Trichostatin A, Trophic hormone, Trypsin, Tryptophan, Tubulin, Tunicamycin, Tyrosine, Ubiquitin, Uracil, Urea, Urease, Uric acid-C5H4N4O3, Uridine, Valine, Valinomycin, Vanabins, Vasopressin, Verruculogen, Vitamins (in general), Vitamin A (retinol), Vitamin B, Vitamin B1 (thiamine), Vitamin B2 (riboflavin), Vitamin B3 (niacin or nicotinic acid), Vitamin B4 (adenine), Vitamin B5 (pantothenic acid), Vitamin B6 (pyridoxine or pyridoxamine), Vitamin B12 (cobalamin), Vitamin C (ascorbic acid), Vitamin D (calciferol), Vitamin E (tocopherol), Vitamin F, Vitamin H (biotin), Vitamin K (naphthoquinone), Vitamin M (folic acid), Wortmannin and Xylose.

In some embodiments, a molecular target is a protein target such as, for example, proteins of a cellular environment (e.g., intracellular or membrane proteins). Examples of proteins include, without limitation, fibrous proteins such as cytoskeletal proteins (e.g., actin, arp2/3, coronin, dystrophin, FtsZ, keratin, myosin, nebulin, spectrin, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins,C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins; cell adhesion proteins (e.g., cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones); receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins, major histocompatibility antigens and T cell receptors); nutrient storage/transport proteins (e.g., ferritin); chaperone proteins; and enzymes.

In some embodiments, the target protein is prostate-specific antigen (PSA). PSA (also referred to as gamma-seminoprotein or kallikrein-3) is a glycoprotein encoded in humans by the KLK3 gene. PSA is a member of the kallikrein-related peptidase family and is secreted by the epithelial cells of the prostate gland.

Nucleic acid barcoded probes of the present disclosure may be DNA such as D-form DNA and L-form DNA and RNA, as well as various modifications thereof. Nucleic acid modifications include base modifications, sugar modifications, and backbone modifications. Non-limiting examples of such modifications are provided below.

Examples of modified nucleic acids (e.g., DNA variants) that may be used in accordance with the present disclosure include, without limitation, L-DNA (the backbone enantiomer of DNA, known in the literature), peptide nucleic acids (PNA) bisPNA clamp, a pseudocomplementary PNA, locked nucleic acid (LNA), and co-nucleic acids of the above such as DNA-LNA co-nucleic acids. Thus, the present disclosure contemplates nanostructures that comprise DNA, RNA, LNA, PNA or combinations thereof. It is to be understood that the nucleic acids used in methods and compositions of the present disclosure may be homogeneous or heterogeneous in nature. As an example, nucleic acids may be completely DNA in nature or they may be comprised of DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some embodiments, nucleic acids are nuclease-resistant.

Also provided herein are pluralities of nucleic acid barcoded probes. A "plurality" comprises at least two nucleic acid barcoded probes. In some embodiments, a plurality comprises 2 to 2 million nucleic acid barcoded probes (e.g., unique barcoded probes). For example, a plurality may comprise 100, 500, 1000, 5000, 10000, 100000, 1000000, or more, nucleic acid barcoded probes. This present disclosure is not limited in this aspect.

Figure 10A:
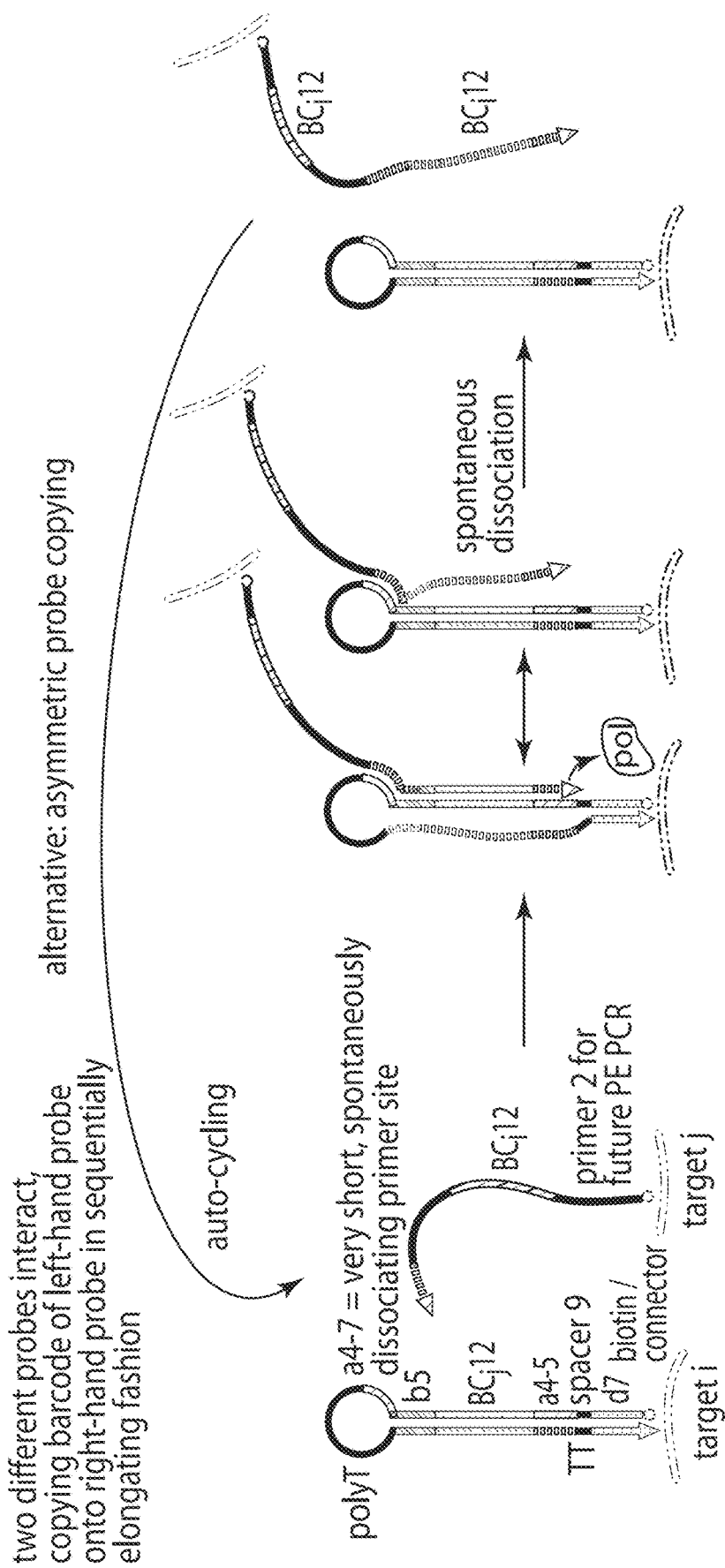
FIG. 10A shows an example of "asymmetrical" auto-cycling probes. Two probes interact to copy the barcode region from the hairpin-like probe on the left ($BC_j12$) onto the linear probe on the right. Various probe configurations are provided herein (FIGS. 10B-10E). This probe set is also autocyclic, repeatedly concatenating barcodes to the 3' end of the right-hand probe.
Figure 10B:
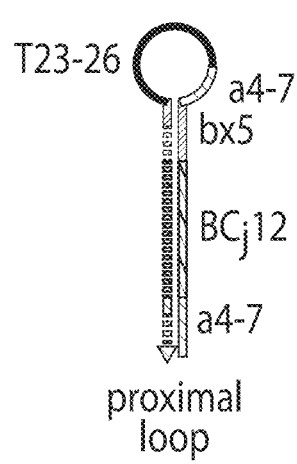
Figure 10C:
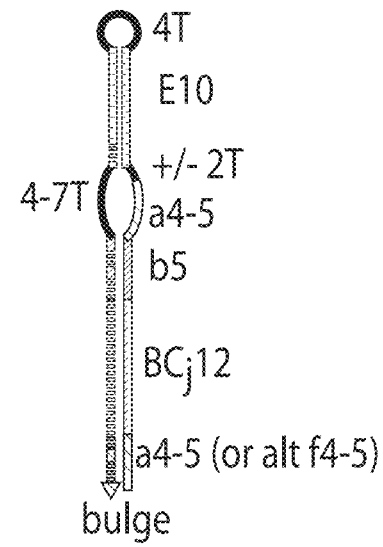
Figure 10D:
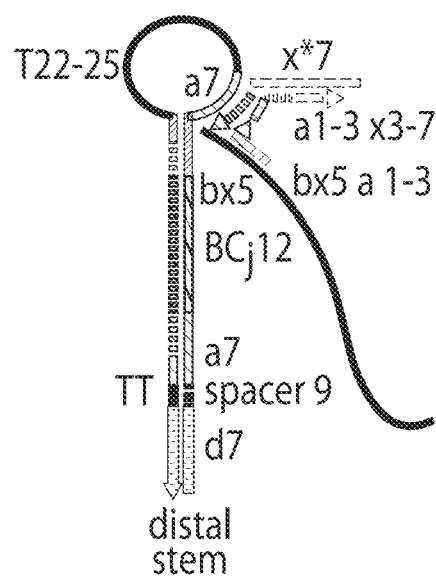
Figure 10E:
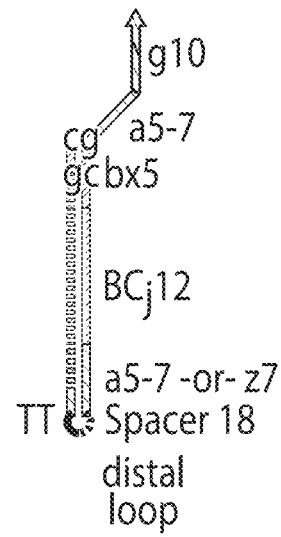

Also provided herein are pairs of nucleic acid barcoded probes. Such pairs are intended to be used in combination with each other to detect molecular target spatial arrangements and associations. In some embodiments, a pair of nucleic acid barcoded probes comprises (a) a first nucleic acid barcoded probe arranged into (i) a double-stranded barcode region, and (ii) a primer-binding region (e.g., a single-stranded primer-binding region), referred to for simplicity as "the first probe," and (b) a second single-stranded barcoded probe comprising a barcode region and a primer region complementary to the single-stranded primer-binding region, referred to as "the second probe" (see, e.g., FIG. 10A). Each probe is attached to a molecular target through a target binding moiety. In a microscope-free imaging reaction containing the foregoing pair of barcoded probes, palindromic regions are unnecessary because the second probe—the single-stranded probe—includes a primer that binds directly to the primer-binding region of the first probe. As shown in the example depicted in FIG. 10A, the second barcoded probe contains a primer at one end (e.g., 3' end and/or distal to the end that is attached to a molecular target), which is complementary to and binds to the primer-binding region of the first probe. Once bound to the primer-binding region of the first probe, the primer of the second probe is polymerized through the barcoded region of the first probe, thereby generating a record of its association with the first probe—the second probe now contains two different barcodes. The displacing strand of the first probe (which was displaced during polymerization of the primer) partially displaces the second probe when it "re-binds" to its complementary strand on the first probe. The partially-displaced second probe then spontaneously dissociates from the first probe. The second probe, now containing a record of its association with the first probe, is free to bind to another probe and "record" that second association (see, e.g., FIG. 10A).

Generally, any two barcoded probes can be attached respectively to two molecular targets. In some embodiments, however, two barcoded probes may be attached to different epitopes of the same molecular target (e.g., a protein such as an antibody), for example, in order to generate records that represent the presence of that molecular target in solution—many copies of the same record are created when two such barcoded probes are proximate to each other) (see, e.g., FIG. 18). In some embodiments, this permits digital 'counting' of the number of target molecules in solution.

Figure 18:
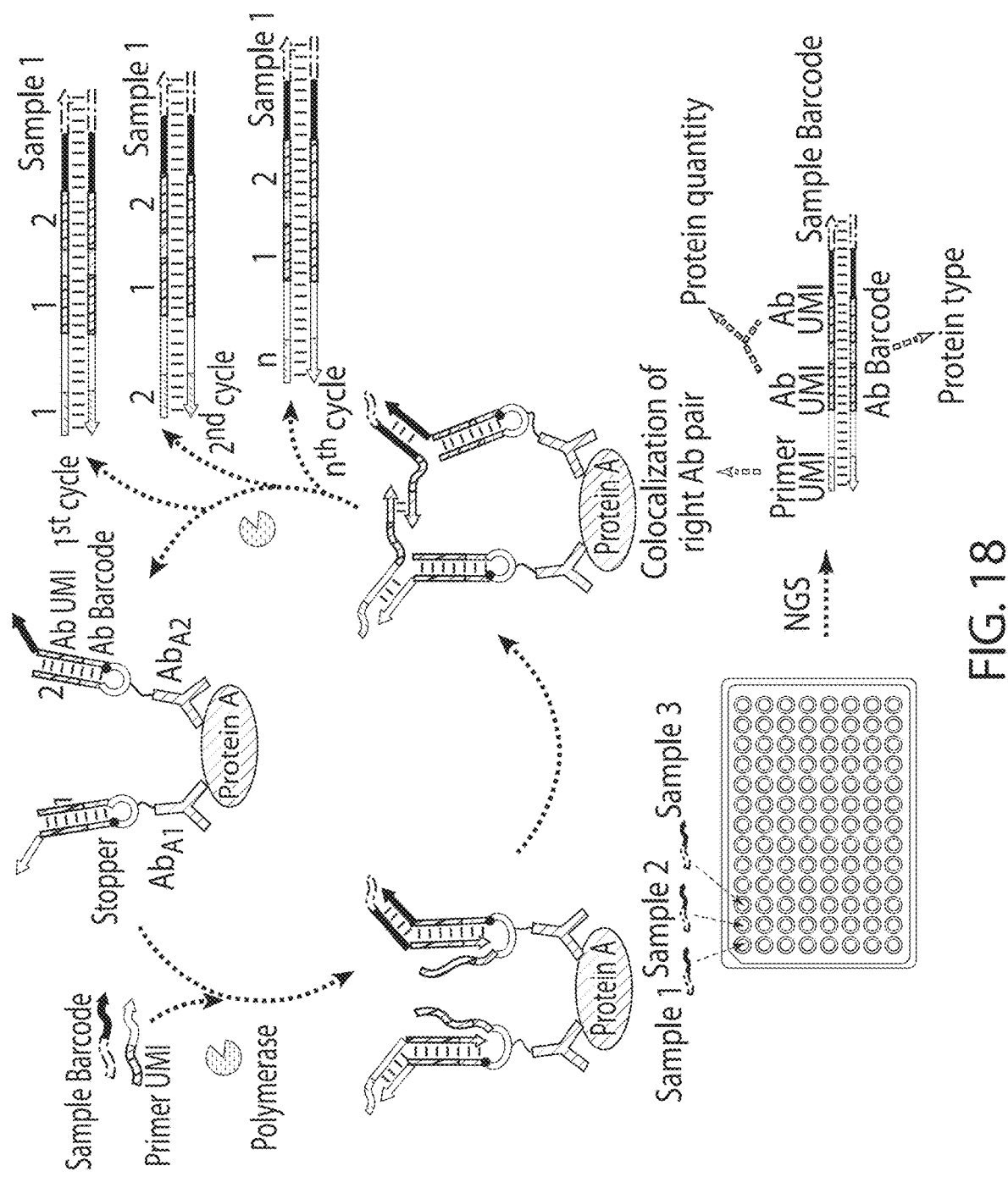
FIG. 18 shows a schematic of an example of a microscope-free imaging method for sequencing-based target protein counting. A variety of information, including, for example, protein type, digital count, and sample origin, can be decoded from reading the sequences of generated DNA reporter strands/records. The number of unique record barcodes created when two probes target the same protein indicates the number of proteins in the system. This scheme also utilizes a random "unique molecular identifier" barcode on the record primers themselves, such that chance interactions (not caused by co-localization on a target protein) between probes can be neglected in post-processing by virtue of the low (e.g., single) number of records produced in that pairing.

FIG. 18 shows an example in which auto-cyclically generated DNA sequences report antibody co-localization on single-molecule level. Specifically, random barcode sequences (in this particular figure referred to as unique molecular identifiers (UMI) for individual antibody (Ab) molecule and barcodes for different Ab types) are incorporated into DNA hairpin probes attached on Abs. After Ab pairs are co-localized on their target, primer pairs with UMIs and sample barcodes bind each hairpin probe at the 3' overhang respectively. Polymerase extends the primers up to a synthetic "stopper" site, copying the Ab UMI (1, 2) and Ab barcode. The extended primers are then partially released from the hairpins by strand displacement and pair their 3' Ab barcode segments (unique for the target protein). These sequences are again extended, releasing reporter strands that carry both Ab UMIs (1 and 2) and a primer UMI (1). Hairpin probes thus are regenerated to their initial state and undergo additional cycles, generating reporter strands that carry the same Ab UMI pair (1 and 2) but a different primer UMI (2 to n) in each cycle. In contrast, if the antibody pair just randomly meet each other in the bulk solution, instead of co-localizing on a target, they would only generate reporter stands once with one primer UMI for each Ab UMI pair. Therefore, the signal generated by true colocaliztion event is individually read by sequencing the reporter strands, and background reporter strands can be easily discarded by reading primer UMI on each Ab UMI pair. This feature makes detecting single protein molecule possible and the assay can be scaled up using, for example, next-generation sequencing technologies.

Systems and Methods

Microscope-free imaging systems, as provided herein, comprise nucleic acid barcoded probes, primers designed to bind to those probes and displacing polymerase.

A "primer" is a single-stranded nucleic acid that serves as a starting point for nucleic acid synthesis. A polymerase adds nucleotides to a primer to generate a new nucleic acid strand. Primers of the present disclosure are designed to be complementary to and to bind to the primer-binding region of a nucleic acid barcoded probe. Thus, primer length and composition (e.g., nucleotide composition) depend, at least in part, on the length and composition of a primer-binding region of a barcoded probe. In some embodiments, a primer has a length of 4 to 40 nucleotides. For example, a primer may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, a primer may have a length of 4 to 10, 4 to 15, 4 to 20, 4 to 25, 4 to 30, 4 to 35, or 4 to 40 nucleotides.

Figure 12:
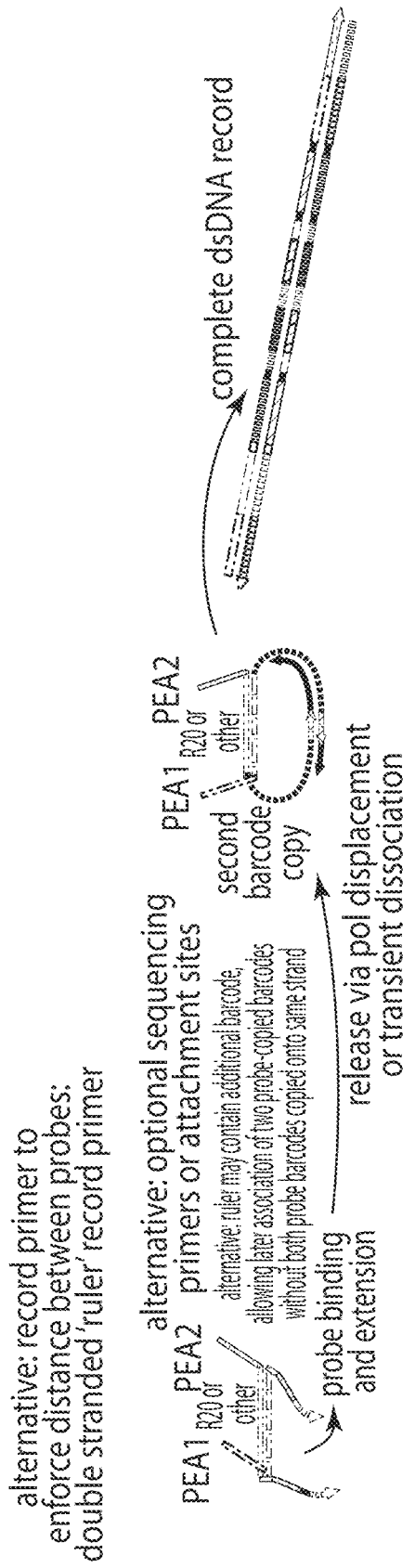
FIG. 12 shows another example of a primer of the present disclosure.

Primers may exist attached in pairs or other combinations (e.g., triplets or more, in any geometry) for the purpose, for example, of restricting probe binding to those meeting their geometric criteria (see, e.g., FIG. 12). The rigid, double-stranded linkage shown enforces both a minimum and a maximum distance between barcoded probes. The double-stranded "ruler" domain may be any length (e.g., 2 to 100 nucleotides, or more) and may optionally include a barcode itself that links the two halves by information content, should they become separated during processing. In some embodiments, a double stranded ruler domain, which enforces a typical distance between probes at which records may be generated, is a complex structure, such as a 2-, 3-, or 4-DNA helix bundle, DNA nanostructure, such as a DNA origami structure, or other structure that adds or modifies the stiffness/rigidity of the ruler.

A "strand-displacing polymerase" refers to a polymerase that is capable of displacing downstream nucleic acid (e.g., DNA) encountered during nucleic acid synthesis. Different polymerases can have varying degrees of displacement activity. Examples of strand-displacing polymerases include, without limitation, Bst large fragment polymerase (e.g., New England Biolabs (NEB) #M0275), phi 29 polymerase (e.g., NEB #M0269), Deep VentR polymerase, Klenow fragment polymerase, and modified Taq polymerase. Other strand-displacing polymerases are contemplated.

Figure 9A:
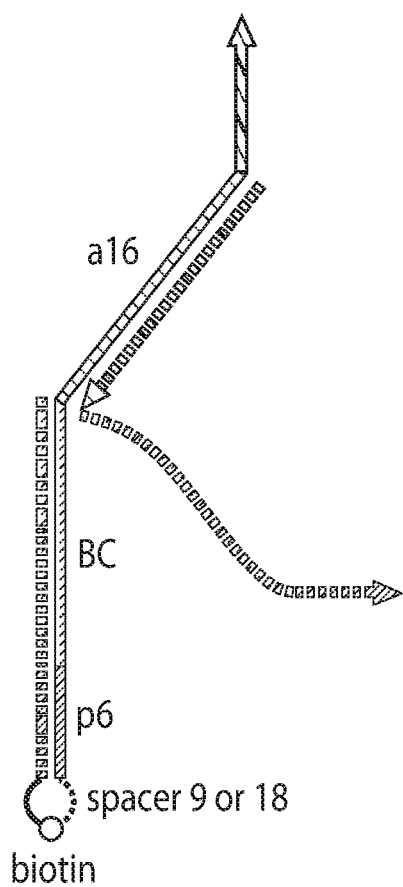
FIGS. 9A-9G show other examples of symmetrical auto-cycling probes of the present disclosure.
Figure 9B:
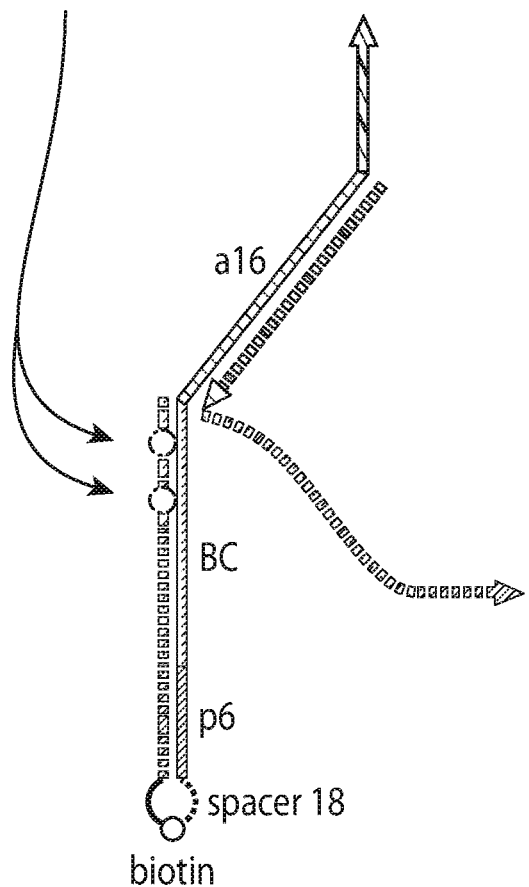
Figures 9C, 9D:
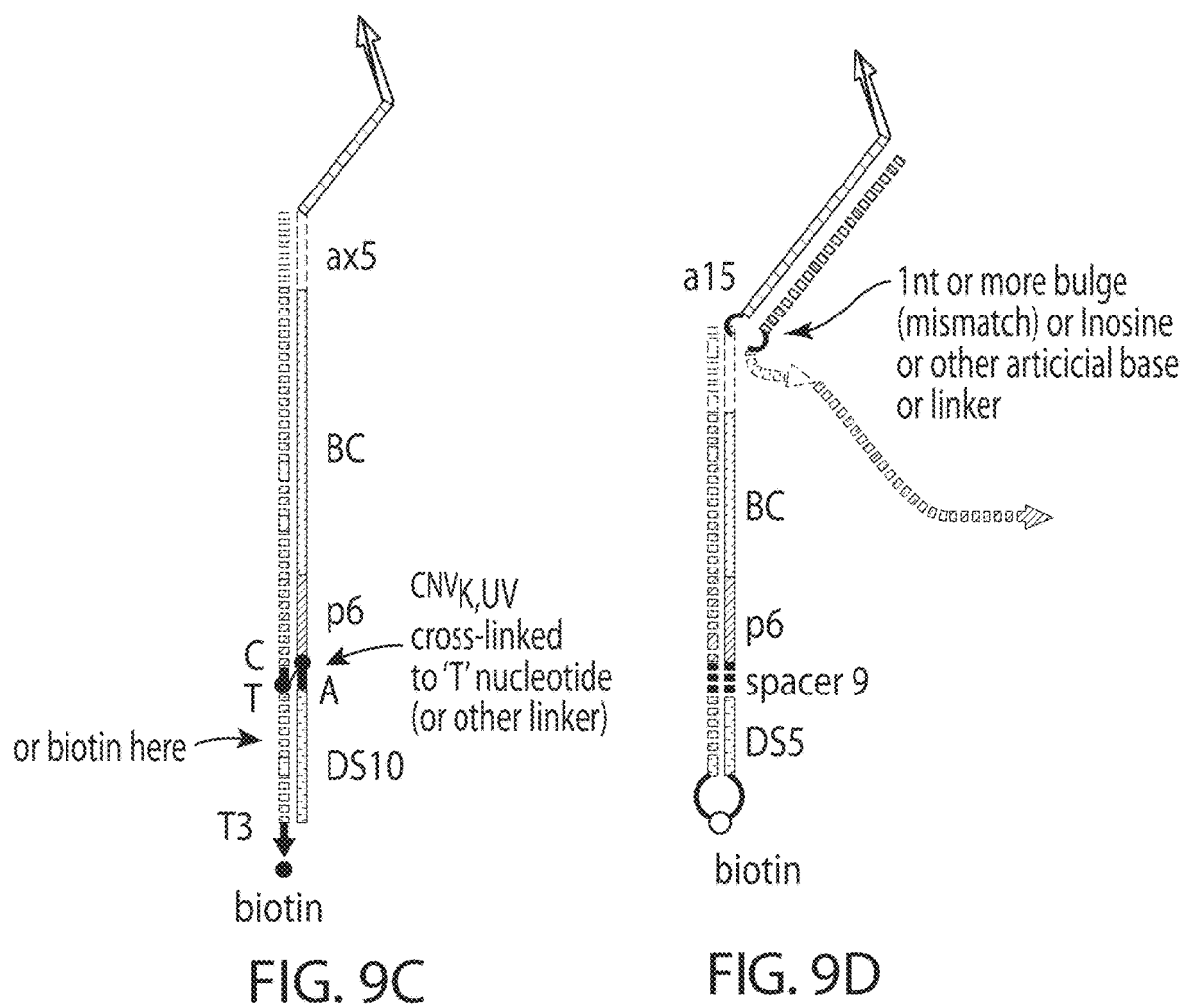
Figure 9E:
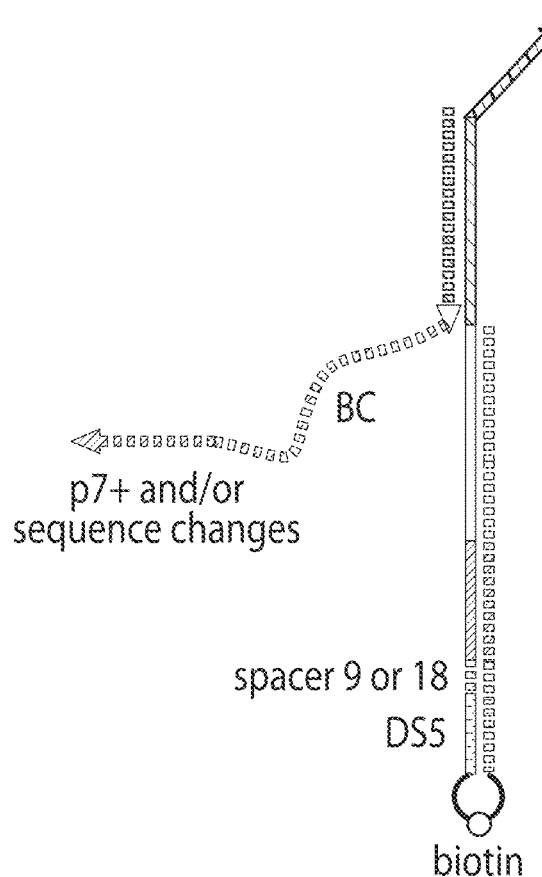

In some embodiments, a primer comprises at least one nucleotide mismatch relative to the single-stranded primer-binding region. Such a mismatch may be used facilitate displacement of a half-record from the complementary strand of a barcoded probe (see, e.g., FIG. 9D). In some embodiments, a primer comprises at least one artificial linker.

The "cycling rate" of a microscope-free imaging reaction, as provided herein, refers to the rate at which a full-record (as opposed to half-record) is produced, resulting from the cyclic interaction of two proximate barcoded molecular targets. In some embodiments, a primer comprising a mismatch or an artificial linker increases the cycling rate by 5-fold to 10-fold, or more.

Figure 9F:
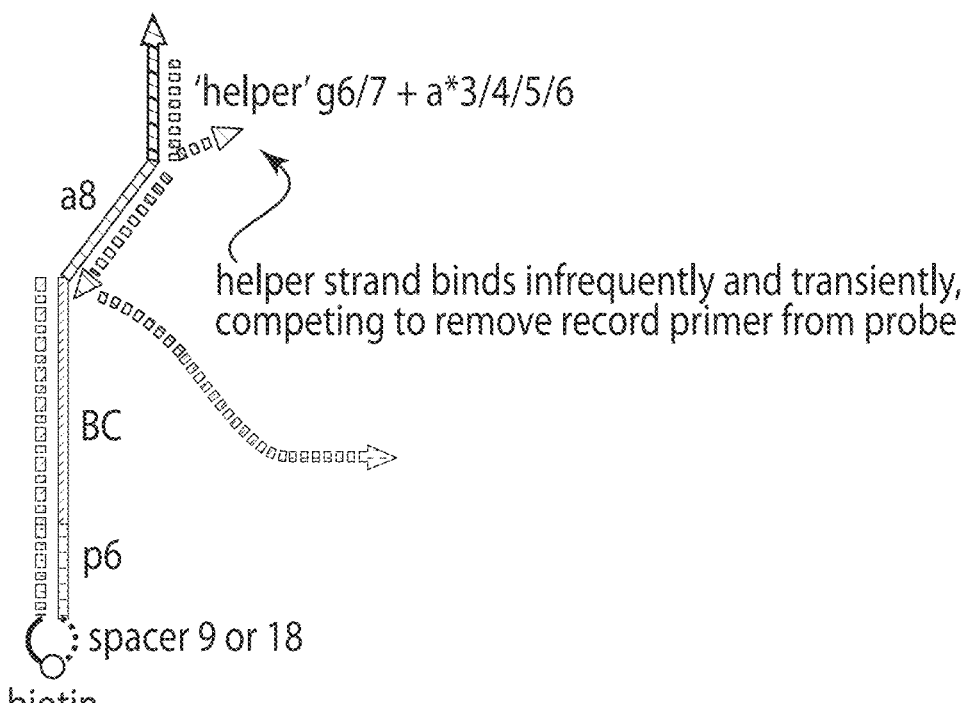
Figure 9G:
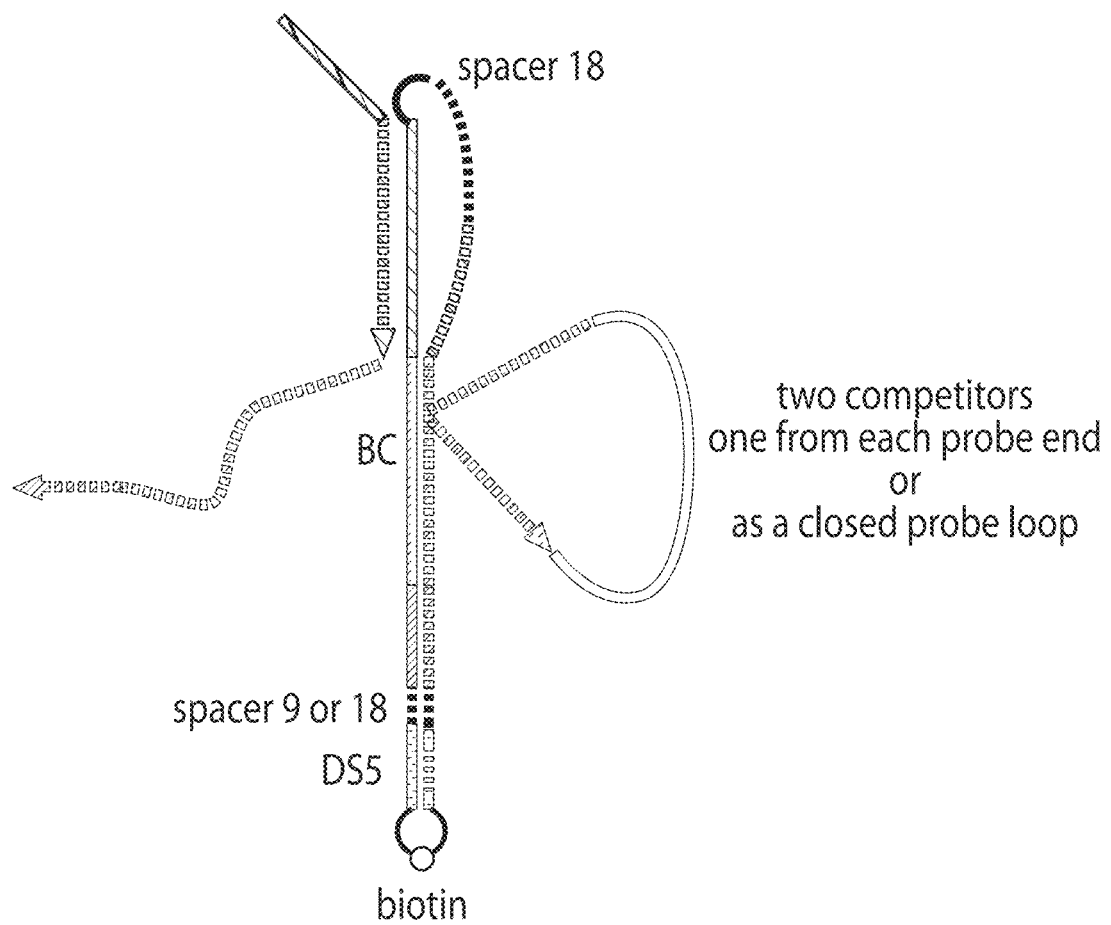

In some embodiments, microscope-free imaging systems of the present disclosure further comprise a helper nucleic acid strand that is partially complementary to the single-stranded primer binding region, is partially complementary to a single-stranded region adjacent to the primer binding region, and binds transiently to the single-stranded region adjacent to the primer binding region (see, e.g., FIG. 9F). A "helper strand" permits initiation of polymerization by the polymerase while also permitting the presence of a mismatch, as described above. In some embodiments, a helper strand has a length of 3 to 20 nucleotides. For example, a helper strand may have a length of 3, 4, 5, 6, 7, 8, 9, 10, 11, 12, 13, 14, 15, 16, 17, 18, 19 or 20 nucleotides.

Provided herein are methods of detecting molecular target interactions (e.g., with each other). In some embodiments, the methods comprise the steps of (a) contacting, with at least one (e.g., a plurality) of the nucleic acid barcoded probes as provided herein, a sample containing at least one molecular target, a primer complementary to a single-stranded primer-binding region of a probe of the plurality, and a strand-displacement polymerase, and (b) incubating the sample under conditions that permit production of barcoded records.

In some embodiments, the methods comprise the steps of contacting, with a pair of nucleic acid barcoded probes as provided herein, a sample containing at least two molecular targets, and a strand-displacement polymerase, and (b) incubating the sample under conditions that permit production of barcoded records (e.g., under conditions that permit nucleic acid replication).

A "sample" may comprise cells (or a cell), tissue, or bodily fluid such as blood (serum and/or plasma), urine, semen, lymphatic fluid, cerebrospinal fluid or amniotic fluid. A sample may be obtained from (or derived from) any source including, without limitation, humans, animals, bacteria, viruses, microbes and plants. In some embodiments, a sample is a cell lysate or a tissue lysate. A sample may also contain mixtures of material from one source or different sources. A sample may be a spatial area or volume (e.g., a grid on an array, or a well in a plate or dish).

In some embodiments, a sample is a single cell, such as a rare cell. Examples of a rare cells include, without limitation, circulating tumor cells, epithelial progenitor and stem cells, mesenchymal cells, and fetal cells, for example, circulating in the blood stream.

"Conditions that permit production of barcoded records" may be physiological conditions (e.g., a temperature of 20-40 degrees Celsius, atmospheric pressure of 1, and/or a pH value of 6-8).

In some embodiments, step (b) is performed at a temperature of 20 to 40 degrees Celsius (° C.). For example, step (b) may be performed at a temperature of 20° C., 21° C., 22° C., 23° C., 24° C., 25° C., 26° C., 27° C., 28° C., 29° C., 31° C., 32° C., 33° C., 34° C., 35° C., 36° C., 37° C., 38° C., 39° C. or 40° C.

In some embodiments, step (b) is performed for a time of 10 minutes (min) to 24 hours, or more. For example, step (b) may be performed for a time of 10 min to 3 hours (hr), 10 min to 12 hr, 10 min to 18 hr, or 10 min to 24 hr. In some embodiments, step (b) is performed for a time of 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min or 180 min.

Microscope-free imaging reaction may, in some embodiments, have a salt concentration of 0.25-15 mM Mg and/or 50-250 mM Na.

Microscope-free imaging reaction may, in some embodiments, have reaction dNTPs concentrations of 0.05-5 mM (e.g., 0.05 mM, 0.10 mM, 0.15 mM, 0.20 mM, 0.25 mM, 0.30 mM, 0.35 mM, 0.40 mM, 0.45 mM, 0.50 mM, 1.0 mM, 1.5 mM, 2.0 mM, 2.5 mM, 3.0 mM, 3.5 mM, 4.0 mM, 4.5 mM or 5.0 mM.

Buffers that may be used in microscope-free imaging reaction include, without limitation, "Thermo-Pol Buffer" (New England Biolabs), phosphate buffered saline (with or without Mg or Na supplementation), any commercial or laboratory-prepared cell media, water or any pH-buffered solution supplemented with cationic salts sufficient for DNA hybridization and polymerase operation.

In some embodiments, the cycling rate of a microscope-free imaging reaction, as provided herein, is 1 full-record per 10 minutes per pair of probes, but may be as rapid as 1 full record per second or as slow as 1 full record per 10 hours under certain (e.g., more restrictive) conditions.

At the end of microscope-free imaging "cycle," nucleic acid records (referred to herein simply as "records") of the spatial configuration of barcoded targets are produced (see, e.g., FIG. 3A). In some embodiments, the records are double-stranded. In some embodiments, the records are single-stranded. The length of the records may vary. For example, a barcoded record may have a length of 30 to 500 nucleotides (or nucleotide base pairs). In some embodiments, a barcoded record has a length of 30 to 100, 30 to 200, 30 to 300, 30 to 400, 50 to 100, 50 to 200, 50 to 300, 50 to 400 or 50 to 500 nucleotides (or nucleotide base pairs). In some embodiments, a barcoded record has a length of 80 to 100 nucleotides (or nucleotide base pairs), or 90 nucleotides (or nucleotide base pairs).

Figure 14:
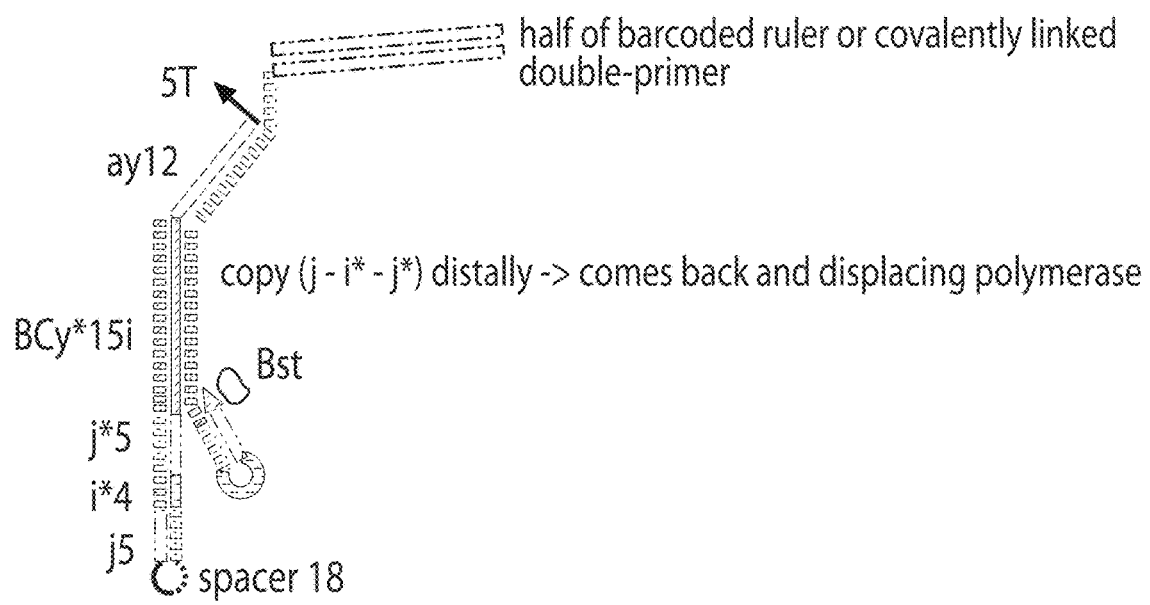
FIG. 14 shows examples of record-release mechanisms of the present disclosure.

Records may be "released" from probes via polymerase-mediated mechanisms or via spontaneous release of an extended primer from the primer-binding region on a probe. In some embodiments, as shown in FIG. 14, the 3' end of an extended primer can be engineered to fold back on itself and extended off of the probe. Because microscope-free imaging systems of the present disclosure do not typically copy the paired barcode onto the same record strand, an additional barcode may be added to a ruler-like primer that links pairs of records together in informational content.

After barcoded records are generated, they are collected and, in some embodiments, purified. For example, records may be collected in the supernatant of the reaction or by collecting the all the contents of the reaction vessel. Further preparation of the records for sequencing may sequencing platform-specific. Some platforms may require no further preparation, but often the records must have a combination of (1) a sequencing-specific 'adapter' or other oligonucleotides added to their ends, (2) undergo 'amplification' reactions (e.g., polymerase chain reaction (PCR)) in which identical or nearly-identical (e.g., 99%, 98%, 95%, 90%, 80% identical) copies of the records (with or without 'adapter' sequences) are produced, and (3) purification from other sequences, proteins, or reaction components that may interfere with preparation or sequencing. For example, adapter sequences may be ligated to the records using a common 'A-Tailing' technique, followed by gel electrophoresis purification, and finally PCR amplification. Alternatively, some embodiments may allow for PCR amplification of records directly, possibly adding adapter sequences through long DNA primers, or followed by adapter ligation and gel purification.

In some embodiments, two or more types of recording primers may be used to, for example, facilitate later PCR amplification or preparation for sequencing. Each primer may have the same probe-binding sequence, but vary in an additional 5' sequence not involved in the recording reaction. In the case of two primer types, an average of half of all resultant records will have different, non-complementary 5' and 3' ends. These may be used for further amplification (e.g., by allowing the ends to more easily hybridize with soluble PCR primers instead of forming a hairpin stem), ligation or other processing. If ten types of such recording primers are used, for example, then an average of 90% of all records will have different, non-complementary 5' and 3' ends, further facilitating end-specific amplification and processing.

Figure 19A:
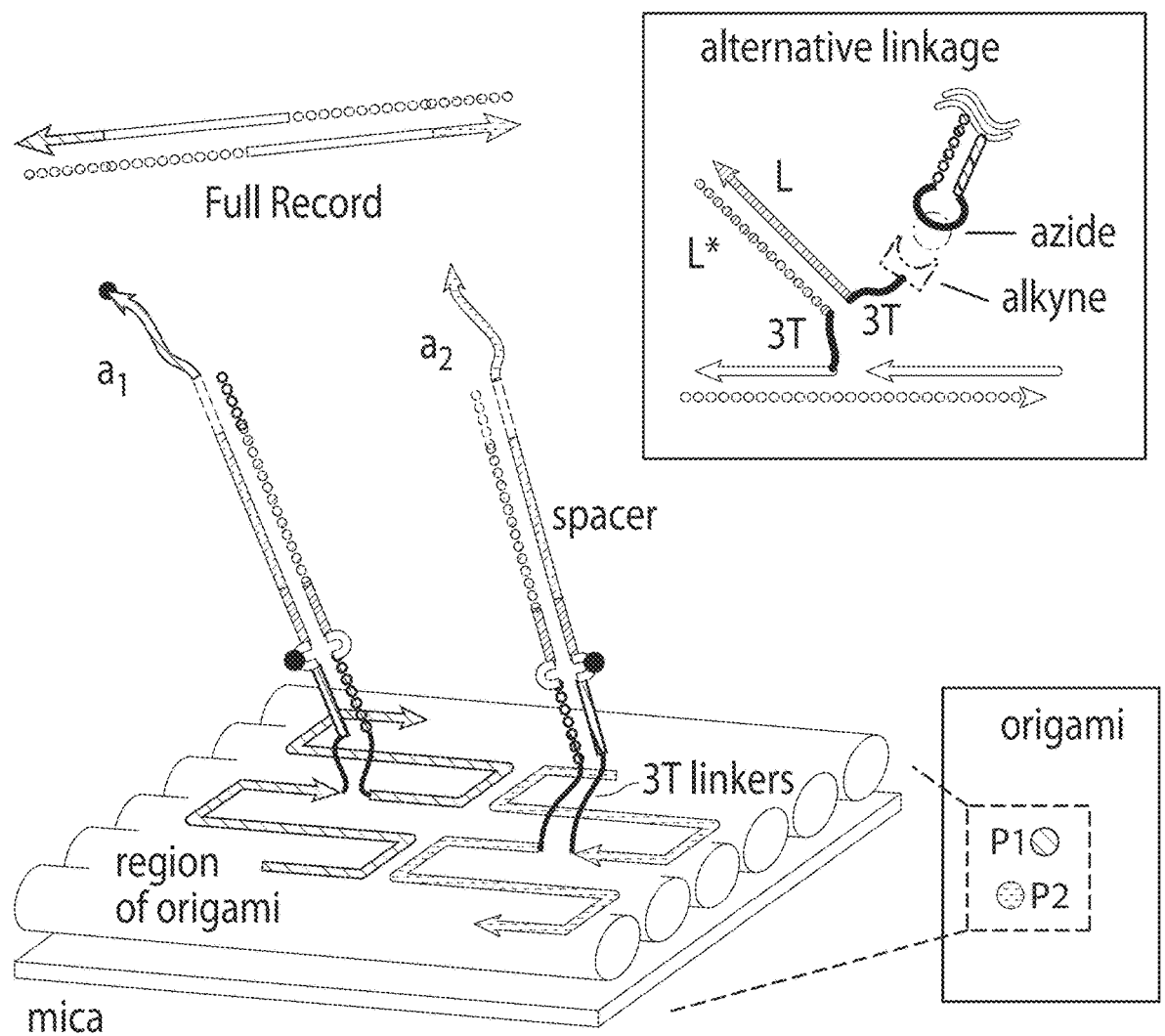
FIGS. 19A-19C present data characterizing probe reach and geometry. To control relative probe positioning precisely, probes were attached to 2D, rectangular, twist-corrected DNA nanostructures measuring 70 by 100 nm (FIG. 19A). After complete assembly, nanostructures were deposited randomly on mica surfaces in the presence of 12.5 mM $Mg_{2+}$ for firm adhesion, a condition that protects nanostructures from degradation by polymerase. Each probe was held by direct extension of two short nucleic acids (shown, on small section of nanostructure) or covalent attachment to an intermediary oligonucleotide (inset; azide on probe loop covalently attached to alkyne on TTT-L intermediary via DIBO-based click chemistry and gel-purified). Separation of probes was measured at the nanostructure attachment point. Records produced could be PCR-amplified with, for example, a1* and a2* primers. Otherwise identical probes with spacer lengths of 0 or 12 (attached by staple extension), or 18 nt (covalently attached), were held in pairs separated from 6 to 48 nm by 6 nm increments, recorded (1 hour at room temperature, approximately 50 million nanostructures per well, 100 nM primers), and Log-phase PCR amplified (20 cycles, 500 nM primers) to gel-detectable levels (FIG. 19B). Denaturing PAGE band quantification was normalized to a constant reference pair for each well. The entire series for a given probe pair type was then fit by least squares recursion to a sigmoidal curve $c1/(1+Exp[c2(dist-c3)])$, where dist represents the separation distance, and normalized to a maximum rate of 1. The same nanostructure base rectangle was adopted to hold three probes (P1, P2, P3, of 18 nt spacer design) at 30 nm intervals in four arrangements (simplified diagram) (FIG. 19C). When in a triangular arrangement, all three probe pairs yielded records, but in linear arrangements only adjacent probe pairs produced records. Similar to FIG. 19B, log-phase PCR was quantified by denaturing PAGE.
Figure 19B:
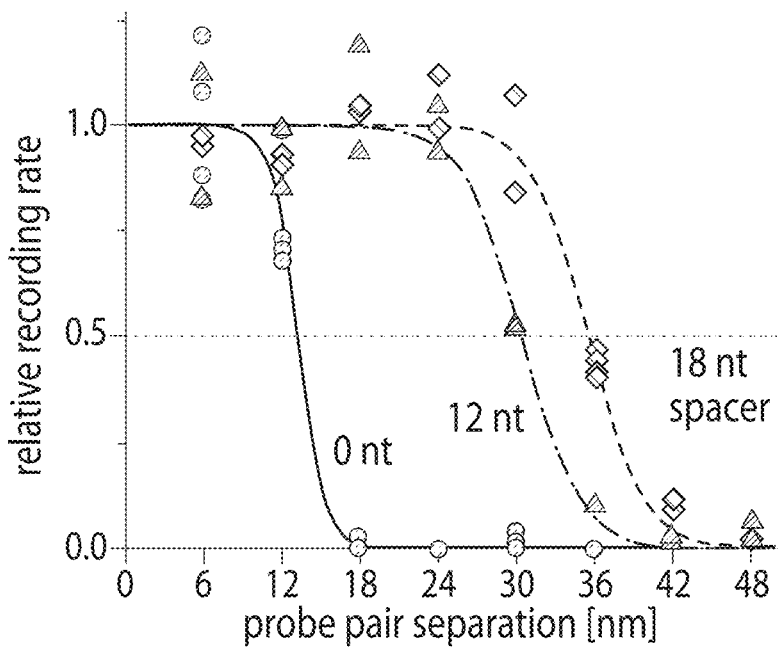
Figure 19C:
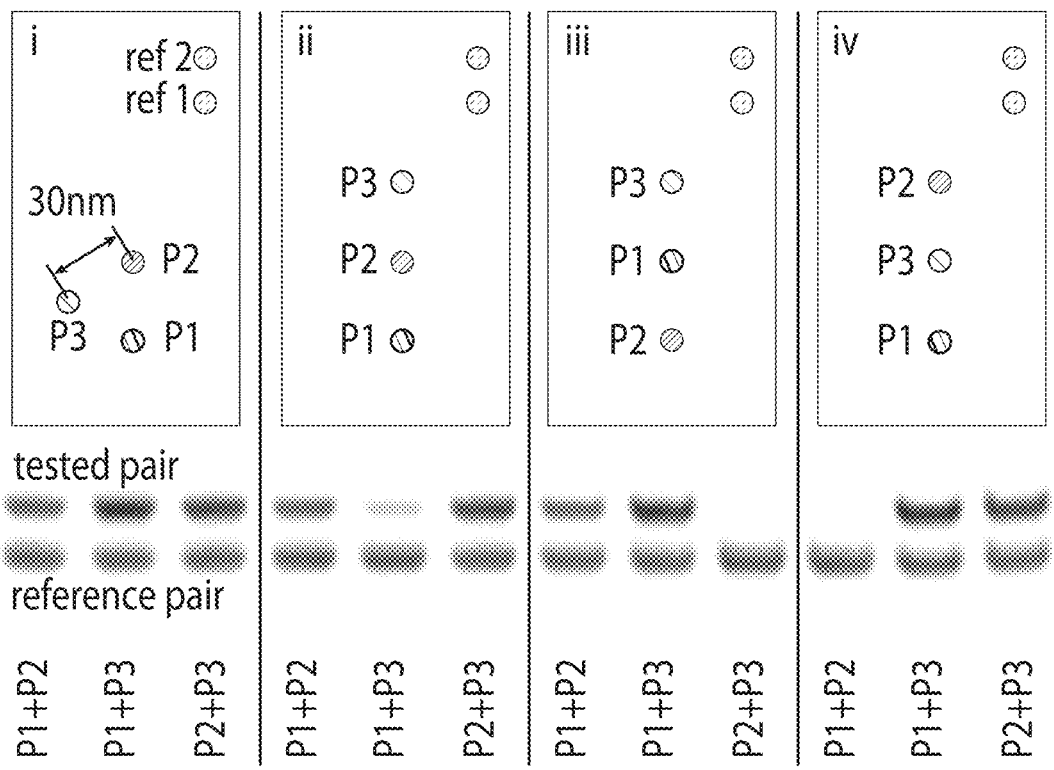

In some embodiments, barcoded records are "decoded" by direct observation by gel electrophoresis or amplification and quantification by PCR (see, e.g., FIG. 19C). This example relies on specific amplification of particular records based on different sequences in their recording primers or barcodes. Massively parallel sequencing is also encompassed by the present disclosure and may be used to decode precise, individual molecular arrangements in large systems (see, e.g., FIG. 3F).

Collected barcoded records are then sequenced. In some embodiments, the records are sequenced using next-generation sequencing technologies. In some embodiments, Sanger sequencing is used as well as "post-next-generation sequencing" technologies under development, such as "nanopore"-based sequencing (e.g., Oxford Nanopore Technologies, nanoporetech.com). In a simplified system, for example, electrophoretic gels may be used to detect combinations of barcodes within a record by differentiating by the length of record produced (see, e.g., FIG. 3b), or standard resolution or super-resolution microscopy may be used to visually detect sequences of probes by fluorescent in situ hybridization or similar approaches. Alternatively, nucleic acid microarrays (e.g., Agilent Technologies) may be used to detect records in a sequence-specific manner.

Figure 13A:
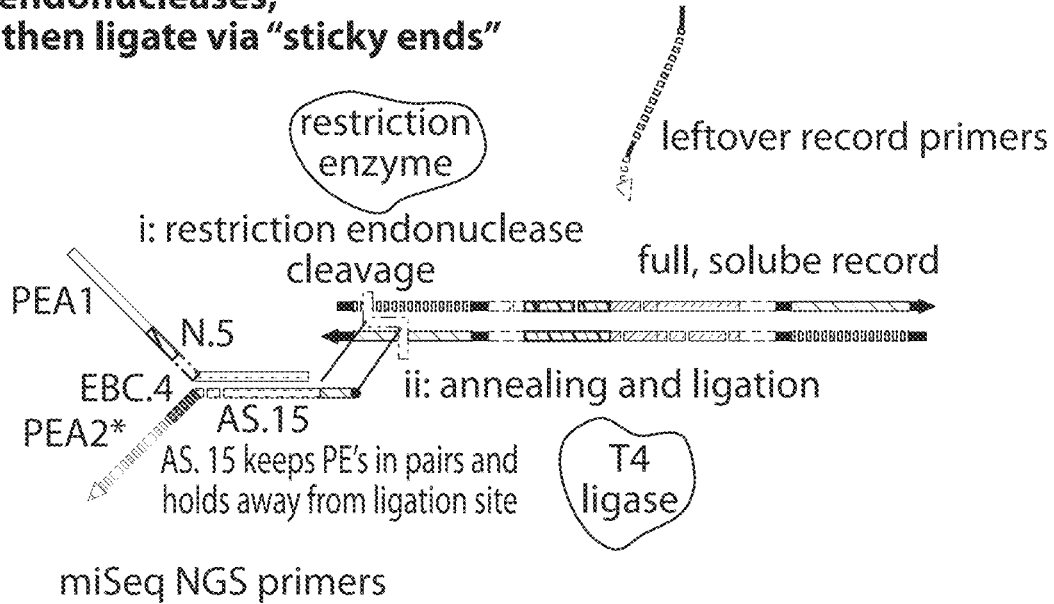
FIGS. 13A and 13B show examples of ligation and amplification methods of the present disclosure. Records may be cut with restriction endonucleases, then ligated via "sticky" ends (FIG. 13A). Excess non-ligated record material may be cut with one or more endonucleases (FIG. 13B)
Figure 13B:
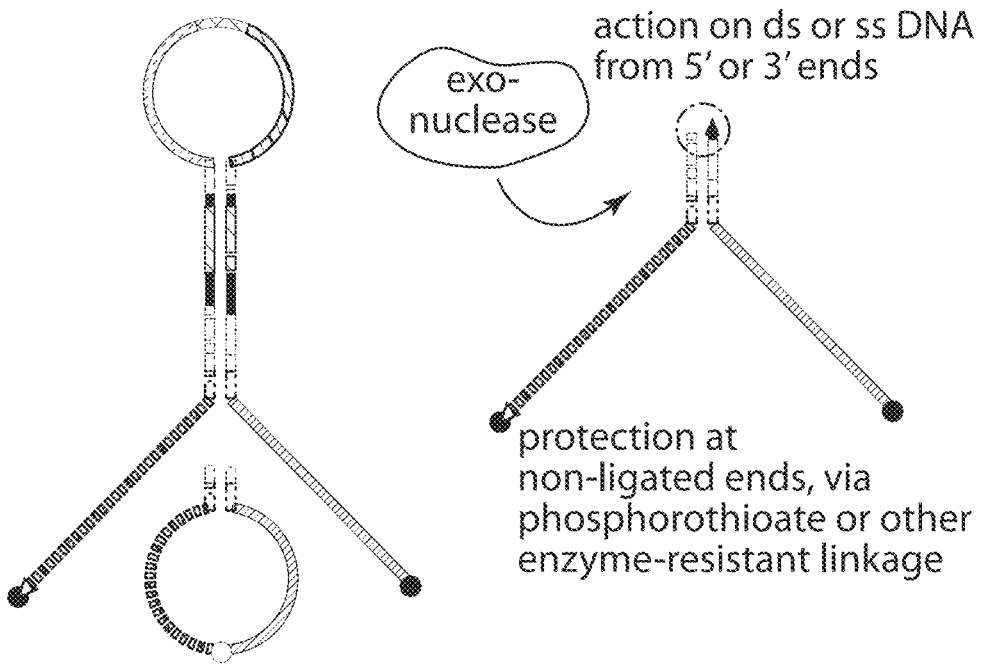

FIGS. 13A-13B show examples of ligation and amplification methods of the present disclosure, used for processing barcoded records. For example, records may be cut with restriction endonucleases, then ligated via "sticky" ends (FIG. 13A). Excess non-ligated record material may be cut with one or more endonucleases (FIG. 13B) The process of ligating sequencing adapters to the records may be performed by blunt end, "A-tailing," or restriction site-mediated ligation. Ligation may be performed on raw, double-stranded records or after annealing into hairpins. Further, primers may be added not as a single species but as any number of species differentiated by a 5' extension that does not participate actively in the record-generating reaction per se, but allows for the two ends of most records to be different (not shown). This in turn allows for PCR amplification with different primers at each end, perhaps incorporating the sequencing adapters, and this amplification may be done before or after ligation. In some embodiments, exonucleases (as single enzymes or in combination, e.g., T7 exonuclease in combination with exonuclease I, III, or T) may be used to digest excess adapter or other sequences, with the target, ligated sequence protected from digestion by end modifications or loop formation.

From the sequencing data obtained, the spatial arrangement of barcoded molecular targets, relative to one another, can be determined. For example, the sequencing data may be processed computationally to produce a representative network of molecular target interactions. Such computer code may read sequencing data files, create a digitally-encoded network of associated barcodes (e.g., 'barcode A connected to B' derived from reading record #1, 'B-C' from record #2, and 'C-A' from record #3). Any number of commercially available (e.g., Mathematica) or independently-written codes are then available for transforming this non-geometric digital representation into one describing relative spatial positioning (known mathematically as aspects of 'graph theory'). In this case, the records imply a triangle-like positioning of targets associated with A, B, and C. Additionally, such programs could calculate statistics of interactions of proteins like the one associated with barcode A by analyzing the interactions of all barcodes associated with that protein (known a priori because the targeting moieties can be linked to specific barcode sets before targeting and reaction are carried out). In addition, the time-dependence of interactions may be determined from these data by analyzing different record sets taken at different times or provided with molecular time-stamps (e.g., primers with slight differences added in the latter half of a reaction).

Some aspects of the present disclosure provide methods that comprise combining in a single reaction (a) two single-stranded nucleic acid barcoded probes, each comprising a palindromic sequence, a barcode sequence and a primer-binding sequence, wherein the barcodes sequences are different from each other, and wherein each barcoded probe is attached to a molecular target, (b) a partially double-stranded primer arranged into a double-stranded region flanked by 3' single-stranded flanking regions that each contain a primer complementary to the primer-binding sequence, wherein the double-stranded region contains a reversible covalent binding site (see, e.g., FIG. 11), and a strand-displacing polymerase.

In some embodiments, the reversible covalent binding site contains a $^{CNV}$K modification (see, e.g., U.S. Pat. No. 8,481,714) such that two strands can be covalently bound in the presence of ultraviolet light and later release in the presence of a difference wavelength of light. Other temperature-stable, reversible linkages may be used, as provided herein.

In some embodiments, the methods comprise incubating (a) and (b) under conditions sufficient to permit binding of the primers to the primer-binding sites and extension of each 3' flanking region of the primers.

In some embodiments, the methods comprise heating the reaction to a temperature of at least 50° C. (e.g., 50° C. to 100° C.) to permit dissociation of the primers from the two single-stranded nucleic acid barcoded probes, thereby regenerating (a) and (b) for further temperature-drive cycling.

Figure 11:
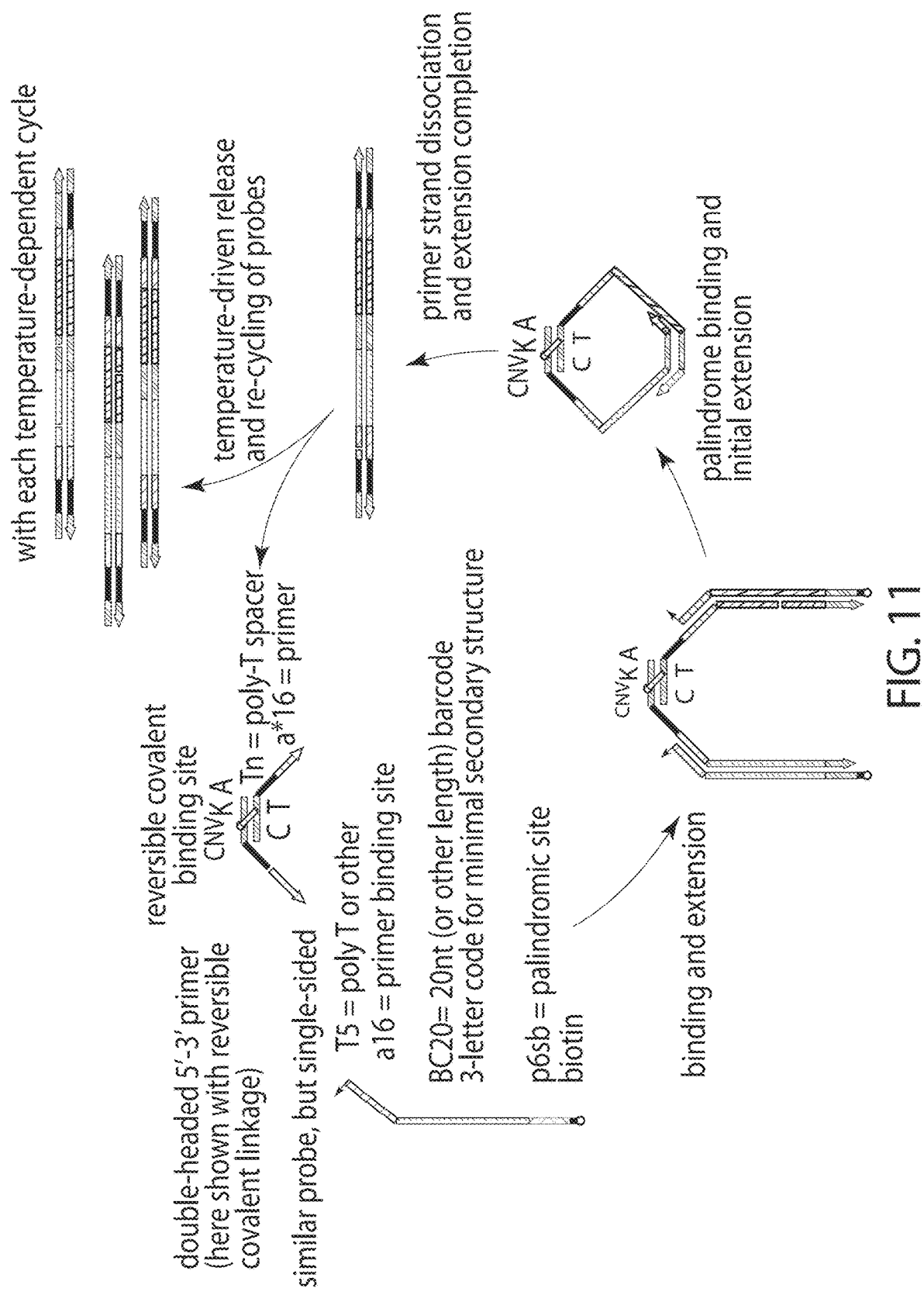
FIG. 11 shows an example of a temperature-dependent-cycling mechanism of the present disclosure, wherein records are copied as before but released from probe pairs upon a temporary increase in temperature instead of by displacement from a complementary probe sequence. As in the (non-temperature-dependent) auto-cycling system, the cycle may then be repeated to create more records from the same probes.

FIG. 11 shows an example of temperature-dependent auto-cycling mechanism of the present disclosure. Records are cyclically created, each record from two separate primers on two unique probes. The nascent "half-records" are not spontaneously driven from the probes, but are instead "melted off" by an elevated temperature. Probes and primers are shown in FIG. 11 with primers as double 3'-headed structures held together by UV-reversible, covalent cross-linking $^{CNV}$K moieties. The primers bind any pair of probes, are extended at low (e.g., 25° C.) temperature to copy barcodes, and are released when the temperature is raised above the melting temperature of the strands (e.g., 70° C.). Upon lowering the temperature again, the polymerase in solution may complete the copying of the strands linked through binding of palindromic sequences, in some embodiments, aided by the release of the $^{CNV}$K linkage. Thus, the system is driven synchronously with temperature cycling.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference, in particular for the teachings that are referenced herein.

Aspects of the present disclosure are further defined by the following numbered paragraphs:

1. A nucleic acid barcoded probe, comprising:
a nucleic acid arranged to form a hairpin structure having a partially-double-stranded primer-binding region, a double-stranded barcode region, a double-stranded palindromic region, and a single-stranded loop region containing a target-binding moiety, wherein a molecule that terminates polymerization is located between the double-stranded palindromic region and the loop region.

2. A nucleic acid barcoded probe comprising one or more nucleic acid strands arranged into:
  (a) a double-stranded palindromic region;
  (b) a double-stranded barcode region; and
  (c) a primer-binding region.

3. The nucleic acid barcoded probe of paragraph 2, wherein the primer-binding region is single-stranded.

4. The nucleic acid barcoded probe of paragraph 2, wherein the primer-binding region is partially double-stranded.

5. The nucleic acid barcoded probe of any one of paragraphs 1-4, wherein the double-stranded palindromic region has a length of 4 to 10 nucleotide base pairs.

6. The nucleic acid barcoded probe of any one of paragraphs 1-5, wherein the double-stranded barcode region has a length of 2 to 100 nucleotide base pairs.

7. The nucleic acid barcoded probe of any one of paragraphs 1-6, wherein the primer-binding region has a length of 4 to 40 nucleotides.

8. The nucleic acid barcoded probe of any one of paragraphs 2-7, wherein the barcoded probe further comprises adjacent to the double-stranded palindromic region a molecule or modification that terminates polymerization.

9. The nucleic acid barcoded probe of any one of paragraphs 2-7, wherein the barcoded probe further comprises adjacent to the double-stranded palindromic region a synthetic non-DNA linker that terminates polymerization.

10. The nucleic acid barcoded probe of any one of paragraphs 2-7, wherein the barcoded probe further comprises adjacent to the double-stranded palindromic region a triethylene glycol spacer that terminates polymerization.

11. The nucleic acid barcoded probe of any one of paragraphs 8-10, wherein the barcoded probe comprises a double-stranded displacement region adjacent to the molecule or modification that terminates polymerization.

12. The nucleic acid barcoded probe of paragraph 11, wherein the double-stranded displacement region has a length of 2 to 10 nucleotide base pairs.

13. The nucleic acid barcoded probe of any one of paragraphs 2-9, wherein the barcoded probe is arranged to form a hairpin structure comprising a single-stranded loop region.

14. The nucleic acid barcoded probe of paragraph 1 or 13, wherein the single-stranded loop region has a length of 3 to 50 nucleotides.

15. The nucleic acid barcoded probe of any one of paragraphs 2-14, further comprising a target-binding moiety.

16. The nucleic acid barcoded probe of paragraph 13 or 14, further comprising a target-binding moiety attached to the single-stranded loop region.

17. The nucleic acid barcoded probe of any one of paragraphs 1, 15 or 16, wherein the target-binding moiety is selected from the group consisting of: biotin, an antibody, an aptamer, a nanobody, a nucleic acid, a drug and an atom.

18. The nucleic acid barcoded probe of any one of paragraphs 1-17, wherein the probe comprises at least one locked nucleic acid (LNA) nucleotide.

19. The nucleic acid barcoded probe of paragraph 18, wherein at least one LNA nucleotide is located in or adjacent to the double-stranded barcoded region.

20. The nucleic acid barcoded probe of any one of paragraphs 1-19, wherein the probe further comprises a single-stranded poly-T end sequence.

21. The nucleic acid barcoded probe of any one of paragraphs 1 or 15-20, wherein the probe is bound to a molecular target through the target-binding moiety.

22. A plurality of the nucleic acid barcoded probes of any one of paragraphs 1-21.

23. The plurality of paragraph 22, wherein the double-stranded palindromic region is the same for each probe of the plurality.

24. The plurality of paragraph 22 or 23, wherein the double-stranded barcode region is unique to each probe of the plurality.

25. The plurality of paragraph 22 or 23, wherein the plurality comprises subsets of barcoded probes, each subset comprising a unique barcode region.

26. The plurality of any one of paragraphs 22-25, wherein the single-stranded primer-binding region is the same for each probe of the plurality.

27. The plurality of paragraph 25, wherein the single-stranded primer-binding region is unique for each subset of barcoded probes of the plurality.

28. The plurality of any one of paragraphs 22-26, wherein each probe of a plurality is bound to a molecular target through a target-binding moiety.

29. A composition, comprising the plurality of any one of paragraphs 22-26 and primer that is at least partially complementary to a primer-binding region of a probe of the plurality.

30. The composition of paragraph 29, wherein the primer comprises at least one nucleotide mismatch relative to the primer-binding region.

31. The composition of paragraph 29, wherein the primer comprises at least one artificial linker that is not complementary to and/or does not bind to the primer-binding region.

32. The composition of any one of paragraphs 29-31, further comprising a strand-displacement polymerase.

33. The composition of paragraph 32, wherein the strand-displacement polymerase is selected from the groups consisting of: Bst large fragment polymerase, phi 29 polymerase, Deep VentR polymerase, Klenow fragment polymerase, and modified Taq polymerase.

34. The composition of any one of paragraphs 29-33, further comprising a helper nucleic acid strand that is partially complementary to the single-stranded primer binding region, is partially complementary to a single-stranded region adjacent to the primer binding region, and binds transiently to the single-stranded region adjacent to the primer binding region.

35. The composition of paragraph 34, wherein the helper strand has a length of 3 to 20 nucleotides.

36. A method of detecting molecular target interactions, comprising the steps of:
  (a) combining in a single reaction the plurality of nucleic acid barcoded probes of paragraph 28 with (i) a primer complementary to the primer-binding region of a probe of the plurality and (ii) a strand-displacement polymerase; and
  (b) incubating the reaction under conditions that result in production of barcoded records.

37. The method of paragraph 36, wherein the barcoded records are double-stranded.

38. The method of paragraph 36 or 37, wherein the step of (b) comprises incubating the reaction at physiological conditions.

39. The method of paragraph 36 or 37, wherein the step of (b) comprises incubating the reaction at a temperature of 37° C. for a time of 0.5 to 3.0 hours.

40. The method of any one of paragraphs 36-39, wherein nucleic acid barcoded probes of the plurality are regenerating following production of the double-stranded barcoded records.

41. The method of any one of paragraphs 36-40, further comprising collecting barcoded records from the reaction.

42. The method of paragraph 41, further comprising purifying barcoded records collected from the reaction.

43. The method of paragraph 42, further comprising sequencing barcoded records collected from the reaction, thereby producing sequencing data.

44. The method of paragraph 43, further comprising reconstructing from the sequencing data an image of molecular target interactions.

45. The method of paragraph 41, further comprising attaching the barcoded records to sequence-specific adapters.

46. The method of paragraph 45, wherein the attaching of the barcoded records to sequence-specific adapters comprises:
(i) dissociating double-stranded barcoded records into single-stranded barcoded records;
(ii) self-annealing each single-stranded barcoded record to form a hairpin structure; and
(iii) ligating each hairpin structure to an adapter sequence, thereby forming adaptor-barcoded records.

47. The method of paragraph 46, further comprising amplifying the adaptor-barcode records by polymerase chain reaction (PCR), thereby producing copies of the adaptor-barcode records.

48. The method of paragraph 47, further comprising purifying the copies of the adaptor-barcode records, thereby producing purified copies of the adaptor-barcode records.

49. The method of paragraph 48, further comprising sequencing the purified copies of the adaptor-barcode records, thereby determining the sequence of the barcoded records.

50. The method of paragraph 49, further comprising computationally processing the sequence of the barcoded records to produce a representative network of molecular target interactions.

51. The method of any one of paragraphs 36-50, wherein the primer comprises:
a first nucleic acid strand comprising
a first sequence complementary to the single-stranded primer-binding region and a second sequence; and
a second nucleic acid strand comprising
a third sequence complementary to the single-stranded primer-binding region and a fourth sequence complementary to and bound to the second sequence,
wherein the first and second nucleic acid strands are arranged into a double-stranded region flanked by single stranded primer regions.

52. The method of paragraph 51, wherein the double-stranded region contains a barcode sequence.

53. The method of paragraph 51 or 52, wherein the primer further comprises at least one sequencing site or attachment site.

54. The method of any one of paragraphs 36-53, wherein the molecular targets are obtained from a biological sample.

55. The method of paragraph 54, wherein the biological sample is a cell or cell lysate.

56. A pair of nucleic acid barcoded probes, comprising:
(a) a first nucleic acid barcoded probe arranged into
(i) a double-stranded barcode region, and
(ii) a single-stranded primer-binding region; and
(b) a second single-stranded barcoded probe comprising a barcode region and a primer region complementary to the single-stranded primer-binding region.

57. The pair of nucleic acid barcoded probes of paragraph 56, wherein the double-stranded barcode region of the first nucleic acid barcoded probe has a length of 5 to 50 nucleotide base pairs.

58. The pair of nucleic acid barcoded probes of paragraph 56 or 57, wherein the single-stranded primer-binding region of the first nucleic acid barcoded probe has a length of 4 to 50 nucleotides.

59. The pair of nucleic acid barcoded probes of any one of paragraphs 56-58, wherein the barcode region of the second nucleic acid barcoded probe has a length of 5 to 50 nucleotides.

60. The pair of nucleic acid barcoded probes of any one of paragraphs 56-59, wherein the primer region of the second nucleic acid barcoded probe has a length of 4 to 50 nucleotides.

61. The pair of nucleic acid barcoded probes of any one of paragraphs 56-60, wherein the first nucleic acid barcoded probe further comprises adjacent to the double-stranded barcode region a molecule or modification that terminates polymerization.

62. The pair of nucleic acid barcoded probes of paragraph 61, wherein the first nucleic acid barcoded probe further comprises adjacent to the double-stranded barcode region a synthetic non-DNA linker that terminates polymerization.

63. The pair of nucleic acid barcoded probes of paragraph 61 or 62, wherein the first nucleic acid barcoded probe comprises a double-stranded displacement region adjacent to the molecule or modification that terminates polymerization.

64. The pair of nucleic acid barcoded probes of paragraph 63, wherein the double-stranded displacement region has a length of 2 to 10 nucleotide base pairs.

65. The pair of nucleic acid barcoded probes of any one of paragraphs 56-64, wherein the first nucleic acid barcoded probe is arranged to form a hairpin structure comprising a single-stranded loop region.

66. The pair of nucleic acid barcoded probes of paragraph 65, wherein the single-stranded loop region has a length of 3 to 50 nucleotides.

67. The pair of nucleic acid barcoded probes of paragraph 65 or 66, wherein the single-stranded loop region contains the single-stranded primer-binding region of (ii).

68. The pair of nucleic acid barcoded probes of any one of paragraphs 56-67, wherein the first nucleic acid barcoded probe and/or the second nucleic acid barcoded probe further comprise(s) a target-binding moiety.

69. The pair of nucleic acid barcoded probes of paragraph 68, wherein the target-binding moiety is located at an end distal to the single-stranded primer-binding region of the first nucleic acid barcoded probe and/or at an end distal to the primer region of the second nucleic acid barcoded probe.

70. The pair of nucleic acid barcoded probes of paragraph 69, wherein the target-binding moiety is selected from the group consisting of: biotin, an antibody, an aptamer, a nanobody and a nucleic acid.

71. The pair of nucleic acid barcoded probes of any one of paragraphs 68-70, wherein each of the first nucleic acid barcoded probe and the second nucleic acid barcoded probe is bound to a molecular target through a target-binding moiety.

72. A composition comprising the pair of nucleic acid barcoded probes of any one of paragraphs 56-71 and a third nucleic acid barcoded probe arranged into a double-stranded barcode region, and a single-stranded primer-binding region, wherein the single-stranded primer-binding region is complementary to and binds to the primer region of the second nucleic acid barcoded probe.

73. The composition of paragraph 72, wherein the third nucleic acid barcoded probe further comprises a target-binding moiety.

74. The composition of paragraph 73, wherein the third nucleic acid barcoded probe is bound to a molecular target through a target-binding moiety is bound to a molecular target.

75. A composition, comprising the pair of nucleic acid barcoded probes of any one of paragraphs 56-71 and a strand-displacement polymerase.

76. The composition of paragraph 75, wherein the strand-displacement polymerase is selected from the group consisting of: Bst large fragment polymerase, phi 29 polymerase, Deep VentR polymerase, Klenow fragment polymerase, and modified Taq polymerase.

77. A method of detecting molecular target interactions, comprising the steps of:
(a) combining in a single reaction the pair of nucleic acid barcoded probes of paragraph 71 and a strand-displacement polymerase; and
(b) incubating the reaction under conditions that result in production of single-stranded barcoded records.

78. A method of detecting molecular target interactions, comprising the steps of:
combining in a single reaction (a) two single-stranded nucleic acid barcoded probes, each comprising a palindromic sequence, a barcode sequence and a primer-binding sequence, wherein the barcodes sequences are different from each other, and wherein each barcoded probe is attached to a molecular target, (b) a partially double-stranded primer arranged into a double-stranded region flanked by 3' single-stranded flanking regions that each contain a primer complementary to the primer-binding sequence, wherein the double-stranded region contains a reversible covalent binding site; and a strand-displacing polymerase;
incubating (a) and (b) under conditions sufficient to permit binding of the primers to the primer-binding sites and extension of each 3' flanking region of the primers; and
heating the reaction to a temperature of at least 50° C. to permit dissociation of the primers from the two single-stranded nucleic acid barcoded probes, thereby regenerating (a) and (b).

EXAMPLES

Example 1

Figure 3D:
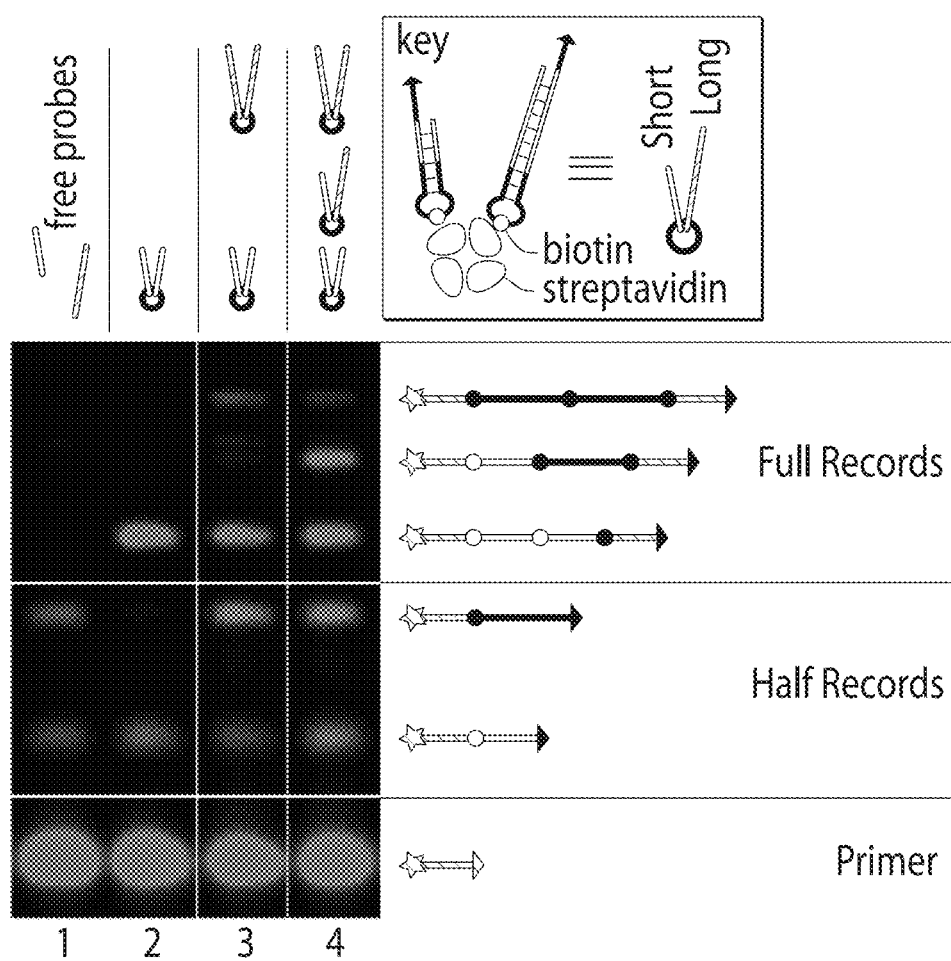
FIG. 3D shows DNA records indicative of barcodes having different lengths and different proximities to one another. Generation of full records requires the co-localization of probes, for example, by biotinylated hairpin loops bound to streptavidin, while isolated probes generate half-records. A cropped denaturing PAGE gel is shown, depicting 10 μl reactions (40 min at 37° C.) with biotin-streptavidin association, a 4:1 overall probe:streptavidin stoichiometry (inset), 8 and 22 nt barcodes (19 and 33 nt stem lengths copied), 10:1 primer:probe, and a 40 nM total probe concentration. A single primer sequence was used and no secondary amplification was performed. Gel quantification showed approximately 5-fold to10-fold primer turnover per barcode.
Figure 3E:
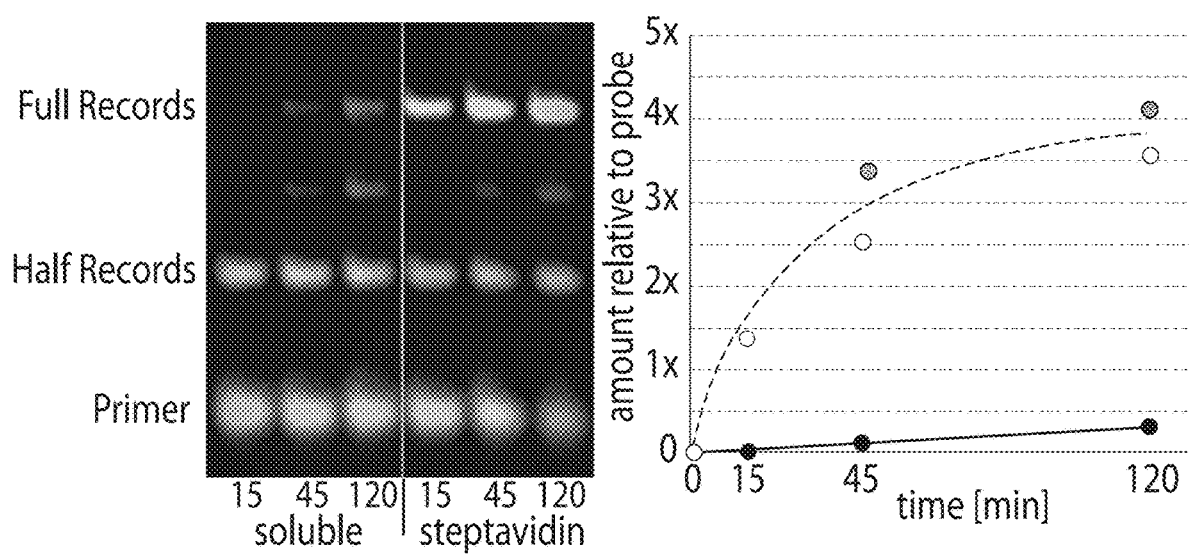
FIG. 3E shows data demonstrating auto-cycling by quantification of Cy5-labeled probes on cropped denaturing PAGE gels. The reaction and gel conditions identical to those of FIG. 3B except for the use of a 10 nucleotide spacer (21 nucleotide stem length copied), and a 5:1 primer:probe ratio, with probes still at a total concentration of 40 nM.
Figure 4A:
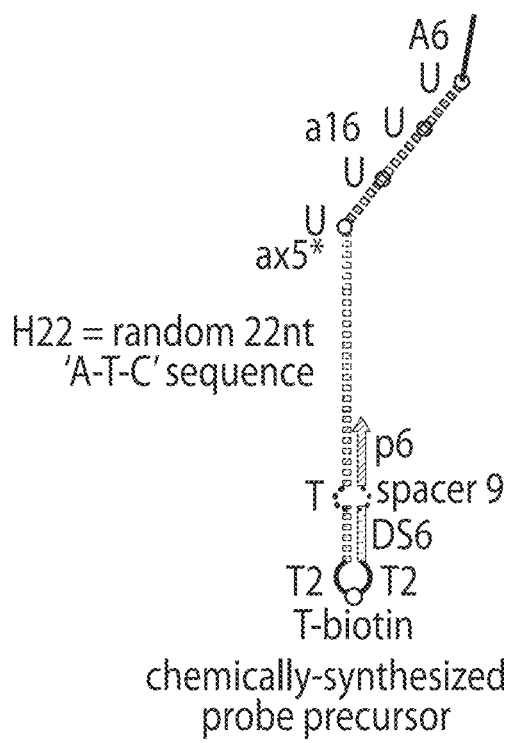
FIGS. 4A-4C shows an example of a method for manufacturing "symmetrical" auto-cycling probes that may be used in accordance with the present disclosure.
Figure 4B:
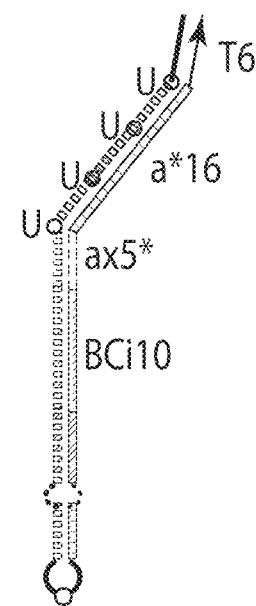
Figure 4C:
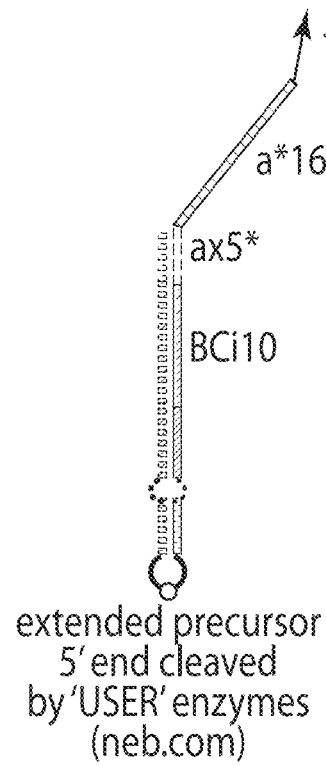

FIG. 3 shows data from an experiment demonstrating an example of a proximity-based, autocyclic, full-record generation method. Lanes 1-4 of the electrophoretic gel each contain combinations of barcoded probes of different lengths and localization (depicted above the gel), together with the primer and polymerase (not depicted). In lane 1, short and long barcoded probes exist unconnected in solution. Cy5-labeled primers (in large excess) were converted to short or long half-records, but no full-records were generated because probes were not proximate to each other. In lane 2, short barcoded probes were co-localized on streptavidin molecules, and short half-records, and subsequently short full-records, were produced. When streptavidin was prepared using either short or long probes, then mixed together for reaction (lane 3), both half-records and full-records of short and long lengths were generated, further indicating that the barcoded probes were proximate to each other, or interacted only locally, when full records were produced. Lane 4 contains the same components as lane 3 plus co-localized short and long probes, which resulted in the generation of intermediate-length full-records, combining short and long half-records. Probes of different lengths are used only for differentiating the records by length (and hence mobility) on the gel in this experiment.

This functional auto-cycling reaction permits repeated barcoded probe reading at constant physiologic temperatures and conditions. Auto-cycling, in combination with unique barcode labeling that allows differentiation of individual molecules, enables true network elucidation and imaging (FIG. 3) with a precision that microscopy and common pairwise proximity methods cannot match. Recording using common pairwise proximity techniques (e.g., co-Immuno-precipitation, proximity ligation) is inherently destructive, and yet elucidation of individual networks (FIG. 2B) is not possible without repeated sampling.

Example 2

Synthetic DNA nanostructures are engineered to display DNA barcodes at arbitrary user-specified positions with nanometer precision, thus serving as a "workbench" for evaluating the performance of the auto-cycler and subsequent image reconstruction method in a rigorous and precise fashion. Sample handling techniques (e.g., microfluidic devices) as well as computational algorithms and software tools for imaging reconstruction based on full-record sequences are used. Protein receptor clusters on cell surfaces are then imaged, first in fixed cells and then in live cells. The labeling of the surface protein clusters is achieved using antibodies and smaller binders, such as nanobodies or aptamers. The Microscope-Free Imaging (MFI) results are compared with data obtained using ultra-high resolution microscope-based methods. MFI is then applied to another application: high-throughput, high resolution imaging of nucleome organization. Finally, in addition to the proximity-based auto-cycling recorder, a diffusion-based molecular recorder is developed, which can repeatedly generate molecular records for targets separated over long range, further expanding the capacity of MFI.

Example 3

Protein Cluster Imaging on Cell Membranes

Methods and composition of the present disclosure may be used to image and elucidate protein clusters in cell plasma membranes. The four similar, membrane-bound EGF receptors of the ErbB family, for example, form a part of complex, modular, heterogeneous network with 13 other polypeptide ligands on the surface of cells. The network mediates cell proliferation and survival as well as migration and adhesion. They dimerize in 10 combinations and appear to form higher-order clusters of up to 150 nm across, implying the co-localization of hundreds of receptors within clusters (Abulrob et al., *J Biol Chem* 285(5): 3145-56, 2010, incorporated by reference herein). Their ability to recognize and process multiple signaling molecules, overexpression in cancer, and rise as drug targets renders them intriguing and important targets for Microscope-Free Imaging (MFI) (Citri and Yarden, *Nat Rev Mol Cell Biol.* 7(7):505-16, 2006, incorporated by reference herein).

Figure 15:
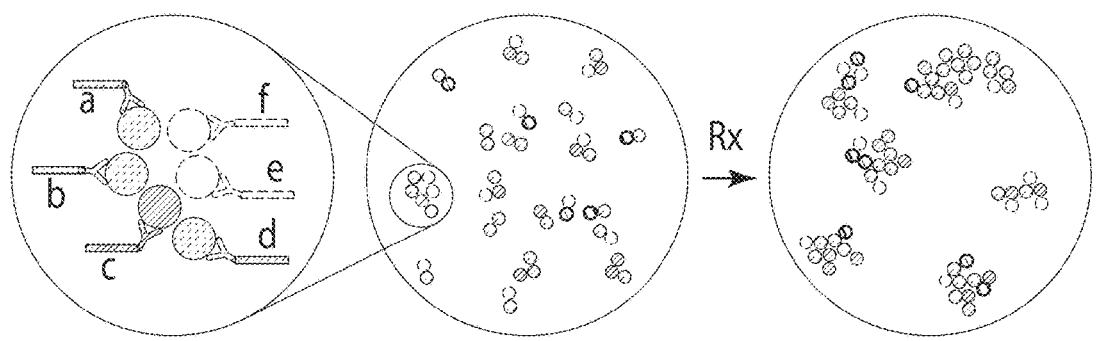
FIG. 15 shows an example application of a microscope-free imaging method of the present disclosure to heterogeneous EGFR membrane protein clusters, which can reconfigure when treated with drugs. Each individual protein (rather than protein species) may be labeled with a unique barcode.

Microscope-free-imaging methods of the present disclosure, as provided herein, reveals many aspects of cluster protein content and behavior (FIG. 15). In a static (fixed) cell, unique labeling of all proteins of interest enables visualization of full network content and connectivity, including association stoichiometry and distribution of protein states within or between cells. In live cells, MFI methods can follow slow (e.g., over tens-to-hundreds of seconds) cluster reconfiguration, and monitor faster processes. Data obtained from MFI methods, as provided herein, offers molecular-scale resolution, true complex network connectivity, and the ability to track dynamic molecular interactions.

For some applications, a $^{CNV}$K-based probe (Yoshimura et al. *Org. Lett.* 10(15): 3227-3230, 2008, incorporated by reference) was created, which can be dissociated with short pulses of 312 nm light. Identification of regions of interest under a scanning confocal microscope with an appropriate laser can disable all probes in a sample except for those in the regions of interest, allowing sampling from tissues in situ.

Further, for some applications, the addition of barcoded primers with "time stamps," e.g., time stamp 1 at condition A, followed by later barcoded primer with time stamp 2 at condition B, permits a coarse time-resolved state changes following, for example, drug delivery for drug screening applications.

Example 4

Nucleome Organization

The organization of two meters of DNA, ncRNA, and proteins in the nucleus is tightly controlled and has functional consequences. Transcriptional regulation, for example, involves the association of DNA-bound proteins and lncRNA that may be far apart on the same or different chromosomes. The overall structure of DNA in the nucleus has received much recent attention since the Chromosome Conformation Capture (3C) method and its variants, which have generated genome-wide maps of intra- and interchromosomal interactions from populations of cells or even individual cells. Data show that large-scale structure is variable between cells, but that small-scale positioning is repeatable and therefore relatively important. Current methods have several limitations: (1) the 4C method generates the highest resolution that, at 10-20 kb, is still longer than the diameter of the nucleus in straightened DNA; (2) the low-resolution pairwise data cannot differentiate homologous chromosomes; and (3) they cannot simultaneously detect the interplay of multiple protein transcription factors, regulatory RNA, and DNA.

Microscope-Free Imaging (MFI) methods of the present disclosure are used to elucidate nucleome organization (FIG. 16). An OligoPaints method (Beliveau et al., *PNAS USA.* 109(52): 21301-21306, 2012, incorporated by reference) is applied to target hundreds of thousands of arbitrary genome segments by in situ hybridization, employing the MFI methods, as provided herein, at each target. Because target regions are not limited by restriction enzyme sequences, and the cycling nature of the recording reaction allows for a probe to participate in many record pairs, the spatial resolution of the final map can be higher than the kilobase-scale resolution offered by 4C and far higher than that of Hi-C. This high resolution and unique labeling of homologous chromosome pairs allow for chromosome identification at a given locus. Similar probes targeted to lncRNAs as well as to transcription factors, cofactors, and chromatin regulators (via antibodies) allow for a more complete picture of regulation. Individual cell differences and correlation to phenotype can be evaluated. These data are differentiated from 3C or microscopy methods by higher spatial resolution, homologous chromosome identification, and parallel, high-throughput protein-DNA or RNA-DNA interaction identification.

In some embodiments, mapping pluripotency or differentiation factor binding and genome organization of embryonic stem (ES) or induced pluripotent stem (iPS) cells is achieved using the methods of the present disclosure. Knowledge of the affiliation and co-affiliation of multiple transcription factors to stem-cell regulation enables further de-differentiation and more complete target differentiation. Additionally, MFI methods of the present disclosure permit mapping of unassembled sequences to the genome. Repetitive sequences, or those surrounded by repeats, can be difficult to localize, but repetitive fluorescence in situ hybridization (FISH) probes with unique barcodes each, followed by proximity-based record generation, ties together sequences that are difficult to read in one reaction.

Example 5

Longer-Range Molecular Interactions

In addition to analyzing molecular target in close proximity, MFI of the present disclosure can be adapted to map targets separated by longer distances. Such long-range data is useful for more comprehensive molecular elucidation. In the protein cluster application, for example, the relative positioning among independent clusters on a cell may be important, and these data can be registered with that of individual cluster measurements if taken by the same mechanism. In addition, the chromosome position application may benefit from additional network data spanning sequences farther than those in direct contact. The mechanism for this intermediate-range (5-25+ nm) acquisition relies on diminishing concentration gradients of released half-records. Short-length primers bind transiently to existing probes are extended into half-records (FIG. 17). The strand displacement reaction occasionally dissociates the half-record to the point of only primer hybridization, and then the sufficiently weak primer hybridization spontaneously dissociates and the half-record diffuses away. A short distance away, it encounters either a bound half-record or another soluble one, the palindromic sites bind each other, and the full-record is polymerized. An optimized balance between reasonable primer binding and spontaneous dissociation was found at a primer length of 7 nucleotides (data not shown).

Example 6

To characterize the rate of Full Record production as a function of probe-probe distance, pairs of probes were fixed to programmed positions on 2D DNA nanostructures (FIG. 19A). Two types were fixed as extensions of intrinsic nanostructure nucleic acid strands, while a third was held by a click-chemistry azide-akyne linkage to an intermediate strand (inset) as a way to demonstrate how probes may be attached to arbitrary moieties. Both methods incorporated single-stranded DNA as flexible linkers. Many copies of a given nanostructures were held flat and immobile on a mica surface (as is done for atomic force microscopy of DNA structures), and recording reactions for each probe separation distance were carried out separately. Records were then amplified by PCR, and products quantified by gel electrophoresis. To account for variation in experimental conditions, especially in the number of nanostructures, a second probe pair with orthogonal PCR sequences was present on each nanostructure type, but always at the same fixed separation distance. The rate of production was calculated with respect to this reference pair.

FIG. 19B indicates the relative recording rate for three probe designs, containing 0, 12, and 18 nt spacer domains. Each probe pair was tested every 6 nm for separations of 6 to 48 nm, and record generation rate mathematical fits were normalized to a common maximum. Zero, 12, and 18 nt probes all produced records near maximum rates when closest to one another, suggesting the local concentration effect was a dominant driver of rate. Rates were reduced to half at 13, 20, and 25 nm, respectively, and had a maximum reach (near zero rate) at 18, 42, and 48 nm. In absolute terms, the 12 nt spacer probe produced records at the fastest rate, approximately twice as fast as the 0 and 18 nt probes (not shown). All three maximum-reach distances correspond well to the expected values when DNA probes and attached Half Records are oriented optimally, as in a straight chain. For the 0 nt spacer probe, the maximum expected distance is twice the sum of the probe length (19 nt of double-stranded DNA, at 0.34 nm per base pair,13~6.5 nm) and Half Record length (11 nt of single-stranded DNA minus 3 nt palindrome overlap, at the maximum 0.58 nm per base,13~4.6 nm), totaling~22 nm (geometry as in FIG. 2c, after step ii). Similarly, the 12 nt and 18 nt spacer probes have a maximum expected reach of ~36 and ~43 nm, respectively. Estimates using worm-like chain models are similar.

The longest probe, with an 18 nt spacer, was used to test the ability of APR to determine the relative positions of three targets. Three such probes, programmed with different primer sequences and therefore generating records with unique ends, were again fixed by 2D nanostructure in each of four configurations with 30 nm probe separation (FIG. 19C). When placed in a triangular configuration (FIG. 19C, panel (i)), where each probe is equidistant from each other, all three records are produced and prominently visible on the gel, indicating the close proximity of each pair and therefore a triangular arrangement. However, when placed in a line where adjacent probes are within reach but distant probes are not, only products of adjacent probes are prominent. The three possible orders of the linear arrangement each produce the appropriate records (FIG. 19C, panels (ii)-(iv)), demonstrating an ability to record geometric information from three molecular-scale targets in arbitrary configuration. This method can be applied to more than three simultaneous targets simply by designing additional probes of orthogonal primer sequence.

Example 7

Figure 20A:
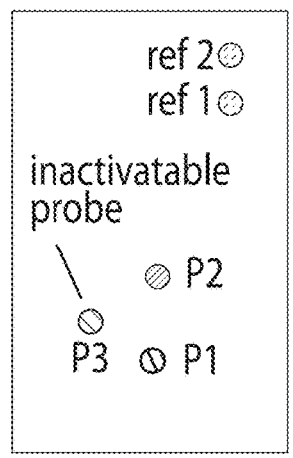
FIGS. 20A-20B present data characterizing state changes. The same nanostructure probe triangle was used as in FIG. 19C, panel (i), except that probe P3 could be de-activated (FIG. 20A).
Figure 20B:
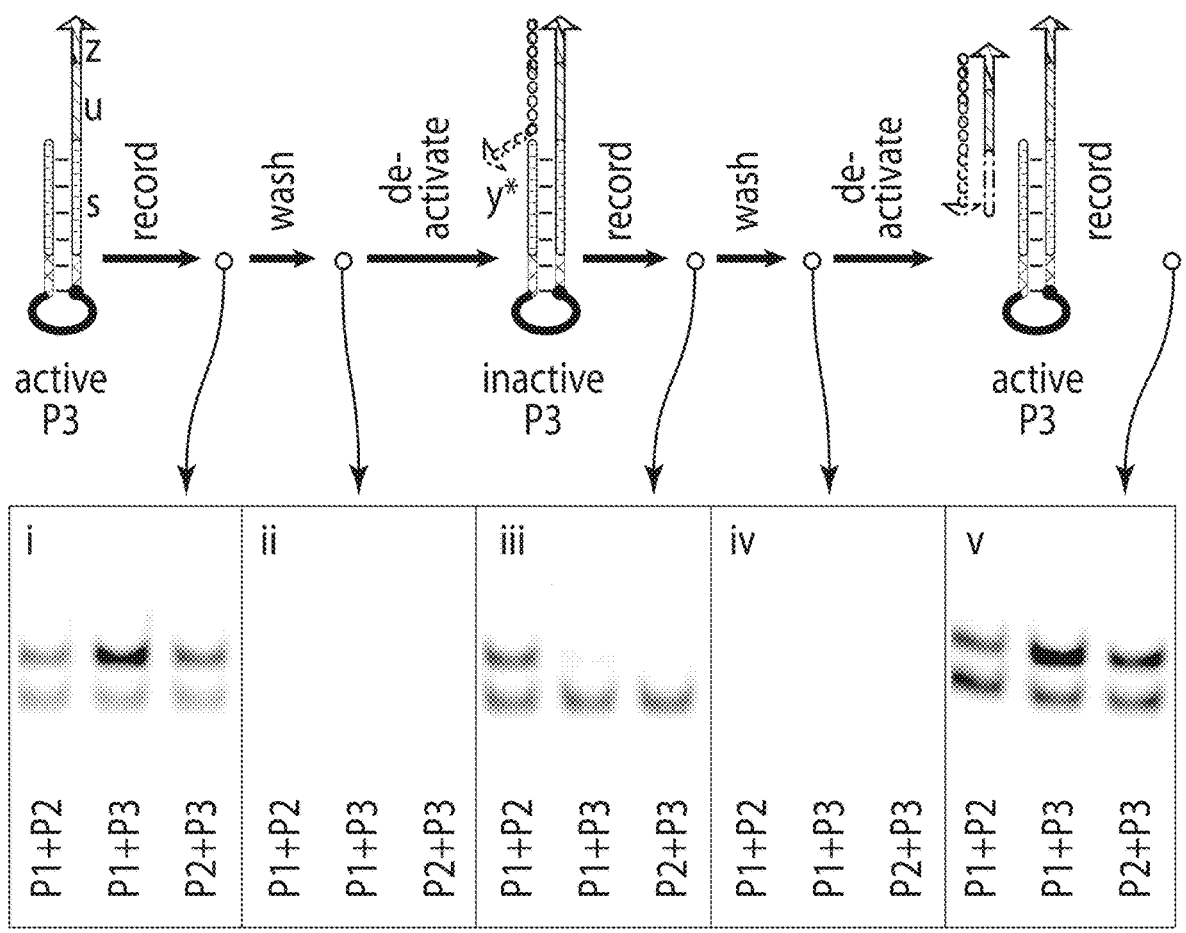

In addition to identifying underling molecular organization, the re-sampling of a changing system was demonstrated. The same nanostructure-based, triangular arrangement of probes of FIG. 19C, panel(i), was constructed, with a mechanism for inactivating probe P3 (FIG. 20A). At each sampling point, the supernatant was PCR-amplified and observed by denaturing PAGE. First, the triangular arrangement was recorded and sampled, indicating the co-localization of three probes as expected (FIG. 20B, panel (i)). After a wash with buffer, the supernatant was sampled and indicated no residual records (FIG. 20B, panel (ii)). Then, by applying an inextensible P3 blocking primer z*-u* (inverted dT at 3' end) to the system, leftover P3 primers u* and Half Records were displaced and that probe was unable to further bind primer, rendering it deactivated. Washing, recording, and re-sampling indicated co-localization of only the two lower probes (FIG. 20B, panel (iii)).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of detecting co-localization of a first protein target and a second protein target, comprising:
    (a) providing, in a reaction mixture, the first protein target, the second protein target, a strand-displacing polymerase, a first nucleic acid primer, a second nucleic acid primer, a first nucleic acid probe, and a second nucleic acid probe,
    wherein
        (i) the first nucleic acid probe and the second nucleic acid probe each comprise a molecule that terminates polymerization, a double-stranded palindromic region, a double-stranded barcode region comprising a barcode sequence, and a single-stranded region,
        (ii) the first nucleic acid probe is linked to a first antibody that specifically binds to the first protein target, and the second nucleic acid probe is linked to a second antibody that specifically binds to the second protein target, and
        (iii) the first primer specifically binds to the single-stranded region of the first nucleic acid probe, and the second primer specifically binds to the single-stranded region of the second nucleic acid probe; and
    (b) incubating the reaction mixture under conditions that result in production of a nucleic acid comprising the barcode sequence of the first nucleic acid probe and the barcode sequence of the second nucleic acid probe; and
    (c) sequencing the nucleic acid comprising the barcode sequence of the first nucleic acid probe and the barcode sequence of the second nucleic acid probe, wherein the presence of the barcode sequence of the first nucleic acid probe and the barcode sequence of the second nucleic acid probe is indicative of co-localization of the first protein target and the second protein target.

2. The method of claim 1, wherein each of the first and second nucleic acid probes forms a hairpin structure comprising a loop region adjacent to the double-stranded palindromic region.

3. The method of claim 1, wherein the conditions that result in the production of the nucleic acid comprise physiological conditions.

4. The method of claim 1, wherein the conditions that result in the production of the nucleic acid comprise a temperature of 20-40 degrees Celsius, atmospheric pressure of 1, and/or a pH value of 6-8.

5. The method of claim 4, wherein the conditions that result in the production of the nucleic acid comprise a temperature of 37 degrees Celsius and a period of time of 0.5 to 3.0 hours.

6. The method of claim 1, wherein each of the double-stranded palindromic regions has a length of 4 to 10 nucleotide base pairs, each of the double-stranded barcode regions has a length of 5 to 50 nucleotide base pairs, and/or wherein each of the single-stranded regions has a length of 4 to 50 nucleotides.

7. The method of claim 1, wherein the molecule that terminates polymerization is a modified nucleotide, synthetic non-DNA linker, triethylene glycol spacer, or double-stranded displacement region.

8. The method of claim 1, wherein the strand-displacing polymerase is a Bst large fragment polymerase, phi 29 polymerase, Deep VentR polymerase, Klenow fragment polymerase, or modified Taq polymerase.

9. The method of claim 1, wherein, in the first nucleic acid probe or the second nucleic acid probe, the molecule that terminates polymerization is adjacent to the double-stranded palindromic region, the double-stranded palindromic region is adjacent to the double-stranded barcode region, the double-stranded barcode region is adjacent to the single-stranded region, and the a single-stranded region is located at a 3' end of the first nucleic acid probe or the second nucleic acid probe.

10. The method of claim 1, wherein each of the first and second nucleic acid probes comprise deoxyribonucleic acid.

11. The method of claim 1, further comprising purifying the nucleic acid after (b).

12. The method of claim 1, wherein, in the first nucleic acid probe or the second nucleic acid probe, the molecule that terminates polymerization is adjacent to the double-stranded palindromic region, the double-stranded palindromic region is adjacent to the double-stranded barcode region, the double-stranded barcode region is adjacent to the single-stranded region, and the single-stranded region is located at a 3' end of the first nucleic acid probe or the second nucleic acid probe.

13. The method of claim 1, wherein each of the first and second nucleic acid probes further comprises a double-stranded stem region.

14. A composition comprising:
    a first protein target, a second protein target, a strand-displacing polymerase, a first nucleic acid primer, a second nucleic acid primer, a first nucleic acid probe, and a second nucleic acid probe, wherein
    (i) the first nucleic acid probe and the second nucleic acid probe each comprise a molecule that terminates polymerization, a double-stranded palindromic region, a double-stranded barcode region comprising a barcode sequence, and a single-stranded region,
    (ii) the first nucleic acid probe is linked to a first antibody that specifically binds to the first protein target, and the second nucleic acid probe is linked to a second antibody that specifically binds to the second protein target, and
    (iii) the first primer specifically binds to the single-stranded region of the first nucleic acid probe, and the second primer specifically binds to the single-stranded region of the second nucleic acid probe.

15. The composition of claim 14 further comprising a nucleic acid comprising the barcode sequences of the first and second nucleic acid probes.

16. The composition of claim 14, wherein each of the double-stranded palindromic regions has a length of 4 to 10 nucleotide base pairs, each of the double-stranded barcode regions has a length of 5 to 50 nucleotide base pairs, and/or wherein each of the single-stranded regions has a length of 4 to 50 nucleotides.

17. The composition of claim 14, wherein each of the first and second nucleic acid probes further comprises a double-stranded stem region.

18. The composition of claim 14, wherein the molecule that terminates polymerization is a modified nucleotide, synthetic non-DNA linker, triethylene glycol spacer, or double-stranded displacement region.

19. The composition of claim 14, wherein the strand-displacing polymerase is a Bst large fragment polymerase, phi 29 polymerase, Deep VentR polymerase, Klenow fragment polymerase, or modified Taq polymerase.

* * * * *

```
                        SEQUENCE LISTING

<160> NUMBER OF SEQ ID NOS: 7

<210> SEQ ID NO 1
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 1
agtcagctcg agctaggtct agagctaggc tatcactagt gatagcctag ctctagacct      60
agctcgagct actt                                                       74

<210> SEQ ID NO 2
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 2
agtcagctcg agctaggtct tagcgtaggc tacaactagt gctagctagc gagcagacct      60
agctcgagct actt                                                       74

<210> SEQ ID NO 3
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 3
agtcagctcg agctaggtct agcgctatct agctactagt atcgtactgt gacgagacct      60
agctcgagct actt                                                       74

<210> SEQ ID NO 4
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 4
agtcagctcg agctaggtct gatctagcgt agccactagt aggctctagc gactagacct      60
agctcgagct actt                                                       74

<210> SEQ ID NO 5
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 5
agtcagctcg agctaggtct aggctctagc tagcactagt cgatagctag cgaaagacct      60
agctcgagct actt                                                       74
```

```
<210> SEQ ID NO 6
<211> LENGTH: 79
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(7)
<223> OTHER INFORMATION: n is deoxyuridine
<220> FEATURE:
<221> NAME/KEY: misc_feature
<222> LOCATION: (11)..(11)
<223> OTHER INFORMATION: n is deoxyuridine
<220> FEATURE:
<221> NAME/KEY: misc_feature
<222> LOCATION: (18)..(18)
<223> OTHER INFORMATION: n is deoxyuridine
<220> FEATURE:
<221> NAME/KEY: misc_feature
<222> LOCATION: (22)..(22)
<223> OTHER INFORMATION: n is deoxyuridine
<220> FEATURE:
<221> NAME/KEY: misc_feature
<222> LOCATION: (28)..(49)
<223> OTHER INFORMATION: n is a, c, or t
<220> FEATURE:
<221> NAME/KEY: misc_feature
<222> LOCATION: (65)..(65)
<223> OTHER INFORMATION: t is modified with biotin
<220> FEATURE:
<221> NAME/KEY: misc_feature
<222> LOCATION: (73)..(74)
<223> OTHER INFORMATION: modified with spacer 9

<400> SEQUENCE: 6
aaaaaancat ncccagcnta cnctcacnnn nnnnnnnnnn nnnnnnnnna ccggttcgct    60 ggttttttcca gcgaccggt                                               79

<210> SEQ ID NO 7
<211> LENGTH: 16
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is deoxyuridine
<220> FEATURE:
<221> NAME/KEY: misc_feature
<222> LOCATION: (5)..(5)
<223> OTHER INFORMATION: n is deoxyuridine
<220> FEATURE:
<221> NAME/KEY: misc_feature
<222> LOCATION: (12)..(12)
<223> OTHER INFORMATION: n is deoxyuridine
<220> FEATURE:
<221> NAME/KEY: misc_feature
<222> LOCATION: (16)..(16)
<223> OTHER INFORMATION: n is deoxyuridine

<400> SEQUENCE: 7
ncatncccag cntacn                                                   16
```